(12) United States Patent
Sasago et al.

(10) Patent No.: US 10,429,340 B2
(45) Date of Patent: Oct. 1, 2019

(54) GAS SENSOR

(71) Applicant: HITACHI METALS, LTD., Tokyo (JP)

(72) Inventors: Yoshitaka Sasago, Tokyo (JP); Shuntaro Machida, Tokyo (JP); Hitoshi Nakamura, Tokyo (JP); Takahiro Odaka, Tokyo (JP)

(73) Assignee: Hitachi Metals, Ltd., Tokyo (JP)

( * ) Notice: Subject to any disclaimer, the term of this patent is extended or adjusted under 35 U.S.C. 154(b) by 46 days.

(21) Appl. No.: 15/910,892

(22) Filed: Mar. 2, 2018

(65) Prior Publication Data
US 2018/0284060 A1 Oct. 4, 2018

(30) Foreign Application Priority Data

Mar. 31, 2017 (JP) ................. 2017-070864

(51) Int. Cl.
| | |
|---|---|
| *G01N 27/414* | (2006.01) |
| *H01L 23/29* | (2006.01) |
| *H01L 29/49* | (2006.01) |
| *H01L 23/31* | (2006.01) |

(52) U.S. Cl.
CPC ....... *G01N 27/4141* (2013.01); *H01L 23/291* (2013.01); *H01L 23/3192* (2013.01); *H01L 29/4966* (2013.01)

(58) Field of Classification Search
CPC .............. G01N 27/4141; H01L 23/291; H01L 29/4966; H01L 23/3192
See application file for complete search history.

(56) References Cited

U.S. PATENT DOCUMENTS

| | | | |
|---|---|---|---|
| 9,484,448 B2 | 11/2016 | Usagawa | |
| 2007/0220954 A1 | 9/2007 | Fleischer et al. | |
| 2016/0103082 A1* | 4/2016 | Kimura | G01N 25/20 73/25.01 |

FOREIGN PATENT DOCUMENTS

| | | |
|---|---|---|
| JP | 63-128246 A | 5/1988 |
| JP | 08-271476 A | 10/1996 |
| JP | 2013-242271 A | 12/2013 |
| JP | 2016-085124 A | 5/2016 |

* cited by examiner

*Primary Examiner* — Selim U Ahmed
(74) *Attorney, Agent, or Firm* — Volpe and Koenig, P.C.

(57) ABSTRACT

A sensor element includes a sensor FET provided in a main surface of a semiconductor substrate, a cavity provided in the sensor FET and into which a detection target gas is introduced, and an ion pump provided over the cavity. By laminating the ion pump over the sensor FET via the cavity, a part of a front surface of a gate layer is exposed to the cavity, and a part of a lower surface of an ion pump electrode is exposed to the cavity. When the gate layer comes into contact with the detection target gas, a work function changes, so that gas concentration can be detected.

15 Claims, 38 Drawing Sheets

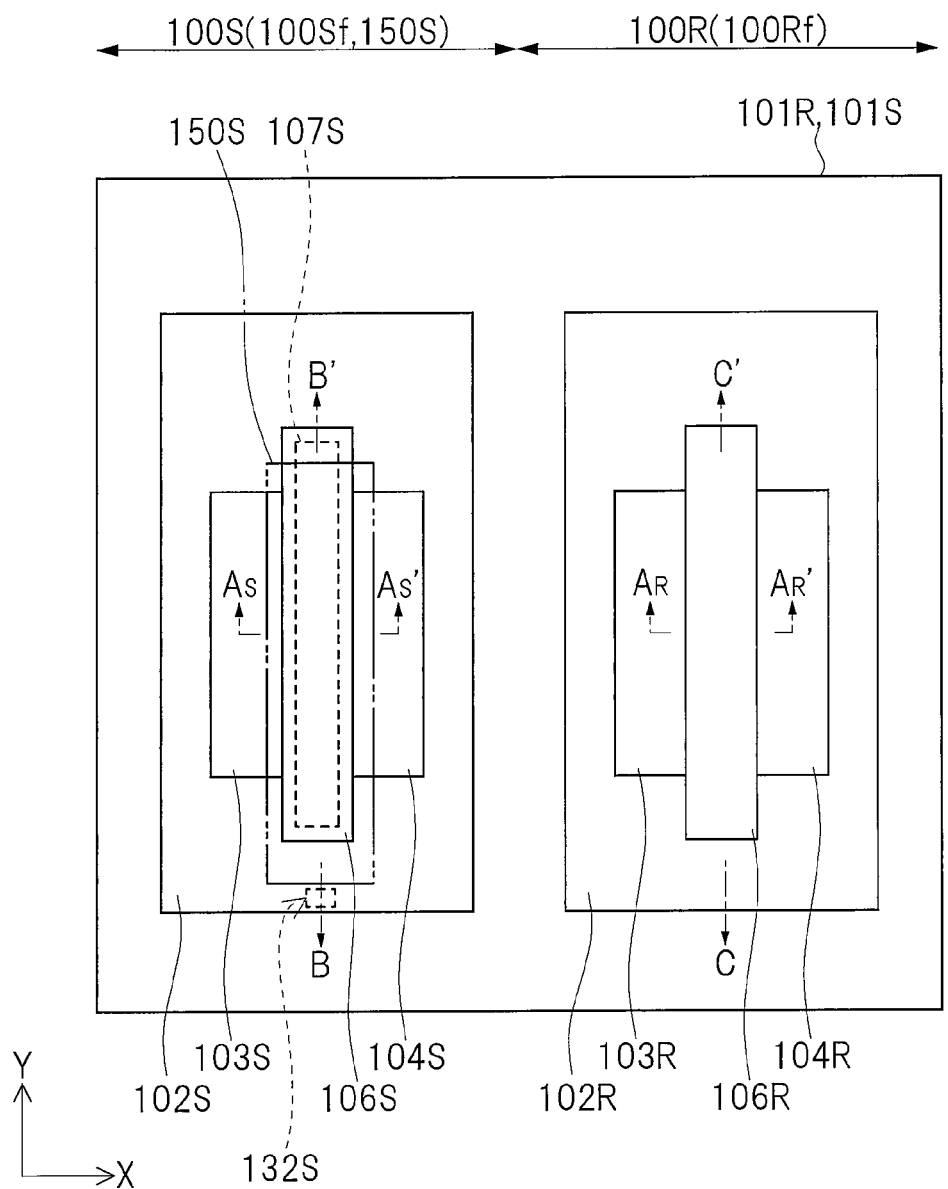

100Sf

100Rf

100Sd

100Rd

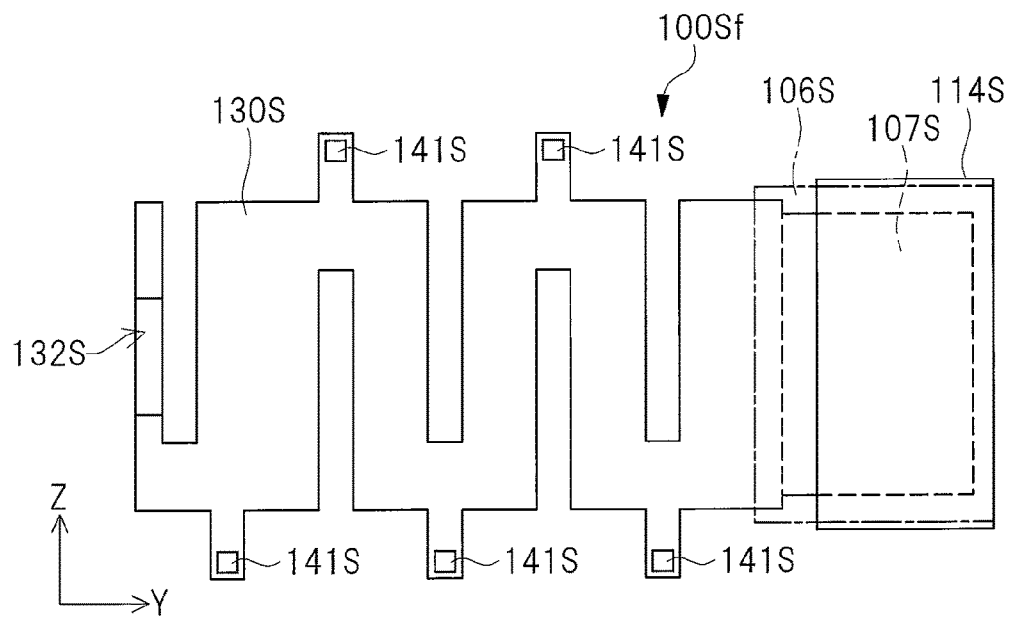
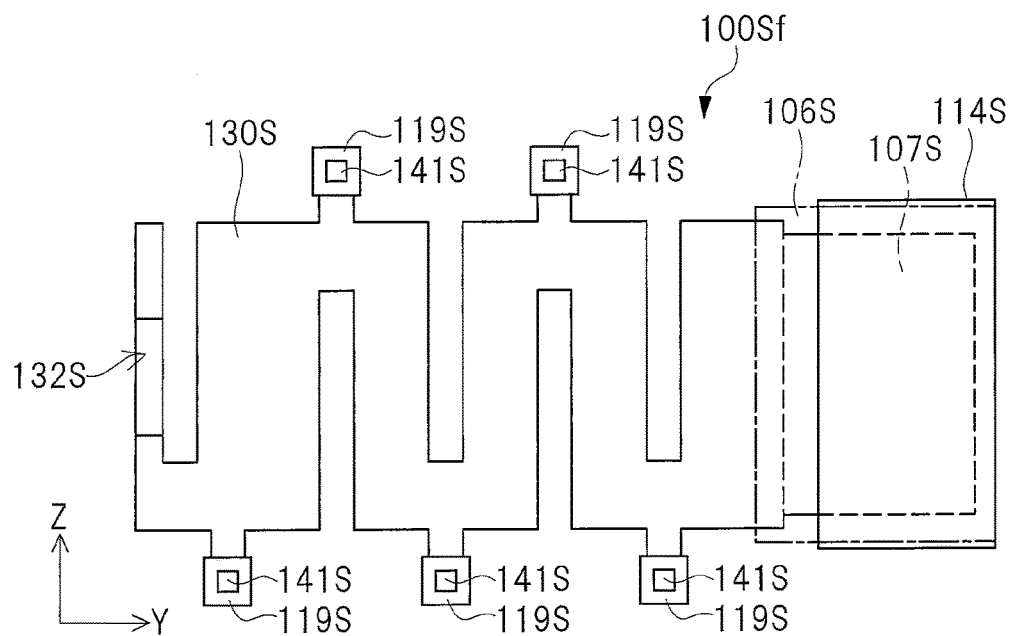

GAS SENSOR

CROSS-REFERENCE TO RELATED APPLICATION

The present application claims priority from Japanese Patent Application No. 2017-070864 filed on Mar. 31, 2017, the content of which is hereby incorporated by reference into this application.

TECHNICAL FIELD OF THE INVENTION

The present invention relates to a gas sensor, and more particularly, to a work function type gas sensor in which threshold change occurs depending on gas concentration, for example, an FET (Field Effect Transistor) type gas sensor, a capacitor type gas sensor, and a diode type gas sensor.

BACKGROUND OF THE INVENTION

Background techniques in this technical field include Japanese Patent Application Laid-Open Publication No. 2016-085124 (Patent Document 1), Japanese Patent Application Laid-Open Publication No. 2013-242271 (Patent Document 2), US Unexamined Patent Application Publication No. 2007/0220954 (Patent Document 3), Japanese Patent Application Laid-Open Publication No. H8-271476 (Patent Document 4), and Japanese Patent Application Laid-Open Publication No. S63-128246 (Patent Document 5).

Japanese Patent Application Laid-Open Publication No. 2016-085124 (Patent Document 1) describes a gas sensor which obtains temporal change in difference between a threshold voltage of a sensor FET and a threshold voltage of a reference FET, and separates the difference of the threshold voltage caused by hydrogen gas and the difference of the threshold voltage caused by radiation from an initial value of the difference, an elapsed time of the difference, and a first-order derivative signal of the temporal change of the difference, thus measuring hydrogen gas concentration.

Japanese Patent Application Laid-Open Publication No. 2013-242271 (Patent Document 2) discloses a semiconductor gas sensor in which a gate insulation film is formed on an Si layer, a reformed TiOx film is formed on the gate insulation film, and a Pt film was formed on the reformed TiOx film. The Pt film includes a plurality of Pt crystal grains, and Ti and O are present in the crystal grain boundary gaps among the plurality of Pt crystal grains, and in particular, TiOx nanocrystals are formed around a front surface in proximity to the grain boundary triple junction.

US Unexamined Patent Application Publication No. 2007/0220954 (Patent Document 3) describes an FET gas sensor including a gas channel that diffuses a measurement gas in a gas sensing layer connected for signal reading.

Japanese Patent Application Laid-Open Publication No. H8-271476 (Patent Document 4) discloses a measurement apparatus for measuring gas components that includes a first internal space, a second internal space, first oxygen pumping means for controlling the oxygen partial pressure in the first internal space, second oxygen pumping means for pumping oxygen in the second internal space, and current detecting means for detecting a pump current flowing by operation of the second oxygen pumping means. In this measurement apparatus, a gas component amount to be measured is obtained from a value of the pump current detected by the current detecting means.

Japanese Patent Application Laid-Open Publication No. S63-128246 (Patent Document 5) describes an FET type sensor in which a film of a solid electrolyte made of a material capable of generating an electromotive force corresponding to an amount of oxygen ions at room temperature is laminated on a gate insulation film, and a metal film made of a material that catalyzes a reaction for dissociating oxygen molecules into oxygen ions is formed as a gate electrode on the film of the solid electrolyte.

SUMMARY OF THE INVENTION

In an actual use environment of a gas sensor, there are gases other than a detection target gas, and the gases include interfering gases to which the gas sensor responds like the detection target gas. For this reason, for example, in a work function type gas sensor, an ion pump is provided as a separate part as a countermeasure against interfering gases. However, when the work function type gas sensor is used in combination with an ion pump as a separate part, there is a problem in that advantages of the work function type gas sensor such as low cost, small size, and low power consumption are lost.

In order to solve the above problems, according to the present invention, a sensor element includes a work function type gas sensor provided in a main surface of a semiconductor substrate, an ion pump removing an interfering gas component from a detection target gas, and a gas diffusion prevention film formed between the work function type gas sensor and the ion pump, in which a cavity into which the detection target gas is introduced is formed in the gas diffusion prevention film. The ion pump includes an ion conductive film, a first ion pump electrode formed to be in contact with a lower surface of the ion conductive film, and a second ion pump electrode formed to be in contact with an upper surface of the ion conductive film, in which a part of a front surface of the gate layer of the work function type gas sensor is exposed to the cavity, and a part of a lower surface of the first ion pump electrode is exposed to the cavity.

According to the present invention, it is possible to provide a gas sensor capable of realizing low cost, small size, and low power consumption, and suppressing an influence of an interfering gas.

Problems, configurations, and effects other than those described above will be apparent from the following description of the embodiments.

BRIEF DESCRIPTIONS OF THE DRAWINGS

FIG. 2 is a plan view showing an example of a configuration of a sensor unit of the gas sensor according to the first embodiment;

FIG. 34A is a plan view showing an example of a cavity filled with a sacrificial film according to a seventh embodiment;

FIG. 34B is a plan view showing an example of a cavity from which a sacrificial film has been removed according to the seventh embodiment;

DESCRIPTIONS OF THE PREFERRED EMBODIMENTS

Figure 1:
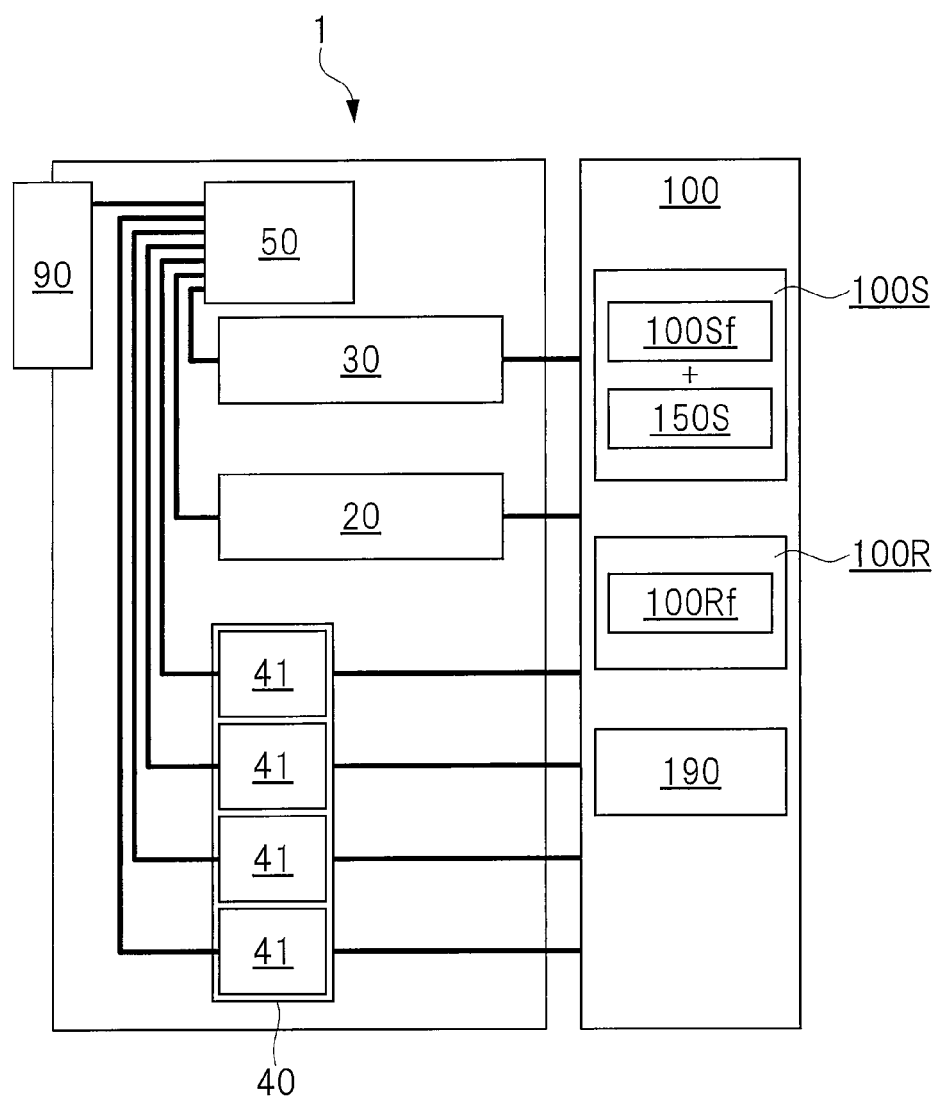
FIG. 1 is a schematic diagram showing an example of a configuration of a gas sensor according to a first embodiment.

Embodiments will be described in detail below with reference to the accompanying drawings. Note that components having the same function are denoted by the same or related reference characters throughout the drawings for describing the embodiments, and the repetitive description thereof is omitted. Also, when a plurality of similar members (portions) are present, a symbol is added to a reference character of a collective term to indicate an individual or specific portion, in some cases. In addition, the description of the same or similar portions is not repeated in principle unless particularly required in the following embodiments.

Also, in the following embodiments, as a direction to be used for description, an X direction, a Y direction, and a Z direction are used. The X direction and the Y direction are directions crossing with each other and constituting a horizontal plane, and the Z direction is a vertical direction with respect to the horizontal plane.

Also, in some drawings used in the embodiments, hatching may be omitted even in a cross-sectional view so as to make the drawings easy to see. Also, hatching may be used even in a plan view so as to make the drawings easy to see.

Also, in cross-sectional views and plan views, a size of each portion does not correspond to that of an actual device, and a specific portion is shown relatively largely so as to make the drawings easy to see, in some cases. Also, even when a plan view corresponds to a cross-sectional view, a specific portion is shown relatively largely so as to make the drawings easy to see, in some cases.

Detailed Description of Problems

A gas sensor is used, for example, for measuring gas concentration or detecting leak of a gas for the purpose of preventing explosion of flammable gases (such as hydrogen or methane) and preventing adverse effects of toxic gases (nitrogen oxide, hydrogen sulfide, carbon monoxide, etc.) on the human body. Also, in engine automobiles, a gas sensor is used for engine control for improving fuel consumption and reducing harmful gas, feedback to purifier control or failure detection, and the like.

In recent years, development of an FET type gas sensor for hydrogen sensor has been advanced toward practical use (Patent Documents 1, 2, and 3 above). The FET type gas sensor is a gas sensor whose threshold value changes depending on gas concentration of a detection target gas. Like the FET type gas sensor, gas sensors whose threshold value changes depending on gas concentration include a capacitor type gas sensor and a diode type gas sensor. The FET type gas sensor, the capacitor type gas sensor, and the diode type gas sensor are collectively referred to as a work function type gas sensor.

The work function type gas sensor can be manufactured by a process using a semiconductor wafer, and therefore, the work function type gas sensor can achieve low cost, small size, and low power consumption as compared with other gas sensors, for example, a limiting-current type gas sensor (Patent Document 4). In addition to hydrogen gas, for example, there is a report of an FET type gas sensor which detects oxygen gas (Patent Document 5). In addition to the work function type gas sensor using a silicon (Si) substrate, a work function type gas sensor using a silicon carbide (SiC) substrate which can operate at up to high temperature has also been reported.

As mentioned above, the FET type gas sensor, the capacitor type gas sensor, and the diode type gas sensor are suitable for reduction in cost, size, and power consumption. Meanwhile, in the actual use environment of the gas sensor, there are gases other than the detection target gas, and such gases contain interfering gases to which the gas sensor responds like the detection target gas. As a countermeasure for the interfering gas, a system using an ion pump is effective. Patent Document 4 discloses a technique of a gas sensor of a limiting-current type, in which oxygen as an interfering gas is removed from the atmosphere by forming electrodes on both sides of a ceramic substrate to be an ion conductive film. Further, Patent Document 3 discloses a technique for removing an interfering gas by attaching an FET type hydrogen sensor to a substrate on which an ion pump is formed.

However, the gas sensor of Patent Document 4 is disadvantageous in terms of reduction in cost, size, and power consumption as compared with the work function type gas sensor such as the FET type gas sensor. Also, in the gas sensor of Patent Document 3, although the FET type gas sensor itself is suitable for reduction in cost, size, and power consumption, it is necessary to form and use an ion pump in combination as a separate part. Therefore, the FET type gas sensor may lose its advantages such as low cost, small size, and low power consumption.

First Embodiment

<Configuration of Gas Sensor>

A configuration of a gas sensor according to the first embodiment will be described with reference to FIG. 1 to FIG. 7.

Figure 3A:
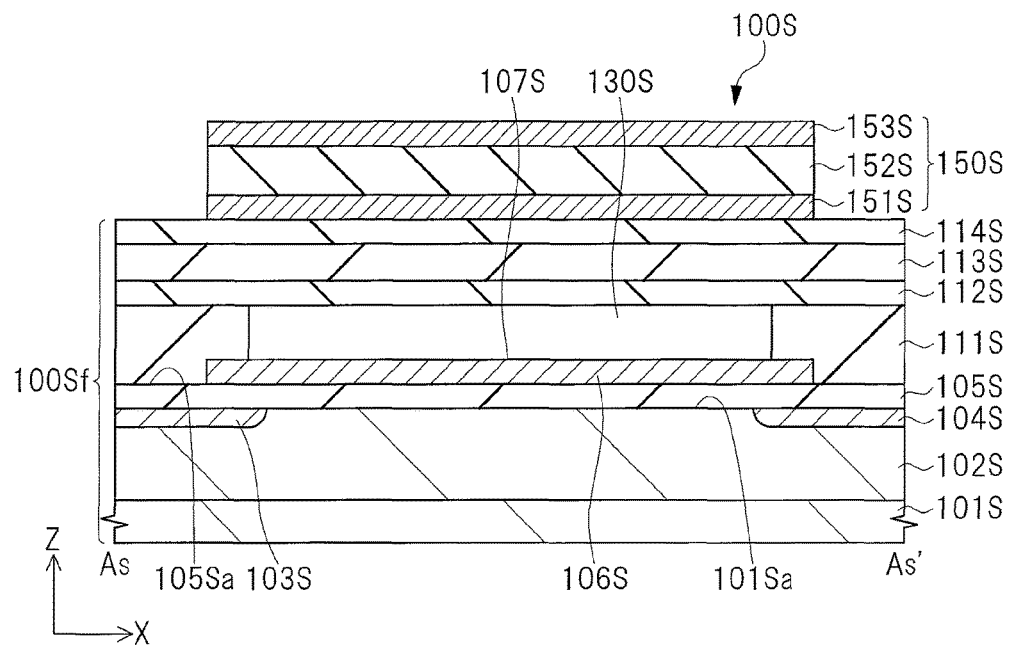
FIG. 3A is a cross-sectional view taken along a line $A_s$-$A_s'$ of a sensor FET in FIG. 2.
Figure 3B:
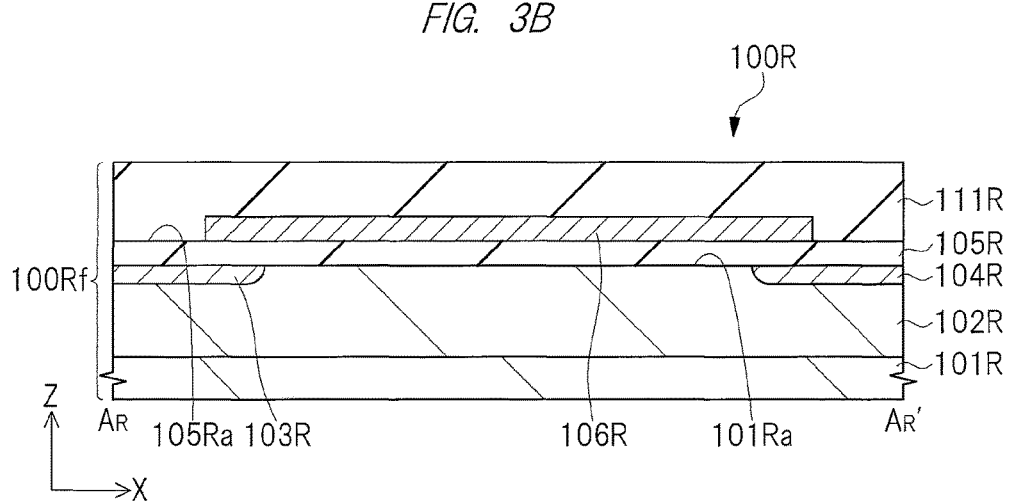
FIG. 3B is a cross-sectional view taken along a line $A_R$-$A_R'$ of a reference FET.
Figure 4A:
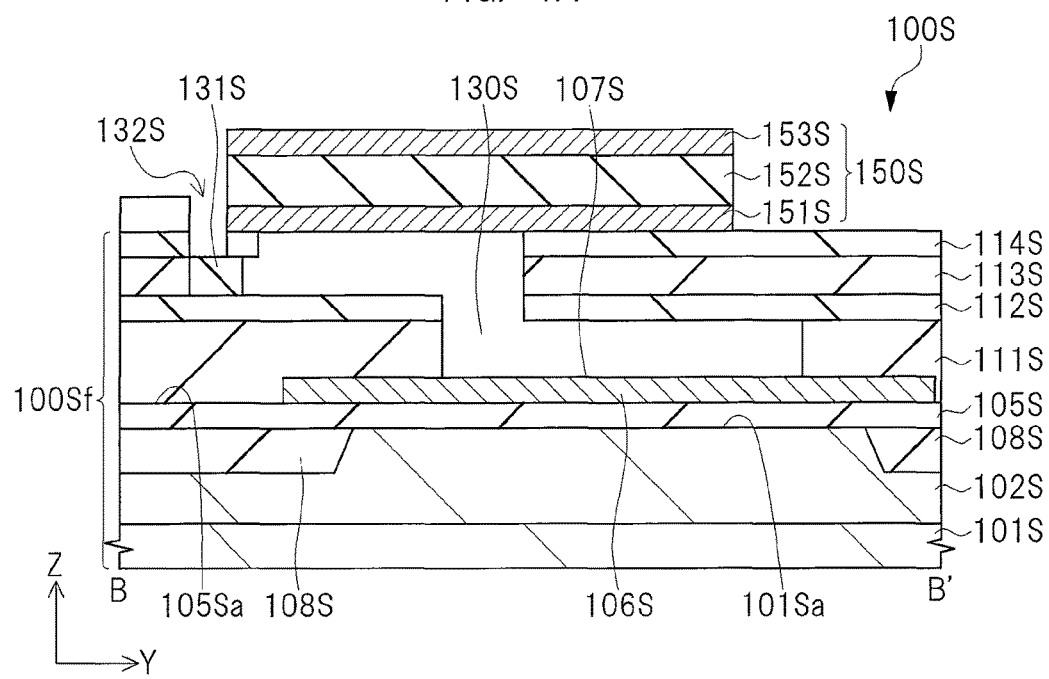
FIG. 4A is a cross-sectional view taken along a line B-B' of the sensor FET in FIG. 2.
Figure 4B:
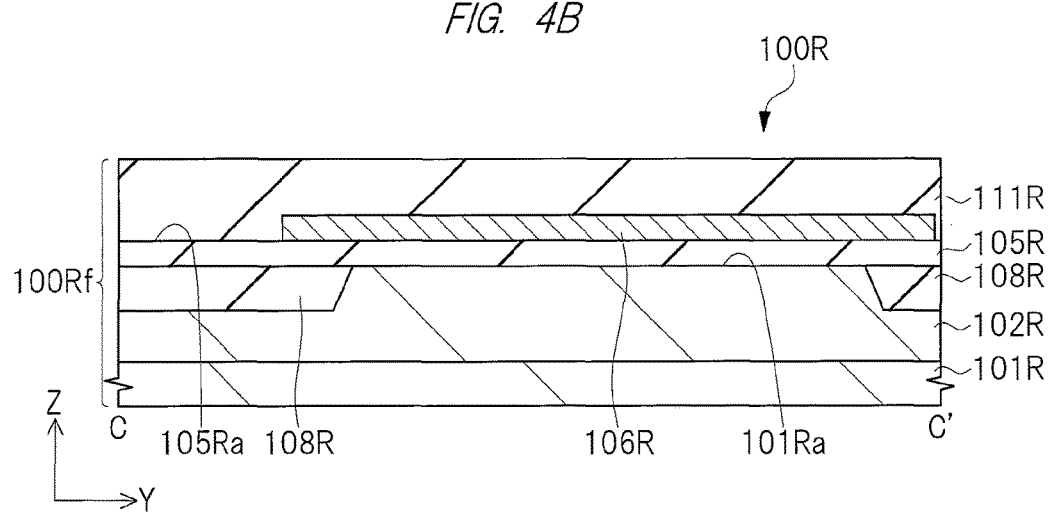
FIG. 4B is a cross-sectional view taken along a line C-C' of the reference FET.
Figure 5:
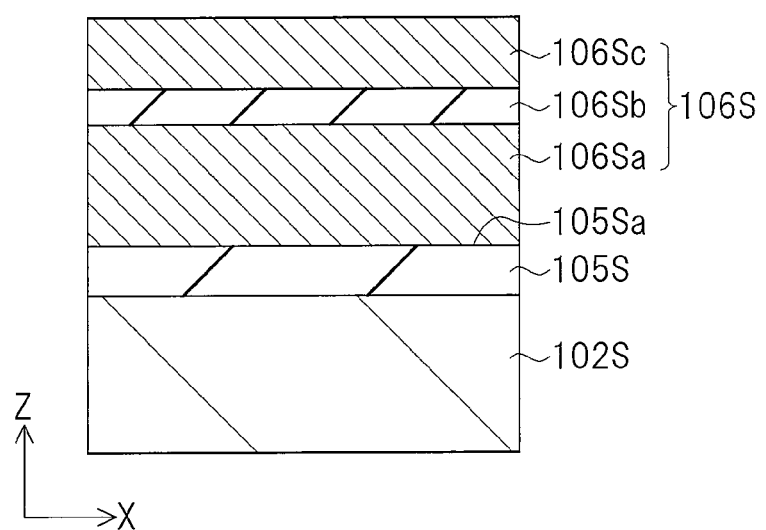
FIG. 5 is a cross-sectional view showing an example of a configuration of a gate layer of the sensor FET according to the first embodiment.
Figure 6A:
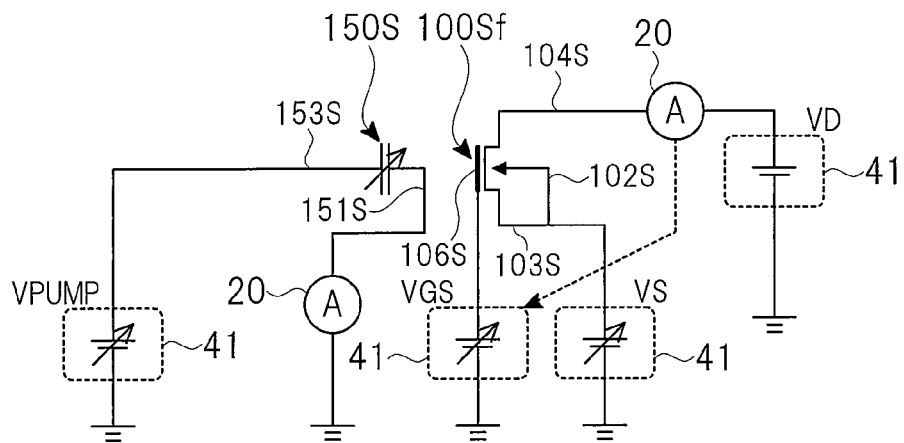
FIG. 6A is a circuit diagram showing an example of a connection structure of the sensor FET in the sensor unit according to the first embodiment.
Figure 6B:
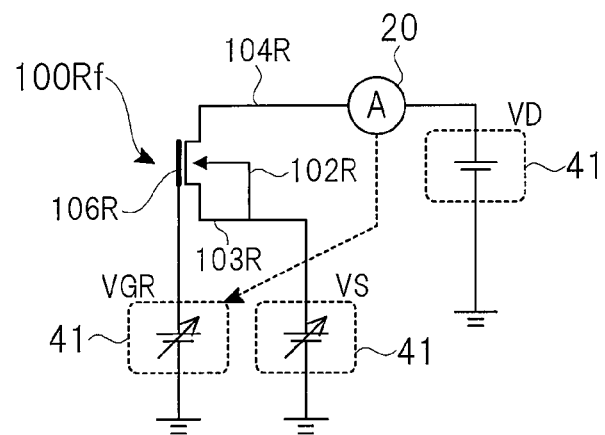
FIG. 6B is a circuit diagram showing an example of a connection structure of the reference FET in the sensor unit according to the first embodiment.
Figure 6C:
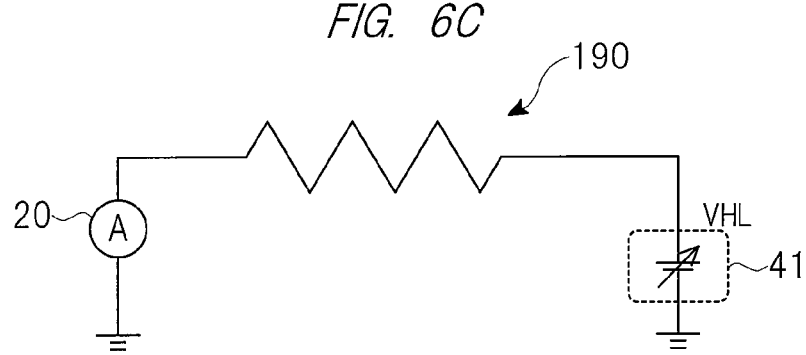
FIG. 6C is a circuit diagram showing an example of a connection structure of a heater in the sensor unit according to the first embodiment.
Figure 7A:
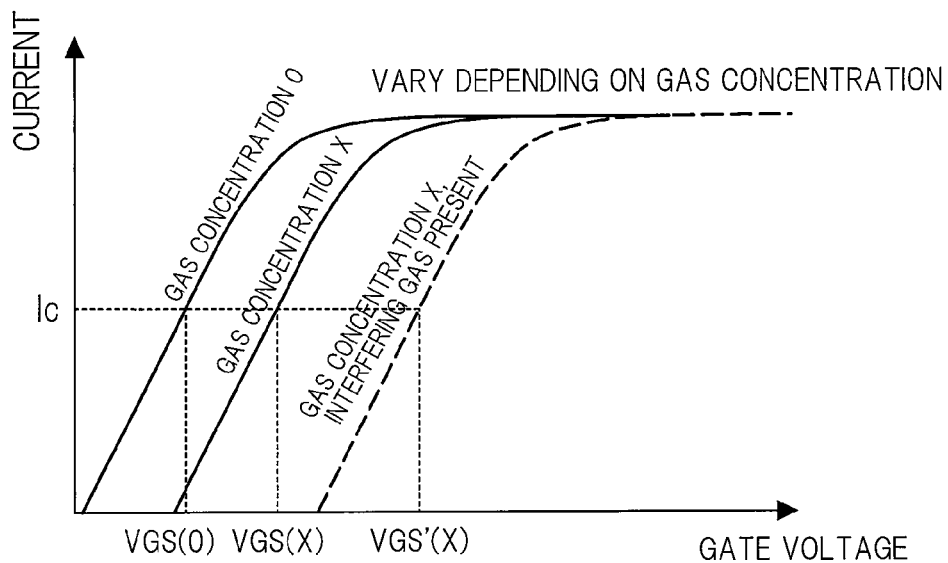
FIG. 7A is a graph showing an example of current-gate voltage characteristics of the sensor FET in the gas sensor according to the first embodiment.
Figure 7B:
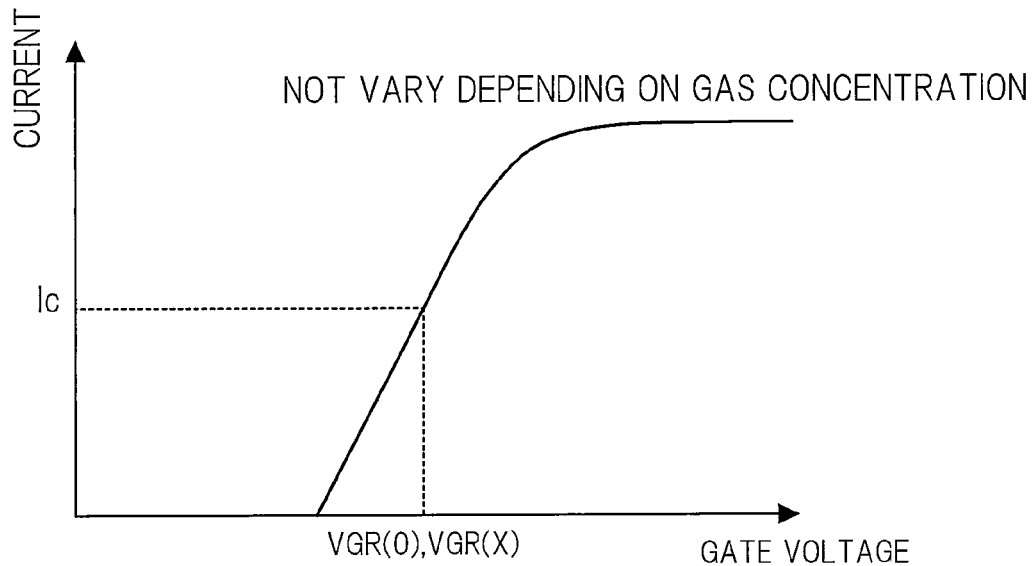
FIG. 7B is a graph showing an example of current-gate voltage characteristics of the reference FET in the gas sensor according to the first embodiment.

FIG. 1 is a schematic diagram showing an example of a configuration of the gas sensor according to the first embodiment. FIG. 2 is a plan view showing an example of a configuration of a sensor unit of the gas sensor according to the first embodiment. FIG. 3A is a cross-sectional view taken along a line $A_s$-$A_s'$ of a sensor FET in FIG. 2, and FIG. 3B is a cross-sectional view taken along a line $A_R$-$A_R'$ of a reference FET. FIG. 4A is a cross-sectional view taken along a line B-B' of the sensor FET in FIG. 2, and FIG. 4B is a cross-sectional view taken along a line C-C' of the reference FET. FIG. 5 is a cross-sectional view showing an example of a configuration of a gate layer of the sensor FET according to the first embodiment. FIG. 6A is a circuit diagram showing an example of a connection structure of the sensor FET in the sensor unit according to the first embodiment. FIG. 6B is a circuit diagram showing an example of a connection structure of the reference FET in the sensor unit according to the first embodiment. FIG. 6C is a circuit diagram showing an example of a connection structure of a heater in the sensor unit according to the first embodiment. FIG. 7A is a graph showing an example of current-gate voltage characteristics of the sensor FET in the gas sensor according to the first embodiment, and FIG. 7B is a graph showing an example of current-gate voltage characteristics of the reference FET in the gas sensor according to the first embodiment.

As shown in FIG. 1, a gas sensor 1 includes a sensor unit 100, a current measurement unit 20, a gas concentration measurement unit 30, a power supply unit 40, a control unit 50, a data input and output unit 90, and the like. The sensor unit 100 includes a sensor element 100S, a reference element 100R, a heater 190, and the like. The sensor element 100S includes a sensor FET 100Sf and an ion pump 150S, and the reference element 100R includes a reference FET 100Rf.

As shown in FIG. 2, FIG. 3A, and FIG. 4A, the sensor FET 100Sf includes a semiconductor substrate 101S, a well 102S, a source diffusion layer 103S, a drain diffusion layer 104S, agate insulation film 105S, a gate layer 106S, an insulation film 108S, and insulation films 111S to 114S serving as gas diffusion prevention films, and the like. The semiconductor substrate 101S is made of, for example, silicon (Si) or silicon carbide (SiC).

As shown in FIG. 2, FIG. 3A, and FIG. 4A, the well 102S is formed on a main surface 101Sa side of the semiconductor substrate 101S. The well 102S is a layer formed by implanting a predetermined impurity defining characteristics of the sensor FET 100Sf. The well 102S is, for example, a layer whose conductivity type is an N type or a P type. For example, the well 102S is formed so as to surround, in plan view, the source diffusion layer 103S, the drain diffusion layer 104S, the gate insulation film 105S, and the gate layer 106S.

As shown in FIG. 4A, the insulation film 108S is formed on the main surface 101Sa side of the semiconductor substrate 101S and functions as a trench isolation. The insulation film 108S defines a channel region in a channel width direction (Y direction) of the sensor FET 100Sf. Also, on the main surface 101Sa of the semiconductor substrate 101S in a region where the insulation film 108S is formed, a current does not flow regardless of voltage applied to the gate layer 106S, and the insulation film 108S suppresses defect of the FET characteristics due to leak current caused by a so-called parasitic transistor. As a method of defining the channel region in the channel width direction (Y direction), there are other methods such as a method using LOCOS (Local Oxidation of Silicon), a method using field plate isolation, a method of thickening a gate insulation film, and the like. In the first embodiment, it is also possible to use these methods.

As shown in FIG. 2 and FIG. 3A, the source diffusion layer 103S is formed on the main surface 101Sa side of the semiconductor substrate 101S and for example, is formed in a partial region of the well 102S in plan view. The source diffusion layer 103S is a layer formed by implanting a predetermined impurity defining the characteristics of the sensor FET 100Sf. For example, the source diffusion layer 103S is a layer whose conductivity type is the N type or the P type, which is different from the well 102S.

As shown in FIG. 2 and FIG. 3A, the drain diffusion layer 104S is formed on the main surface 101Sa side of the semiconductor substrate 101S and for example, is formed in a partial region of the well 102S in plan view. The drain diffusion layer 104S is a layer formed by implanting predetermined impurity defining the characteristics of the sensor FET 100Sf. For example, the drain diffusion layer 104S is a layer whose conductivity type is the N type or the P type, which is different from the well 102S.

As shown in FIG. 3A and FIG. 4A, the gate insulation film 105S is formed over the main surface 101Sa of the semiconductor substrate 101S. The gate insulation film 105S is formed so as to cover the well 102S, the source diffusion layer 103S, and the drain diffusion layer 104S in plan view. More specifically, the gate insulation film 105S electrically insulates the well 102S, the source diffusion layer 103S, and the drain diffusion layer 104S, from the gate layer 106S. The gate insulation film 105S is made of, for example, silicon dioxide ($SiO_2$) or the like.

As shown in FIG. 3A and FIG. 4A, the gate layer 106S is formed over an upper surface 105Sa of the gate insulation film 105S. Specifically, the gate layer 106S is formed to cover, for example, a partial region of the source diffusion layer 103S, a partial region of the well 102S, and a partial region of the drain diffusion layer 104S. More specifically, the gate layer 106S is formed in a partial region of the source diffusion layer 103S on a side of the drain diffusion layer 104S, a region of the well 102S between the source diffusion layer 103S and the drain diffusion layer 104S, and a partial region of the drain diffusion layer 104S on a side of the source diffusion layer 103S.

Also, as shown in FIG. 5, for example, the gate layer 106S has a configuration in which a first metal oxide layer 106Sa, a second metal oxide layer 106Sb, and an electrode layer 106Sc are laminated from the upper surface 105Sa of the gate insulation film 105S. The first metal oxide layer 106Sa is made of, for example, zirconia ($ZrO_2$) to which yttria ($Y_2O_3$) or the like is added. The second metal oxide layer 106Sb is made of, for example, nickel oxide (NiO) or tungsten oxide ($WO_3$). The electrode layer 106Sc is made of, for example, platinum (Pt), rhodium (Rh), or palladium (Pd). In the electrode layer 106Sc, gas decomposition or ionization such as oxygen, nitrogen oxide, or hydrogen is performed. Even in the second metal oxide layer 106Sb, depending on a combination of the detection target gas and the metal oxide material, gas is decomposed or ionized. The ionized oxygen or hydrogen moves to the first metal oxide layer 106Sa.

As shown in FIG. 3A and FIG. 4A, the insulation films 111S to 114S serving as gas diffusion prevention films are formed in the upper layers of the gate insulation film 105S and the gate layer 106S. The insulation film 111S and the insulation film 113S are made of, for example, silicon dioxide ($SiO_2$). The insulation film 112S and the insulation film 114S are made of, for example, silicon nitride (SiN).

A part of a front surface of the gate layer 106S is covered with the insulation film 111S. In the remaining portion (an exposed portion 107S) of the gate layer 106S, the insulation film 111S is removed, and the front surface of the gate layer 106S is exposed to be in contact with a cavity 130S. A periphery of the cavity 130S is covered with the gate layer 106S, the insulation films 111S to 114S, and the ion pump 150S. The cavity 130S is connected to the atmosphere via a gas introduction portion 132S having a gas diffusion resistance film 131S.

As shown in FIG. 3A and FIG. 4A, the ion pump 150S is provided with an ion pump electrode 151S, an ion conductive film 152S, and an ion pump electrode 153S. More specifically, the ion conductive film 152S and the ion pump electrode 153S are laminated over the ion pump electrode 151S. The ion pump electrode 151S, the ion conductive film 152S, and the ion pump electrode 153S form the ion pump 150S. In other words, the ion pump electrode 151S is formed in contact with a lower surface of the ion conductive film 152S. The ion pump electrodes 151S and 153S are made of, for example, platinum (Pt), rhodium (Rh), or palladium (Pd). The ion conductive film 152S is made of, for example, zirconia ($ZrO_2$) to which yttria ($Y_2O_3$) or the like is added.

By applying voltage between the ion pump electrode 151S and the ion pump electrode 153S, the ion pump 150S can flow ion current. For example, when zirconia ($ZrO_2$) to which yttria ($Y_2O_3$) is added is used as the ion conductive film 152S, the ion conductive film 152S becomes an oxygen ion conductor. When a negative voltage with reference to the ion pump electrode 153S is applied to the ion pump electrode 151S, the oxygen molecules ($O_2$) are decomposed into oxygen ions ($O^{2-}$) on a lower surface of the ion pump electrode 151S, and the oxygen ions ($O^{2-}$) move toward the ion pump electrode 153S via the ion conductive film 152S. The oxygen ions ($O^{2-}$) that have moved to the ion pump electrode 153S pass electrons to the ion pump electrode 153S to become neutral to be oxygen molecule. Then, the oxygen molecules are released from an upper surface of the ion pump electrode 153S.

Also, when a hydrogen ion conductor is used for the ion conductive film 152S and a positive voltage with reference to the ion pump electrode 153S is applied to the ion pump electrode 151S, hydrogen molecules ($H_2$) are decomposed into hydrogen ions ($H^+$) on the lower surface of ion pump electrode 151S. The hydrogen ions ($H^+$) move toward the ion pump electrode 153S via the ion conductive film 152S. The hydrogen ions ($H^+$) that have moved to the ion pump electrode 153S take electrons from the ion pump electrode 153S to become neutral to be hydrogen molecules. The hydrogen molecules are released from the upper surface of the ion pump electrode 153S.

The well 102S, the source diffusion layer 103S, the drain diffusion layer 104S, and the gate layer 106S constituting the sensor FET 100Sf are connected to the power supply unit 40, the current measurement unit 20, and the like shown in FIG. 1 via a wiring layer (not shown) made of a metal such as titanium (Ti), tungsten (W), tungsten nitride (WN), titanium nitride (TiN), or platinum (Pt), for example.

As showing in FIG. 6A, the well 102S and the source diffusion layer 103S constituting the sensor FET 100Sf are connected to a power supply 41 applying a variable voltage VS. The drain diffusion layer 104S is connected to the power supply 41 which applies a constant voltage VD. The drain diffusion layer 104S is also connected to the current measurement unit 20. The gate layer 106S is connected to the power supply 41 which applies a variable voltage VGS. The ion pump electrode 151S is connected to the current measurement unit 20. Further, the ion pump electrode 153S is connected to the power supply 41 that applies a voltage VPUMP operating the ion pump 150S.

FIG. 7A is a graph showing an example of current-gate voltage characteristics of the sensor FET 100Sf. When gas (e.g., nitrogen oxide gas) comes into contact with the gate layer 106S (for example, see FIG. 2, FIG. 3A, and FIG. 4A), work function of the gate layer 106S changes. Then, as shown in FIG. 7A, the current-gate voltage characteristics of the sensor FET 100Sf shift in parallel in the right direction in the figure depending on the gas concentration. That is, threshold voltage of the gate layer 106S in the case where a threshold current Ic flows in the drain diffusion layer 104S (for example, see FIG. 2 and FIG. 3A) increases as the gas concentration increases.

As shown in FIG. 2, FIG. 3B, and FIG. 4B, the reference FET 100Rf includes a semiconductor substrate 101R, a well 102R, a source diffusion layer 103R, a drain diffusion layer 104R, a gate insulation film 105R, a gate layer 106R, an insulation film 108R, an insulation film 111R, and the like.

Many of the components constituting the reference FET 100Rf are the same as those of the sensor FET 100Sf described above. For example, the semiconductor substrate 101R, the well 102R, the source diffusion layer 103R, the drain diffusion layer 104R, the gate insulation film 105R, the gate layer 106R, the insulation film 108R, and the insulation film 111R of the reference FET 100Rf have the same configurations as those of the semiconductor substrate 101S, the well 102S, the source diffusion layer 103S, the drain diffusion layer 104S, the gate insulation film 105S, the gate layer 106S, the insulation film 108S, and the insulation film 11S, respectively, of the sensor FET 100Sf. For this reason, a detailed description thereof will be omitted.

As shown in FIG. 2, FIG. 3B, and FIG. 4B, in the reference FET 100Rf, no insulation film is laminated over the insulation film 111R. However, the insulation films 112S to 114S, the ion pump electrode 151S, the ion conductive film 152S, and the ion pump electrode 153S laminated over the insulation film 111S in the sensor FET 100Sf may be laminated over the insulation film 111R.

As shown in FIG. 3B and FIG. 4B, the insulation film 111R serving as a gas diffusion prevention film is formed over an upper surface 105Ra of the gate insulation film 105R so as to cover an upper surface and a side surface of the gate layer 106R. That is, the gate layer 106R is isolated from the atmosphere.

The well 102R, the source diffusion layer 103R, the drain diffusion layer 104R, and the gate layer 106R constituting the reference FET 100Rf are connected to the power supply unit 40, the current measurement unit 20, and the like shown in FIG. 1 via a wiring layer (not shown) made of a metal such as titanium (Ti), tungsten (W), tungsten nitride (WN), titanium nitride (TiN), or platinum (Pt), for example.

As shown in FIG. 6B, the well 102R and the source diffusion layer 103R constituting the reference FET 100Rf are connected to the power supply 41 which applies the variable voltage VS. The drain diffusion layer 104R is connected to the power supply 41 which applies the constant voltage VD. Further, the drain diffusion layer 104R is connected to the current measurement unit 20. The gate layer 106R is connected to the power supply 41 which applies the variable voltage VGR.

FIG. 7B is a graph showing an example of current-gate voltage characteristics of the reference FET 100Rf. Since the gate layer 106R (for example, see FIG. 2, FIG. 3B, and FIG. 4B) is covered with the insulation film 111R (for example, see FIG. 3B and FIG. 4B) serving as the gas diffusion prevention film, the gate layer 106R does not adsorb gases, and work function of the gate layer 106R does not change. Therefore, the current-gate voltage characteristics of the reference FET 100Rf do not vary depending on the gas concentration.

Note that, in the following description, it is assumed that the sensor FET 100Sf and the reference FET 100Rf are constituted by an N type FET. However, both may be constituted by the P type. Alternatively, one of the sensor FET 100Sf and the reference FET may be constituted by the N type, and the other of the sensor FET 100Sf and the reference FET may be constituted by the P type.

As shown in FIG. 1, the heater 190 is connected to the power supply unit 40, and generates a Joule heat by having a voltage applied across both ends, and adjusts a temperature of the sensor unit 100 with the generated Joule heat. For example, the heater 190 is constituted by a wiring made of a metal such as titanium (Ti), tungsten (W), tungsten nitride (WN), titanium nitride (TiN), or platinum (Pt).

Also, as shown in FIG. 6C, one end of the heater 190 is grounded, and the other end of the heater 190 is connected to the power supply 41 which applies a voltage VHL. The heater 190 also functions as a sensor thermometer measuring the temperature of the sensor unit 100 (for example, see FIG. 1). For example, at this time, the heater 190 is connected to the current measurement unit 20.

The sensor FET 100Sf and the reference FET 100Rf may be formed in different semiconductor substrates or may be formed in the same semiconductor substrate. Also, the heater 190 may be formed integrally with the sensor FET 100Sf or the reference FET 100Rf, or may be configured separately from the sensor FET 100Sf or the reference FET 100Rf.

As shown in FIG. 1, the current measurement unit 20 measures the current of the sensor FET 100Sf and the current of the reference FET 100Rf. For example, the current measurement unit 20 measures a first source-drain current flowing between the source diffusion layer 103S and the drain diffusion layer 104S (for example, see FIG. 2 and FIG. 3A) of the sensor FET 100Sf. In addition, for example, the current measurement unit 20 measures the ion current flowing between the ion pump electrode 151S and the ion pump electrode 153S (for example, see FIG. 3A and FIG. 4A) of the sensor FET 100Sf. For example, the current measurement unit 20 measures a second source-drain current flowing between the source diffusion layer 103R and the drain diffusion layer 104R (for example, see FIG. 2 and FIG. 3B) of the reference FET 100Rf. The current measurement unit 20 outputs the measured current data of the sensor FET 100Sf and the current data of the reference FET 100Rf to the control unit 50.

In addition, the current measurement unit 20 measures the current of the heater 190. The current measurement unit 20 outputs the measured current data of the heater 190 to the control unit 50.

The gas concentration measurement unit 30 measures the gas concentration of the detection target gas in the atmosphere. For example, in the case where the detection target gas and the interfering gas are not present in the atmosphere, the voltage applied to the gate layer 106R (for example, see FIG. 6B) when the second source-drain current flowing in the reference FET is the predetermined threshold current Ic is defined as the threshold voltage VGR(0). Also, the voltage applied to the gate layer 106S (for example, see FIG. 6A) when the first source-drain current flowing through the sensor FET is the predetermined threshold current Ic is defined as the threshold voltage VGS(0). A difference between the threshold voltage VGR(0) and the threshold voltage VGS(0) is defined as a potential difference between the sensors VGRS(0) (=VGR(0)−VGS(0)).

Also, in the case where the detection target gas is present in the atmosphere, the voltage applied to the gate layer 106R (for example, see FIG. 6B) when the second source-drain current flowing in the reference FET is the predetermined threshold current Ic at a predetermined time is defined as the threshold voltage VGR(X) (=VGR(0)). Also, the voltage applied to the gate layer 106S (for example, see FIG. 6A) when the first source-drain current flowing through the sensor FET is the predetermined threshold current Ic is defined as the threshold voltage VGS(X). A difference between the threshold voltage VGR(X) and the threshold voltage VGS(X) is defined as a potential difference between the sensors VGRS(X) (=VGR(X)−VGS(X)).

Then, the gas concentration of the detection target gas at a predetermined time is measured based on a threshold value change amount ΔVg(X) (=VGRS(X)−VGRS(0)) which is a difference between the potential difference between the sensors VGRS(0) (=VGR(0)−VGS(0)) and the potential difference between the sensors VGRS(X) (=VGR(X)−VGS(X)).

As shown in FIG. 1, the power supply unit 40 supplies power supply to each unit constituting the gas sensor 1. The power supply unit 40 includes a plurality of power supplies 41. The power supply unit 40 is constituted by, e.g., a power supply 41 which applies a constant voltage, a power supply 41 that applies a variable voltage, and a power supply 41 that applies a periodically varying voltage. The number of power supplies 41 is not limited to the number (four) shown in FIG. 1.

As shown in FIG. 1, the control unit 50 controls each unit constituting the gas sensor 1.

For example, the control unit 50 performs control relating to switching on and off of each unit.

Based on the current data output from the current measurement unit 20, the control unit 50 also controls the power supply 41 connected to the gate layer 106S of the sensor FFT 100Sf (for example, see FIG. 6A). The control unit 50 adjusts the voltage of the power supply 41 such that the current of the drain diffusion layer 104S of the sensor FET 100Sf becomes the predetermined threshold current Ic in measuring the gas concentration (for example, see FIG. 6A and FIG. 7A). Based on the current of the ion pump 150S output from the current measurement unit 20, the control unit 50 controls the voltage VPUMP supplied to the ion pump 150S by the power supply 41 (for example, see FIG. 6A).

Based on the current data output from the current measurement unit 20, the control unit 50 also controls the power supply 41 connected to the gate layer 106R of the reference FET 100Rf (for example, see FIG. 6B). The control unit 50 adjusts the voltage of the power supply 41 such that the current of the drain diffusion layer 104R of the reference FET 100Rf becomes the predetermined threshold current Ic in measuring the gas concentration (for example, see FIG. 6B and FIG. 7B).

Based on the current data of the heater 190 output from the current measurement unit 20, the control unit 50 also measures the temperature of the sensor FET 100Sf and the temperature of the reference FET 100Rf. From the voltage across the heater 190 and the current data of the heater 190, the control unit 50 calculates a resistance value of the heater 190. Then, for example, the control unit 50 measures the temperature by referring to temperature data associating the resistance value and the temperature. The control unit 50 controls the power supply 41 connected to the heater 190. More specifically, the control unit 50 adjusts the voltage of the power supply 41 such that the temperature of the sensor FET 100Sf and the temperature of the reference FET 100Rf are constant in measuring the gas concentration.

As shown in FIG. 1, the data input and output unit 90 inputs and outputs data with an external apparatus connected to the gas sensor 1. The gas sensor 1 receives input of various data output from the external apparatus via the data input and output unit 90. In addition, the gas sensor 1 outputs data on the measured gas concentration, the temperature, and the like to the external apparatus via the data input and output unit 90.

The data input and output unit 90 may be connected to the external apparatus by wired connection or may be connected to the external apparatus by infrared communication or near field wireless communication. Also, the data input and output unit 90 may be connected to the external apparatus via a network.

<Measurement Method of Gas Concentration>

Next, a measurement method of gas concentration using the gas sensor according to the first embodiment will be described with reference to FIG. 1, FIG. 2, FIG. 6A, and FIG. 6B. In the following, a description will be given of a case where nitrogen oxide gas is exemplified as a detection target gas, oxygen gas is exemplified as an interfering gas, and the gas concentration of nitrogen oxide gas is measured.

First, the control unit 50 adjusts the temperature of the sensor unit 100. For example, the control unit 50 applies a voltage across both of the ends of the heater 190 by turning on the power supply 41 connected to the heater 190.

Next, the control unit 50 turns on the power supply 41 connected to each unit of the sensor FET 100Sf and the reference FET 100Rf. Then, the power supply 41 applies a predetermined voltage to each unit of the sensor FET 100Sf and the reference FET 100Rf.

For example, the power supply 41 connected to the well 102S and the source diffusion layer 103S of the sensor FET 100Sf applies the voltage of the variable voltage VS (for example, 0 V). Also, the power supply 41 connected to the drain diffusion layer 104S applies a constant voltage VD. Also, the power supply 41 connected to the gate layer 106S applies a predetermined threshold voltage VGS(0) such that the first source-drain current becomes the threshold current Ic. The voltage VPUMP is applied to the ion pump 150S such that the ion pump electrode 151S on the lower side of the ion pump 150S becomes a negative voltage with respect to the ion pump electrode 153S on the upper side.

Also, the power supply 41 connected to the well 102R and the source diffusion layer 103R of the reference FET 100Rf applies the voltage of the variable voltage VS (for example, 0 V). Also, the power supply 41 connected to the drain diffusion layer 104R applies the constant voltage VD. Also, the power supply 41 connected to the gate layer 106R applies the predetermined threshold voltage VGR(0) such that the second source-drain current becomes the threshold current Ic.

Note that the threshold voltage VGS(0) of the sensor FET 100Sf and the threshold voltage VGR(0) of the reference FET 100Rf in the case where the gas concentration is 0 may be measured in advance. For example, the control unit 50 may read the data of the threshold voltages VGS(0) and VGR(0) which have been measured in advance as needed from a data storage unit (not shown). The control unit 50 outputs the data of the threshold voltages VGS(0) and VGR(0) to the gas concentration measurement unit 30, for example.

Next, the control unit 50 measures the threshold voltage VGS(X) of the sensor FET 100Sf and the threshold voltage VGR(X) of the reference FET 100Rf in the case where the nitrogen oxide gas is contained in the atmosphere. The control unit 50 adjusts the voltage of the power supply 41 connected to the gate layers 106S and 106R while referring to the current data output from the current measurement unit 20, for example, thereby measuring the threshold voltages VGS(X) and VGR(X). Note that, since the gate layer 106R of the reference FET 100Rf is isolated from the atmosphere by the insulation film 111R (for example, see FIG. 3B and FIG. 4B), the threshold voltage VGR(X) of the reference FET 100Rf is the same as the threshold voltage VGR(0) when the gas concentration is 0.

The control unit 50 outputs respective data of the measured threshold voltages VGS(X) and VGR(X) to the gas concentration measurement unit 30, for example.

Even when the oxygen gas is contained as an interfering gas in the atmosphere, the gas concentration of the oxygen gas in the cavity 130S (for example, see FIG. 3A and FIG. 4A) can be sufficiently reduced by the ion pump 150S so as not to affect the threshold voltage VGS(X). The gas in the atmosphere is introduced into the cavity 130S via the gas diffusion resistance film 131S (for example, see FIG. 4A). From the gas in the atmosphere, the oxygen gas is removed by the ion pump 150S, and the gas comes into contact with the sensor FET 100Sf having the gate layer 106S exposed to the cavity 130S.

When the nitrogen oxide gas is contained in the gas in the atmosphere, the threshold voltage VGS(X) changes according to the concentration of the nitrogen oxide gas. For example, in the case of exhaust gas of engine automobiles, nitrogen oxide gas often contains both nitrogen monoxide (NO) and nitrogen dioxide ($NO_2$) When the above voltage is applied to the ion pump 150S, nitrogen dioxide ($NO_2$) is converted into nitrogen monoxide (NO). In the sensor FET 100Sf having the gate layer 106S, the gas concentration of nitrogen monoxide (NO) gas in the gas in which oxygen is removed to convert nitrogen dioxide ($NO_2$) into nitrogen monoxide (NO), of the mixed gas of nitrogen monoxide (NO) and nitrogen dioxide ($NO_2$), is measured.

Next, based on the threshold voltages VGS(0), VGR(0), VGS(X), and VGR(X) output from the control unit 50, the gas concentration measurement unit 30 calculates the threshold value change amount of the sensor FET 100Sf. For example, the gas concentration measurement unit 30 calculates the threshold value change amount of the sensor FET 100Sf from the difference between the potential difference VGRS(0) between the sensor FET 100Sf and the reference FET 100Rf when there is no nitrogen oxide gas in the atmosphere and the potential difference VGRS(X) between the sensor FET 100Sf and the reference FET 100Rf when there is nitrogen oxide gas in the atmosphere. That is, the threshold value change amount $\Delta Vg(X)$ of the sensor FET 100Sf is expressed as follows.

$$\Delta Vg(X) = VGRS(0) - VGRS(X) \quad \text{(Expression 1)}$$

The threshold value change amount indicated in (Expression 1) is made in view of the threshold voltages VGR(0) and VGR(X) of the reference FET 100Rf. This is to suppress the influence of the noise generated in the sensor unit 100 due to temperature change and the like.

Note that, when the variations of the threshold voltages VGS(0) and VGS(X) due to noise are small, the gas concentration measurement unit 30 may measure the gas concentration using only the sensor FET 100Sf. In this case, the gas concentration measurement unit 30 measures the gas concentration of the nitrogen oxide gas at a predetermined time on the basis of the threshold value change amount Vg(X) which is the difference between the threshold voltage VGS(0) applied to the gate layer 106S when there is no nitrogen oxide gas in the atmosphere and the threshold voltage VGS(X) applied to the gate layer 106S when there is nitrogen oxide gas in the atmosphere, and a time derivative of the threshold value change amount Vg(X). Here, the threshold voltage VGS(0) is the voltage applied to the gate layer 106S when the first source-drain current becomes the predetermined threshold current Ic in the case where there is no nitrogen oxide gas in the atmosphere. Also, the threshold voltage VGS(X) is the voltage applied to the gate layer 106S when the first source-drain current becomes the predetermined threshold current Ic at a predetermined time in the case where there is nitrogen oxide gas in the atmosphere.

Therefore, the threshold value change amount ΔVg(X) in this case is expressed as follows.

$$\Delta Vg(X) = VGS(0) - VGS(X) \quad \text{(Expression 2)}$$

<First Modification Example of Work Function Type Element>

Figure 8A:
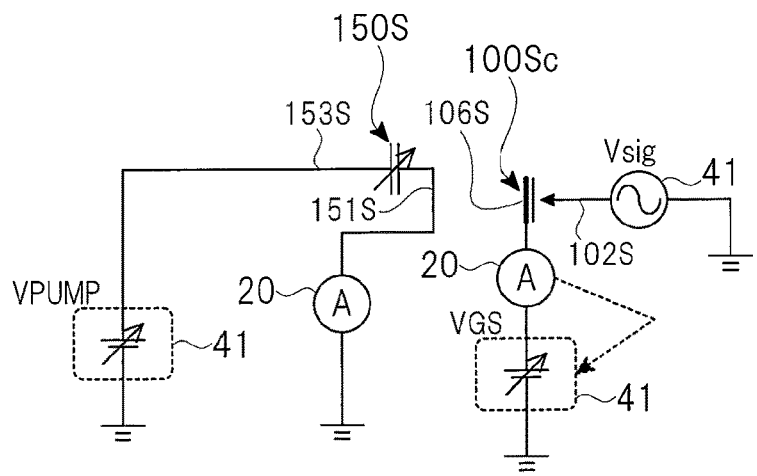
FIG. 8A is a circuit diagram showing an example of a connection structure of a sensor capacitor in the sensor unit according to a first modification example of the first embodiment.
Figure 8B:
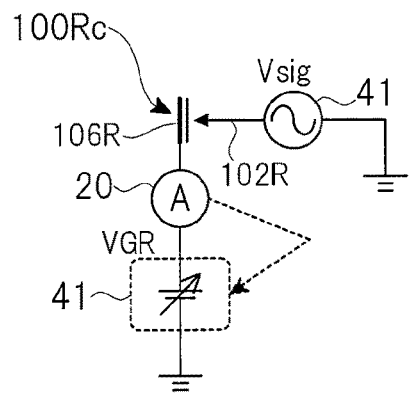
FIG. 8B is a circuit diagram showing an example of a connection structure of a reference capacitor in the sensor unit according to the first modification example of the first embodiment.
Figure 8C:
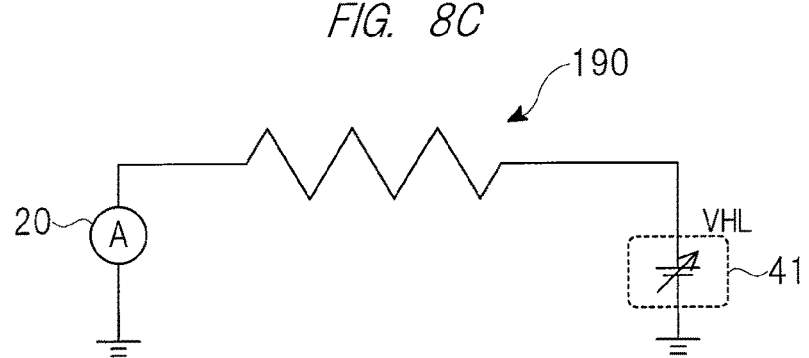
FIG. 8C is a circuit diagram showing an example of a connection structure of a heater in the sensor unit according to the first modification example of the first embodiment.
Figure 9A:
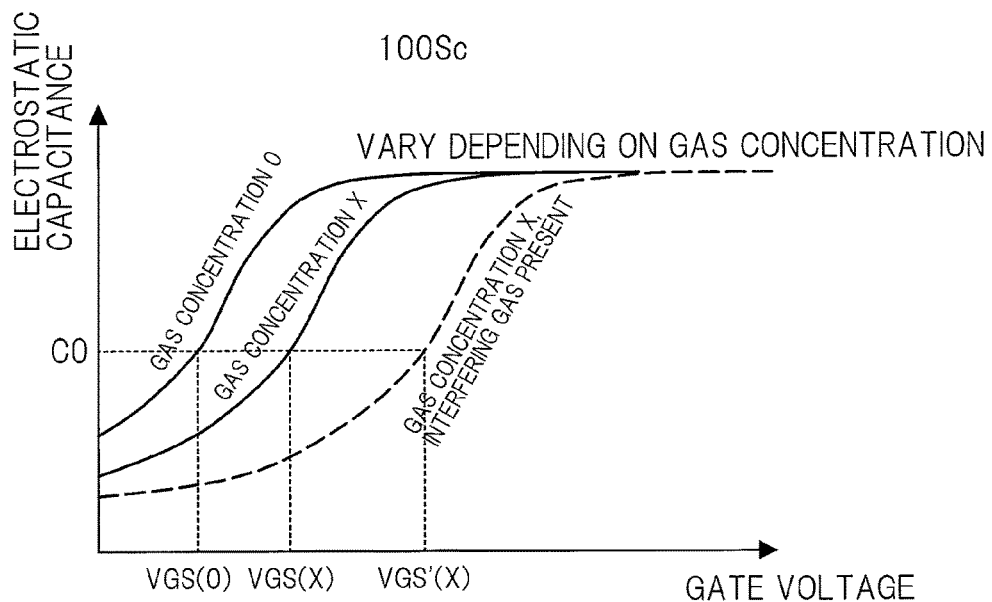
FIG. 9A is a graph showing an example of electrostatic capacitance-gate voltage characteristics of a sensor capacitor in a gas sensor according to the first modification example of the first embodiment.
Figure 9B:
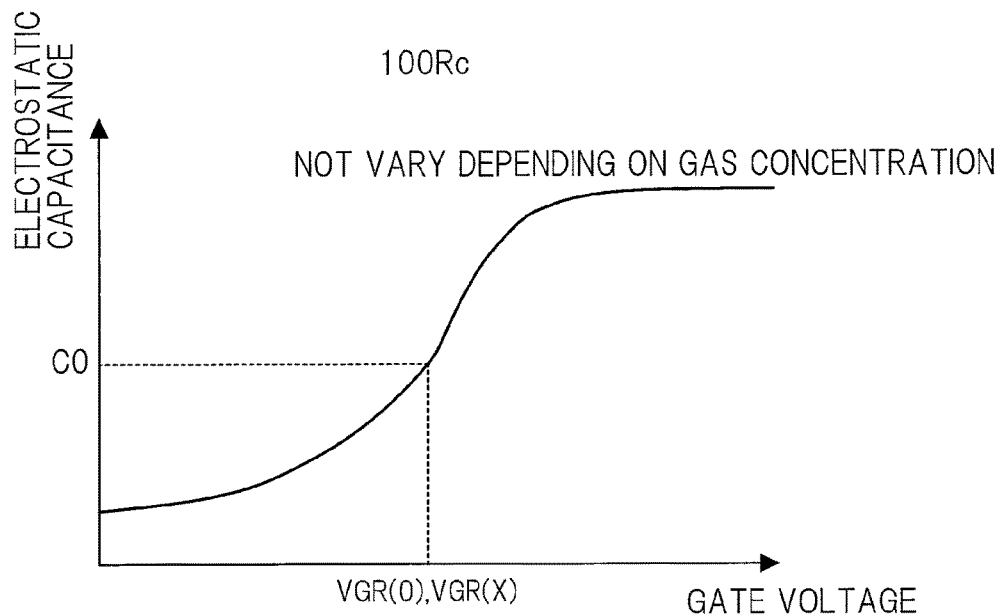
FIG. 9B is a graph showing an example of electrostatic capacitance-gate voltage characteristics of a reference capacitor in the gas sensor according to the first modification example of the first embodiment.

A work function type sensor according to a first modification example of the first embodiment will be described with reference to FIG. 8 and FIG. 9. FIG. 8A is a circuit diagram showing an example of a connection structure of a sensor capacitor in the sensor unit according to the first modification example of the first embodiment. FIG. 8B is a circuit diagram showing an example of a connection structure of a reference capacitor in the sensor unit according to the first modification example of the first embodiment. FIG. 8C is a circuit diagram showing an example of a connection structure of a heater in the sensor unit according to the first modification example of the first embodiment. FIG. 9A is a graph showing an example of electrostatic capacitance-gate voltage characteristics of a sensor capacitor in a gas sensor according to the first modification example of the first embodiment. FIG. 9B is a graph showing an example of electrostatic capacitance-gate voltage characteristics of a reference capacitor in the gas sensor according to the first modification example of the first embodiment.

In the gas sensor according to the first modification example, a sensor capacitor 100Sc is used for the sensor element 100S, and a reference capacitor 100Rc is used for the reference element 100R. The sensor capacitor 100Sc and the reference capacitor 100Rc can use substantially the same device structure and gate layer structure shown in FIG. 2 to FIG. 5.

In the sensor capacitor 100Sc, the gas concentration can be detected by utilizing the phenomenon in which the gate voltage dependence of capacitance between the gate layer 106S and the well 102S or capacitance between the gate layer 106S and the source diffusion layer 103S or between the gate layer 106S and the drain diffusion layer 104S changes depending on the gas concentration of the detection target gas.

In the reference capacitor 100Rc, the gate layer 106R is covered with the insulation film 111R (for example, see FIG. 3B and FIG. 4B). Therefore, in the reference capacitor 100Rc, even if the gas concentration of the detection target gas in the atmosphere changes, the gate voltage dependence of capacitance does not change.

In the case where the capacitance between the gate layer 106S and the well 102S is used, the source diffusion layer 103S and the drain diffusion layer 104S (for example, see FIG. 2 and FIG. 3A) can be omitted from the device structure of the sensor capacitor 100SC. Correspondingly, in the reference capacitor 100Rc, in the case where the capacitance between the gate layer 106R and the well 102R is used, the source diffusion layer 103R and the drain diffusion layer 104R (for example, see FIG. 2 and FIG. 3B) can be omitted from the device structure of the reference capacitor 100Rc.

Since the source diffusion layers 103S and 103R and the drain diffusion layers 104S and 104R can be omitted from the device structure, the number of manufacturing steps of the sensor element 100S and the reference element 100R can be reduced.

Hereinafter, the sensor capacitor 100Sc in which the source diffusion layer 103S and the drain diffusion layer 104S are removed from the sensor FET 100Sf shown in FIG. 2, FIG. 3A, and FIG. 4A, and the reference capacitor 100Rc in which the source diffusion layer 103R and the drain diffusion layer 104R are omitted from the reference FET 100Rf shown in FIG. 2, FIG. 3B, and FIG. 4B will be described. The device structure of the sensor capacitor 100Sc is obtained only by omitting the source diffusion layer 103S and the drain diffusion layer 104S from the device structure of the sensor FET 100Sf shown in FIG. 2, FIG. 3A, and FIG. 4A, and therefore, detailed description about the device structure of the sensor capacitor 100Sc is omitted. Likewise, the device structure of the reference capacitor 100Rc is obtained only by omitting the source diffusion layer 103R and the drain diffusion layer 104R from the device structure of the reference FET 100Rf shown in FIG. 2, FIG. 3B, and FIG. 4B, and therefore, detailed description about the device structure of the reference capacitor 100Rc is omitted.

Note that, in the following description, it is assumed that the conductivity types of the wells 102S and 102R are configured as the N type. However, the conductivity types of the wells 102S and 102R may be configured as the P type. Alternatively, one of the wells 102S and 102R may be configured as the N type, and the other of the wells 102S and 102R may be configured as the P type.

As shown in FIG. 8A and FIG. 8B, for example, each of the well 102S of the sensor capacitor 100SC and the well 102R of the reference capacitor 100Rc is connected to the power supply 41 which applies an alternating voltage whose voltage periodically changes like a sinusoidal wave.

The gate layer 106S of the sensor capacitor 100Sc is connected to the power supply 41 which applies the variable voltage VGS. The gate layer 106R of the reference capacitor 100Rc is connected to the power supply 41 which applies the variable voltage VGR. Also, each of the gate layer 106S of the sensor capacitor 100Sc and the gate layer 106R of the reference capacitor 100Rc is connected to the current measurement unit 20.

As shown in FIG. 8A, the ion pump electrode 151S is connected to the current measurement unit 20. Also, the ion pump electrode 153S is connected to the power supply 41 which applies the voltage VPUMP operating the ion pump 150S.

Based on the voltage applied to the gate layer 106S, the voltage applied to the well 102S (for example, alternating voltage), and the current flowing in the gate layer 106S (for example, alternating current), the electrostatic capacitance of the sensor capacitor 100Sc is measured. Also, based on the voltage applied to the gate layer 106R, the voltage applied to the well 102R (for example, alternating voltage), and the current flowing in the gate layer 106R (for example, alternating current), the electrostatic capacitance of the reference capacitor 100Rc is measured. For example, these electrostatic capacitances are measured by the gas concentration measurement unit 30 (for example, see FIG. 1) or the like.

The current measurement unit 20 measures the current flowing in the gate layer 106S of the sensor capacitor 100Sc, for example. Also, the current measurement unit 20 measures the current flowing in the gate layer 106R of the reference capacitor 100Rc, for example.

For example, based on the voltage applied to the gate layer 106S, the voltage applied to the well 102S (for example, alternating voltage), and the current flowing in the gate layer 106S (for example, alternating current), the electrostatic capacitance of the sensor capacitor 100Sc is measured by the gas concentration measurement unit 30 shown in FIG. 1.

Also, for example, based on the voltage applied to the gate layer 106R, the voltage applied to the well 102R (for example, alternating voltage), and the current flowing to the gate layer 106R (for example, alternating current), the electrostatic capacitance of the reference capacitor 100Rc is measured by the gas concentration measurement unit 30 shown in FIG. 1.

FIG. 9A is a graph showing an example of electrostatic capacitance-gate voltage characteristics of the sensor capacitor 100Sc. FIG. 9B is a graph showing an example of electrostatic capacitance-gate voltage characteristics of the reference capacitor 100Rc.

In the sensor capacitor 100Sc, the front surface of the gate layer 106S (for example, see FIG. 3A and FIG. 4A) is exposed. Therefore, as shown in FIG. 9A, as the gas concentration (for example, the gas concentration of nitrogen oxide gas) increases, the electrostatic capacitance-gate voltage characteristics of the sensor capacitor 100Sc shift in parallel in the right direction in the figure. More specifically, the threshold voltage of the gate layer 106S when the electrostatic capacitance of the sensor capacitor 100Sc becomes the threshold electrostatic capacitance C0 changes from the threshold voltage VGS(0) when the gas concentration is 0 to the threshold voltage VGS(X) when the gas concentration is X, and the threshold voltage of the gate layer 106S increases as the gas concentration increases.

<Measurement Method of Gas Concentration According to First Modification Example>

Next, a measurement method of gas concentration using the gas sensor according to the first modification example of the first embodiment will be described with reference to FIG. 1, FIG. 2, FIG. 8A, and FIG. 8B. In the following, a description will be given of a case where nitrogen oxide gas is exemplified as the detection target gas, oxygen gas is exemplified as the interfering gas, and the gas concentration of the nitrogen oxide gas is measured.

First, the control unit 50 adjusts the temperature of the sensor unit 100.

Next, the control unit 50 applies a predetermined voltage to each unit of the sensor capacitor 100Sc and the reference capacitor 100Rc.

For example, the power supply 41 applies a predetermined alternating voltage to the well 102S. The power supply 41 applies a predetermined threshold voltage VGS(0) to the gate layer 106S such that the electrostatic capacitance of the sensor capacitor 100Sc becomes the threshold electrostatic capacitance C0. The power supply 41 also applies a predetermined alternating voltage to the well 102R. The power supply 41 applies a predetermined threshold voltage VGR(0) to the gate layer 106R such that the electrostatic capacitance of the reference capacitor 100Rc becomes the threshold electrostatic capacitance C0.

Note that the threshold voltage VGS(0) of the sensor capacitor 100Sc and the threshold voltage VGR(0) of the reference capacitor 100Rc in the case where the gas concentration is 0 may be measured in advance. Also, for example, the control unit 50 may read respective data of the threshold voltages VGS(0) and VGR(0) measured in advance from a data storage unit not shown as needed. The control unit 50 outputs the data of the threshold voltages VGS(0) and VGR(0) to the gas concentration measurement unit 30, for example.

Next, the control unit 50 measures the threshold voltage VGS(X) of the sensor capacitor 100Sc and the threshold voltage VGR(X) of the reference capacitor 100Rc in the case where nitrogen oxide gas is contained in the atmosphere. Note that the gate layer 106R of the reference capacitor 100Rc is isolated from the atmosphere by the insulation film 111R (for example, see FIG. 3B and FIG. 4B). Therefore, the threshold voltage VGR(X) of the reference capacitor 100Rc is the same as the threshold voltage VGR(0) when the gas concentration is 0.

The control unit 50 outputs respective data of the measured threshold voltages VGS(X) and VGR(X) to the gas concentration measurement unit 30, for example.

Even when the oxygen gas is contained as an interfering gas in the atmosphere, the gas concentration of the oxygen gas in the cavity 130S (for example, see FIG. 3A and FIG. 4A) can be sufficiently reduced by the ion pump 150S so as not to affect the threshold voltage VGS(X). The gas in the atmosphere is introduced into the cavity 130S via the gas diffusion resistance film 131S (for example, see FIG. 4A). From the gas in the atmosphere, the oxygen gas is removed by the ion pump 150S, and the gas comes into contact with the sensor capacitor 100Sc having the gate layer 106S exposed to the cavity 130S.

When the nitrogen oxide gas is contained in the gas in the atmosphere, the threshold voltage VGS(X) changes depending on the gas concentration of the nitrogen oxide gas. For example, in the case of exhaust gas of engine automobiles, nitrogen oxide gas often contains both nitrogen monoxide (NO) and nitrogen dioxide ($NO_2$) When the above voltage is applied to the ion pump 150S, nitrogen dioxide ($NO_2$) is converted into nitrogen monoxide (NO). In the sensor capacitor 100Sc having the gate layer 106S, the gas concentration of nitrogen monoxide (NO) gas in the gas in which oxygen is removed to convert nitrogen dioxide ($NO_2$) into nitrogen monoxide (NO), of the mixed gas of nitrogen monoxide (NO) and nitrogen dioxide ($NO_2$), is measured.

Next, based on the threshold voltages VGS(0), VGR(0), VGS(X), and VGR(X) output from the control unit 50, the gas concentration measurement unit 30 calculates the threshold value change amount of the sensor capacitor 100Sc. For example, the gas concentration measurement unit 30 calculates the threshold value change amount of the sensor capacitor 100Sc from the difference between the potential difference VGRS(0) between the sensor capacitor 100Sc and the reference capacitor 100Rc when there is no nitrogen oxide gas in the atmosphere and the potential difference VGRS (X) between the sensor capacitor 100Sc and the reference capacitor 100Rc when there is nitrogen oxide gas in the atmosphere. That is, the threshold value change amount $\Delta Vg(X)$ of the sensor capacitor 100Sc is expressed by (Expression 1) described above.

The threshold value change amount indicated in (Expression 1) is made in view of the threshold voltages VGR(0) and VGR(X) of the reference capacitor 100Rc. This is to suppress the influence of the noise generated in the sensor unit 100 due to temperature change and the like.

Note that, when the variations of the threshold voltages VGS(0) and VGS(X) due to noise are small, the gas concentration measurement unit 30 may measure the gas concentration using only the sensor capacitor 100Sc. In this case, the gas concentration measurement unit 30 measures the gas concentration of the nitrogen oxide gas on the basis of the threshold value change amount Vg(X) which is the difference between the threshold voltage VGS(0) applied to the gate layer 106S when there is no nitrogen oxide gas in the atmosphere and the threshold voltage VGS(X) applied to the gate layer 106S when there is nitrogen oxide gas in the atmosphere. Here, the threshold voltage VGS(0) is the voltage applied to the gate layer 106S when the electrostatic capacitance of the sensor capacitor 100Sc becomes the threshold electrostatic capacitance CO in the case where there is no nitrogen oxide gas in the atmosphere. Also, the threshold voltage VGS(X) is the voltage applied to the gate layer 106S when the electrostatic capacitance of the sensor capacitor 100Sc becomes the threshold electrostatic capacitance CO in the case where there is nitrogen oxide gas in the atmosphere.

Therefore, the threshold value change amount $\Delta Vg(X)$ in this case is expressed by (Expression 2) described above.

<Second Modification of Work Function Type Element>

Figure 10A:
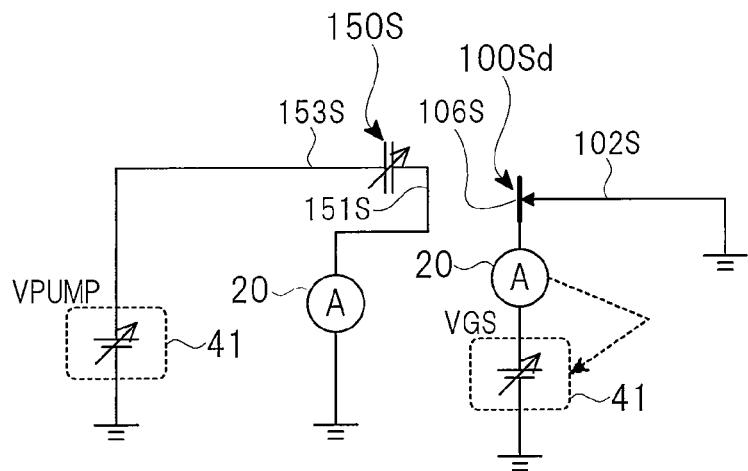
FIG. 10A is a circuit diagram showing an example of a connection structure of a sensor diode in a sensor unit according to a second modification example of the first embodiment.
Figure 10B:
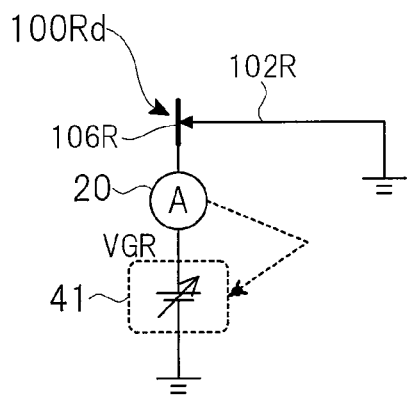
FIG. 10B is a circuit diagram showing an example of a connection structure of a reference diode in the sensor unit according to the second modification example of the first embodiment.
Figure 10C:
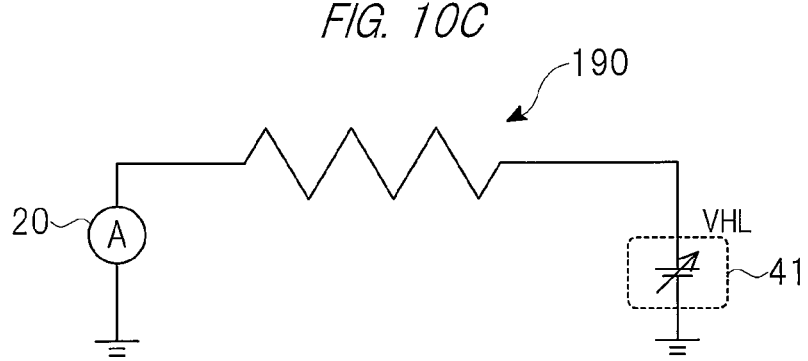
FIG. 10C is a circuit diagram showing an example of a connection structure of a heater in the sensor unit according to the second modification example of the first embodiment.
Figure 11A:
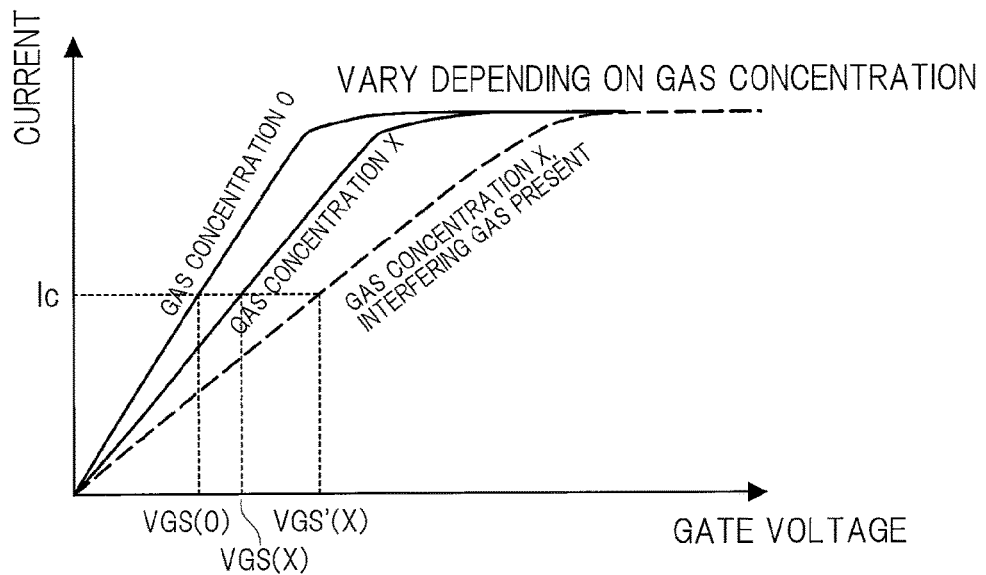
FIG. 11A is a graph showing an example of current-gate voltage characteristics of the sensor diode in a gas sensor according to the second modification example of the first embodiment.
Figure 11B:
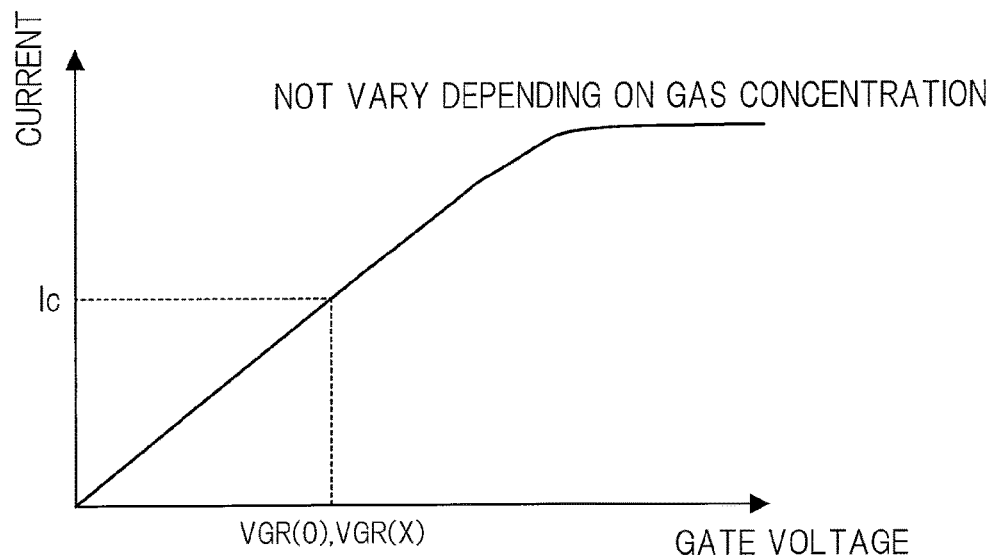
FIG. 11B is a graph showing an example of current-gate voltage characteristics of the reference diode in the gas sensor according to the second modification example of the first embodiment.

A work function type sensor according to a second modification example of the first embodiment will be described with reference to FIG. 10 and FIG. 11. FIG. 10A is a circuit diagram showing an example of a connection structure of a sensor diode in a sensor unit according to the second modification example of the first embodiment. FIG. 10B is a circuit diagram showing an example of a connection structure of a reference diode in the sensor unit according to the second modification example of the first embodiment. FIG. 10C is a circuit diagram showing an example of a connection structure of a heater in the sensor unit according to the second modification example of the first embodiment. FIG. 11A is a graph showing an example of current-gate voltage characteristics of the sensor diode in a gas sensor according to the second modification example of the first embodiment. FIG. 11B is a graph showing an example of current-gate voltage characteristics of the reference diode in the gas sensor according to the second modification example of the first embodiment.

The gas sensor according to the second modification uses the sensor diode 100Sd for the sensor element 100S and the reference diode 100Rd for the reference element 100R.

The sensor diode 100Sd can be realized by a structure in which a part of the gate insulation film 105S is removed and the gate layer 106S is in direct contact with the well 102S in the device structure shown in FIG. 2, FIG. 3A, and FIG. 4A. As with the case of the sensor capacitor 100Sc, the source diffusion layer 103S and the drain diffusion layer 104S can be omitted.

The reference diode 100Rd can be realized with a structure in which a part of the gate insulation film 105R is removed and the gate layer 106R is in direct contact with the well 102R in the device structure shown in FIG. 2, FIG. 3B, and FIG. 4B. As with the case of the reference capacitor 100Rc, the source diffusion layer 103R and the drain diffusion layer 104R can be omitted.

Note that, in the following description, it is assumed that the conductivity types of the wells 102S and 102R are configured as the N type. However, the conductivity types of the wells 102S and 102R may be configured as the P type. Alternatively, one of the wells 102S and 102R may be configured as the N type, and the other of the wells 102S and 102R may be configured as the P type.

As shown in FIG. 10A and FIG. 10B, the well 102S of the sensor diode 100Sd and the well 102R of the reference diode 100Rd are grounded. Note that each of the wells 102S and 102R may be connected to the power supply 41 applying a predetermined voltage.

The gate layer 106S of the sensor diode 100Sd is connected to the power supply 41 which applies the variable voltage VGS. The gate layer 106R of the reference diode 100Rd is connected to the power supply 41 which applies the variable voltage VGR. Also, each of the gate layer 106S of the sensor diode 100Sd and the gate layer 106R of the reference diode 100Rd is connected to the current measurement unit 20.

As shown in FIG. 10A, the ion pump electrode 151S is connected to the current measurement unit 20. Also, the ion pump electrode 153S is connected to the power supply 41 which applies the voltage VPUMP operating the ion pump 150S.

For example, the current measurement unit 20 measures the diode current flowing between the gate layer 106S and the well 102S of the sensor diode 100Sd. Also, the current measurement unit 20 measures the diode current flowing between the gate layer 106R and the well 102R of the reference diode 100Rd, for example.

FIG. 11A is a graph showing an example of the current-gate voltage characteristics of the sensor diode 100Sd. FIG. 11B is a graph showing an example of the current-gate voltage characteristics of the reference diode 100Rd. Note that FIG. 11A shows the current-gate voltage characteristics when a forward bias is applied to the sensor diode 100Sd and FIG. 11B shows the current-gate voltage characteristics when a forward bias is applied to the reference diode 100Rd.

In the sensor diode 100Sd, the front surface of the gate layer 106S (for example, see FIG. 3A and FIG. 4A) is exposed. Therefore, as shown in FIG. 11A, as the gas concentration (for example, the gas concentration of nitrogen oxide gas) increases, the current-gate voltage characteristics of the sensor diode 100Sd shift in parallel in the right direction in the figure, and the waveforms deforms. More specifically, the threshold voltage of the gate layer 106S when the diode current of the sensor diode 100Sd becomes the threshold current Ic changes from the threshold voltage VGS(0) when the gas concentration is 0 to the threshold voltage VGS(X) when the gas concentration is X, and as the gas concentration increases, the threshold voltage of the gate layer 106S increases.

<Measurement Method of Gas Concentration According to Second Modification Example>

Next, a measurement method of gas concentration using a gas sensor according to the second modification example of the first embodiment will be described with reference to FIG. 1, FIG. 2, FIG. 10A, and FIG. 10B. In the following, a description will be given of a case where nitrogen oxide gas is exemplified as the detection target gas, oxygen gas is exemplified as the interfering gas, and the gas concentration of the nitrogen oxide gas is measured.

First, the control unit 50 adjusts the temperature of the sensor unit 100.

Next, the control unit 50 applies a predetermined voltage to each unit of the sensor diode 100Sd and the reference diode 100Rd.

For example, the power supply 41 applies a predetermined alternating voltage to the well 102S. The power supply 41 applies a predetermined threshold voltage VGS(0) to the gate layer 106S such that the diode current of the sensor diode 100Sd becomes the threshold current Ic. Also, the power supply 41 applies a predetermined voltage to the well 102R. The power supply 41 applies a predetermined threshold voltage VGR(0) to the gate layer 106R such that the diode current of the reference diode 100Rd becomes the threshold current Ic.

Note that the threshold voltage VGS(0) of the sensor diode 100Sd and the threshold voltage VGR(0) of the reference diode 100Rd in the case where the gas concentration is 0 may be measured in advance. Also, the control unit 50 may read respective data of the threshold voltages VGS(0) and VGR(0) measured in advance from a data storage unit not shown as needed, for example. The control unit 50 outputs the data of the threshold voltages VGS(0) and VGR(0) to the gas concentration measurement unit 30, for example.

Next, the control unit 50 measures the threshold voltage VGS(X) of the sensor diode 100Sd and the threshold voltage VGR(X) of the reference diode 100Rd in the case where nitrogen oxide gas is contained in the atmosphere. Note that the gate layer 106R of the reference diode 100Rd is isolated from the atmosphere by the insulation film 111R (for example, see FIG. 3B and FIG. 4B). Therefore, the threshold voltage VGR (X) of the reference diode 100Rd is the same as the threshold voltage VGR(0) when the gas concentration is 0.

The control unit 50 outputs respective data of the measured threshold voltages VGS(X) and VGR(X) to the gas concentration measurement unit 30, for example.

Even when the oxygen gas is contained as an interfering gas in the atmosphere, the gas concentration of the oxygen gas in the cavity 130S (for example, see FIG. 3A and FIG. 4A) can be sufficiently reduced by the ion pump 150S so as not to affect the threshold voltage VGS(X). The gas in the atmosphere is introduced into the cavity 130S via the gas diffusion resistance film 131S (for example, see FIG. 4A). From the gas in the atmosphere, the oxygen gas is removed by the ion pump 150S, and the gas comes into contact with the sensor diode 100Sd having the gate layer 106S exposed to the cavity 130S.

When the nitrogen oxide gas is contained in the gas in the atmosphere, the threshold voltage VGS(X) changes depending on the gas concentration of the nitrogen oxide gas. For example, in the case of exhaust gas of engine automobiles, nitrogen oxide gas often contains both nitrogen monoxide (NO) and nitrogen dioxide ($NO_2$) When the above voltage is applied to the ion pump 150S, nitrogen dioxide ($NO_2$) is converted into nitrogen monoxide (NO). The sensor diode 100Sd having the gate layer 106S measures the gas concentration of nitrogen monoxide (NO) gas in the gas in which oxygen is removed to convert nitrogen dioxide ($NO_2$) into nitrogen monoxide (NO), of the mixed gas of nitrogen monoxide (NO) and nitrogen dioxide ($NO_2$).

Next, based on the threshold voltages VGS(0), VGR(0), VGS(X), and VGR(X) output from the control unit 50, the gas concentration measurement unit 30 calculates the threshold value change amount of the sensor diode 100Sd. For example, the gas concentration measurement unit 30 calculates the threshold value change amount of the sensor diode 100Sd from the difference between the potential difference VGRS(0) between the sensor diode 100Sd and the reference diode 100Rd when there is no nitrogen oxide gas in the atmosphere and the potential difference VGRS (X) between the sensor diode 100Sd and the reference diode 100Rd when there is nitrogen oxide gas in the atmosphere. That is, the threshold value change amount $\Delta Vg(X)$ of the sensor diode 100Sd is expressed by (Expression 1) described above.

The threshold value change amount indicated in (Expression 1) is made in view of the threshold voltages VGR(0) and VGR(X) of the reference diode 100Rd. This is to suppress the influence of the noise generated in the sensor unit 100 due to temperature change and the like.

Note that, when the variations of the threshold voltages VGS(0) and VGS(X) due to noise are small, the gas concentration measurement unit 30 may measure the gas concentration using only the sensor diode 100Sd. In this case, the gas concentration measurement unit 30 measures the gas concentration of the nitrogen oxide gas on the basis of the threshold value change amount Vg(X) which is the difference between the threshold voltage VGS(0) applied to the gate layer 106S when there is no nitrogen oxide gas in the atmosphere and the threshold voltage VGS(X) applied to the gate layer 106S when there is nitrogen oxide gas in the atmosphere. Here, the threshold voltage VGS(0) is the voltage applied to the gate layer 106S when the diode current of the sensor diode 100Sd becomes the threshold current Ic in the case where there is no nitrogen oxide gas in the atmosphere. Also, the threshold voltage VGS(X) is a voltage applied to the gate layer 106S when the diode current of the sensor diode 100Sd becomes the threshold current Ic in the case where there is nitrogen oxide gas in the atmosphere.

Therefore, the threshold value change amount $\Delta Vg(X)$ in this case is expressed by (Expression 2) described above.

Effects Achieved by First Embodiment

According to the first embodiment, the ion pump function of removing the interfering gas other than the detection target gas contained in the atmosphere gas can be realized in the semiconductor chip. As a result, not only reduction in cost, size, and power consumption but also highly accurate gas sensing by removing the interfering gas can be achieved. In addition, the ion conductive film can be formed as a thin film, so that removal of the interfering gas by the ion pump can be realized with high efficiency. Penetration of the interfering gas into the exposed portion of the gate layer due to diffusion in the ion conductive film is suppressed by disposing the gas diffusion prevention film.

Second Embodiment

Figure 12:
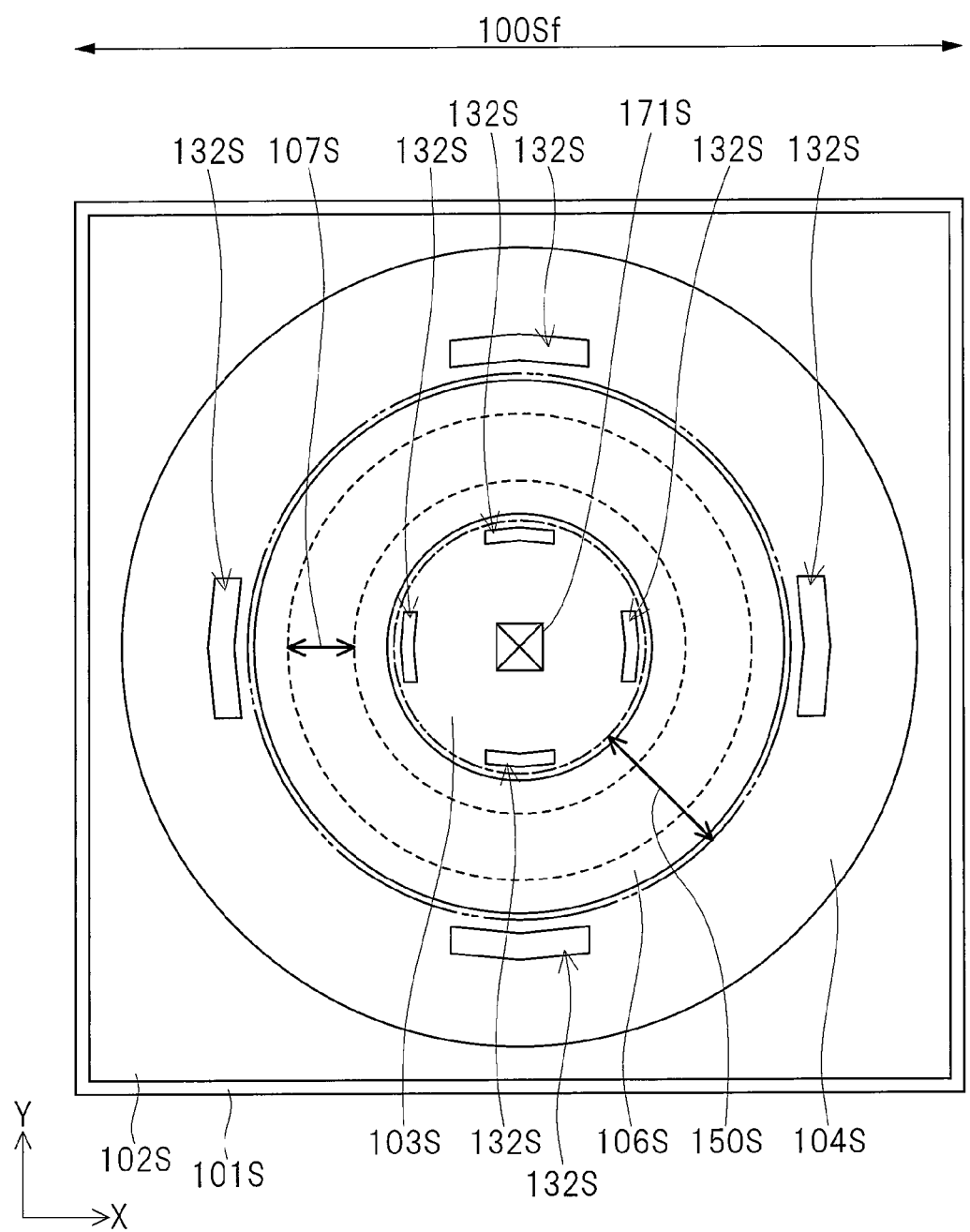
FIG. 12 is a plan view showing an example of a configuration of a sensor unit (sensor element) in a gas sensor according to a second embodiment.

A configuration of a gas sensor according to the second embodiment will be described with reference to FIG. 12. FIG. 12 is a plan view showing an example of a configuration of a sensor unit (sensor element) in the gas sensor according to the second embodiment.

In the first embodiment described above, the sensor FET 100Sf and the reference FET 100Rf using the trench isolation (insulation films 108S and 108R) have been described. In the second embodiment, a configuration of a gas sensor that does not require an insulation portion like the trench isolation will be described.

As shown in FIG. 12, a gate layer 106S is an annular shape surrounded by a circular outer shape and a circular inner shape in plan view, and the circular shape constituting the inner shape is smaller than the circular shape constituting the outer shape. That is, in plan view, the gate layer 106S has a ring shape, and a source diffusion layer 103S and a drain diffusion layer 104S are disposed on the inner side and the outer side of the ring-shaped gate layer 106S, respectively. This eliminates the end portion in the channel width direction, so that a portion defining the channel width direction becomes unnecessary. Especially when the gas sensor is used at high temperature, it is effective to suppress parasitic FET.

An exposed portion 107S is formed on a front surface of the ring-shaped gate layer 106S along the ring-shaped gate layer 106S. A plurality of gas introduction portions 132S are formed along an outer peripheral portion and an inner peripheral portion of the gate layer 106S, and an ion pump 150S is formed along the ring-shaped gate layer 106S. Thus, the entire exposed portion 107S of the gate layer 106S can be uniformly brought into contact with the atmosphere.

Meanwhile, although a ring-shaped field effect transistor is a known technique, the front surface of the gate layer 106S is exposed in the sensor FET 100Sf, and therefore, it is difficult to feed power to a diffusion layer in a central portion (the source diffusion layer 103S in FIG. 12) with a wiring layer of a semiconductor chip. When a wiring is laid across the ring-shaped gate layer 106S, an interlayer insulation film is normally required under the wiring, and a part of the front surface of the gate layer 106S is covered with interlayer insulation film. A part between the source diffusion layer 103S and the drain diffusion layer 104S of the sensor FET 100Sf responds to gas, but since the other part does not respond, a problem occurs in response characteristics.

In view of this, in the second embodiment, the power supply to the source diffusion layer 103S is not performed via the wiring on a main surface of a semiconductor substrate 101S, but is directly fed via a contact portion 171S by wire bonding. As for feeding power to the contact portion 171S, other method capable of supplying power to an electrode pad, e.g., crimping connection, can be used.

Third Embodiment

Figure 13:
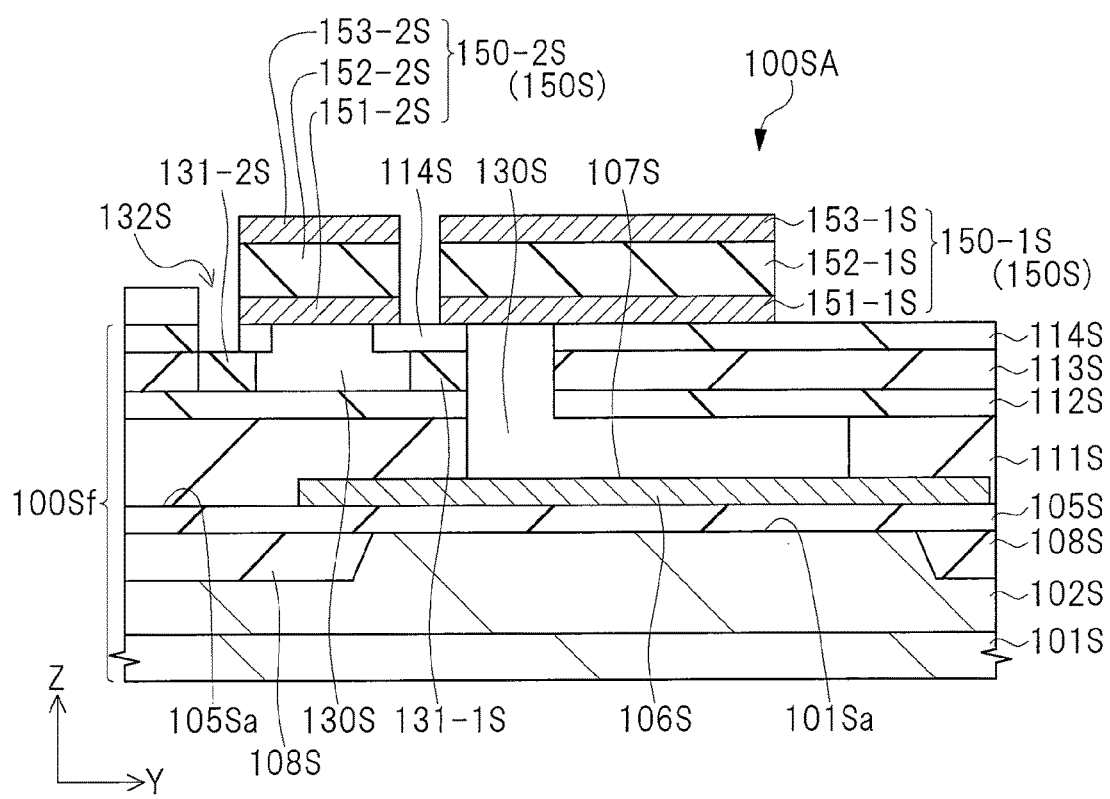
FIG. 13 is a cross-sectional view showing a first example of a configuration of a sensor unit (sensor element) in a gas sensor according to a third embodiment.
Figure 14:
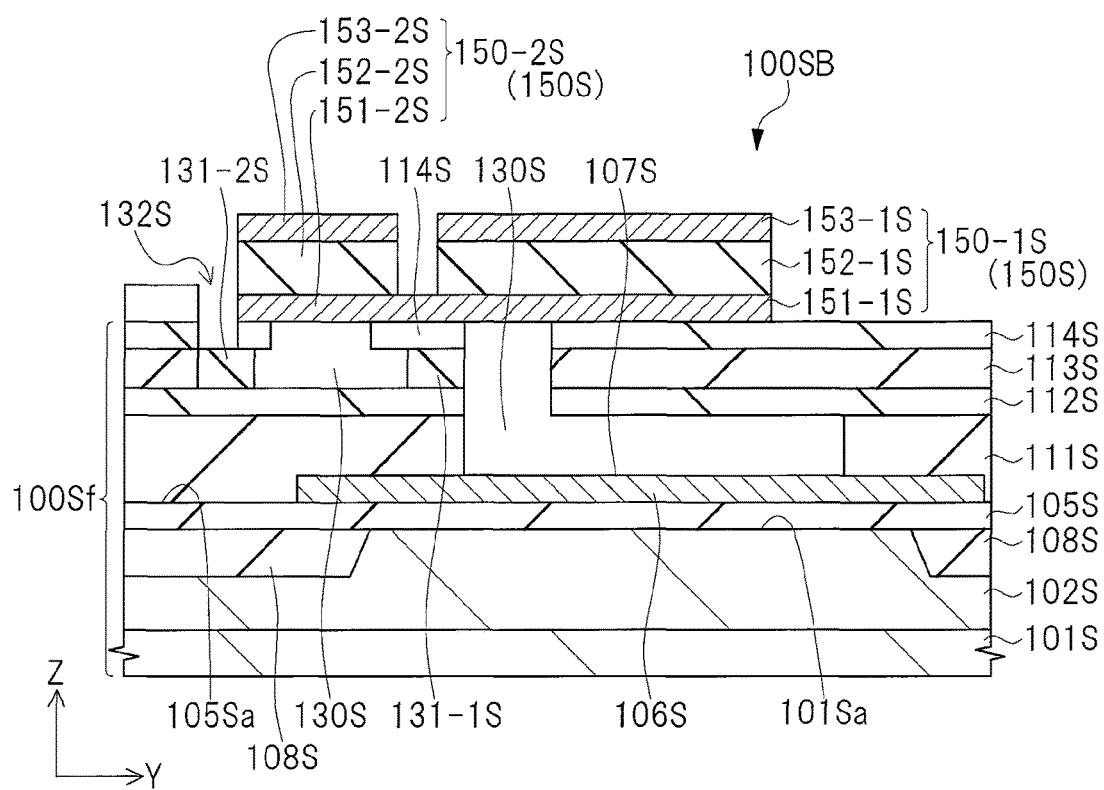
FIG. 14 is a cross-sectional view showing a second example of the configuration of the sensor unit (sensor element) in the gas sensor according to the third embodiment.
Figure 15:
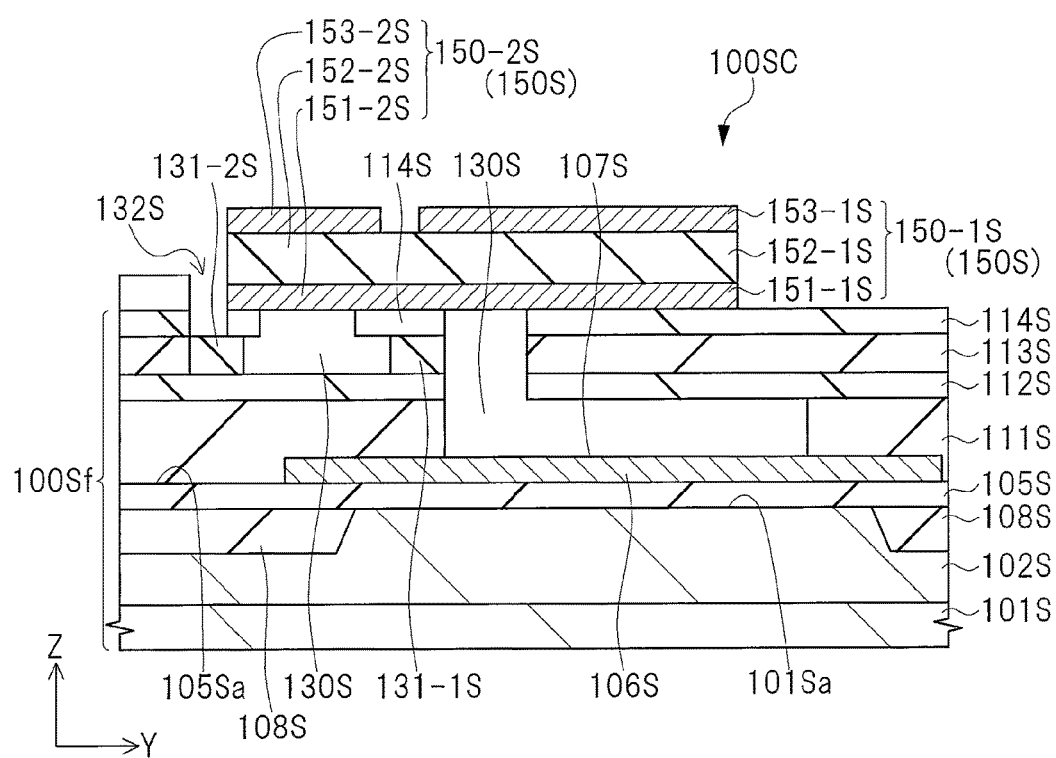
FIG. 15 is a cross-sectional view showing a third example of the configuration of the sensor unit (sensor element) in the gas sensor according to the third embodiment.

A configuration of a gas sensor according to the third embodiment will be described with reference to FIG. 13 to FIG. 15. FIG. 13 is a cross-sectional view showing a first example of a configuration of the sensor unit (sensor element) in the gas sensor according to the third embodiment. FIG. 14 is a cross-sectional view showing a second example of the configuration of the sensor unit (sensor element) in the gas sensor according to the third embodiment. FIG. 15 is a cross-sectional view showing a third example of the configuration of the sensor unit (sensor element) in the gas sensor according to the third embodiment.

In the first embodiment described above, the ion pump 150S of the sensor element 100S has a pair of electrodes, i.e., the ion pump electrode 151S and the ion pump electrode 153S. However, the electrodes of the ion pump 150S are not limited thereto, and the electrodes of the ion pump 150S may have plural pairs.

As shown in FIG. 13, for example, two pairs of electrodes of the ion pump 150S can be formed. Therefore, the two ion pumps 150S are formed, i.e., an ion pump 150-1S including an ion pump electrode 151-1S of a lower layer, an ion conductive film 152-1S, and an ion pump electrode 153-1S of an upper layer, and an ion pump 150-2S including an ion pump electrode 151-2S of a lower layer, an ion conductive film 152-2S, and an ion pump electrode 153-2S of an upper layer. In this case, it is important that the insulation film 114S remains in a separation portion between the ion pump 150-1S and the ion pump 150-2S such that a gas does not enter between an outside of the sensor element 100SA and a cavity 130S via the separation portion.

In the case of the sensor element 100SA shown in FIG. 13, the two ion pumps 150S (the ion pump 150-1S and the ion pump 150-2S) are formed, and therefore, for example, according to a method of removing oxygen gas with the ion pump 150-1S and removing hydrogen gas with the ion pump 150-2S, both oxidation and reduction processes of the gas in the cavity 130S are performed, so that the interfering gas can be removed. For example, the gas concentration of the oxygen gas after the oxygen gas removal can be confirmed by removing the oxygen gas with the ion pump 150-1S and measuring an ion current of the ion pump 150-2S.

Also, four electrodes, i.e., the ion pump electrode 151-1S, the ion pump electrode 153-1S, the ion pump electrode 151-2S, and the ion pump electrode 153-2S are formed in the sensor element 100SA, but it is not necessary for the four electrodes to apply potentials different from each other.

For example, when 0 V is applied to the ion pump electrodes 151-1S and 151-2S, a negative potential is applied to the ion pump electrode 153-1S, and a positive voltage is applied to the ion pump electrode 153-2S, an operation of removing the oxygen gas with the ion pump 150-2S and removing the hydrogen gas with the ion pump 150-1S can be performed. Alternatively, when 0 V is applied to the ion pump electrodes 151-1S and 151-2S and different positive voltages are applied to the ion pump electrode 153-1S and the ion pump electrode 153-2S, for example, an operation of removing the oxygen gas with the ion pump 150-2S and measuring the gas concentration of the remaining oxygen gas with the ion pump 150-1S can be performed.

Meanwhile, in the sensor element 100SA, the electrode of the lower layer is separated into the ion pump electrode 151-1S and the ion pump electrode 151-2S. The electrode of the upper layer is separated into the ion pump electrode 153-1S and the ion pump electrode 153-2S. However, electrodes to which the same potential is applied may be physically connected to each other.

In a sensor element 100SB shown in FIG. 14, the ion pump electrode 151-1S and the ion pump electrode 151-2S which are the electrodes of the lower layer are physically connected and integrated. It is needless to say that the ion pump electrode 153-1S and the ion pump electrode 153-2S which are the electrodes of the upper layer may be physically connected and integrated.

Also, in the sensor elements 100SA and 100SB, the ion conductive film 152-1S is formed in the ion pump 150-1S, the ion conductive film 152-2S is formed in the ion pump 150-2S, and the ion conductive film 152-1S and the ion conductive film 152-2S are separated from each other. However, the ion conductive film 152-1S and the ion conductive film 152-2S may be connected.

In a sensor element 100SC shown in FIG. 15, the ion pump electrode 151-1S and the ion pump electrode 151-2S which are the electrodes of the lower layer are physically connected and integrated. Further, the ion conductive film 152-1S and the ion conductive film 152-2S are physically connected and integrated.

In the above-mentioned sensor elements 100SA, 100SB, and 100SC, the two ion pumps 150S are formed, but three or more ion pumps 150S may be formed.

Fourth Embodiment

<Configuration of Gas Sensor>

Figure 16A:
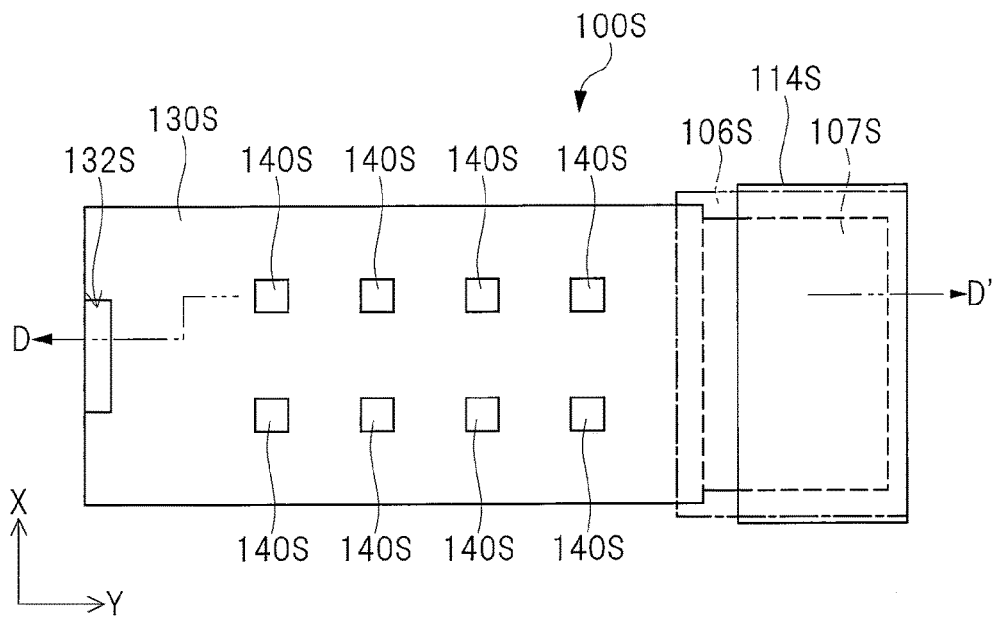
FIG. 16A is a plan view showing an example of a configuration of a sensor unit (sensor element) in a gas sensor according to a fourth embodiment.
Figure 16B:
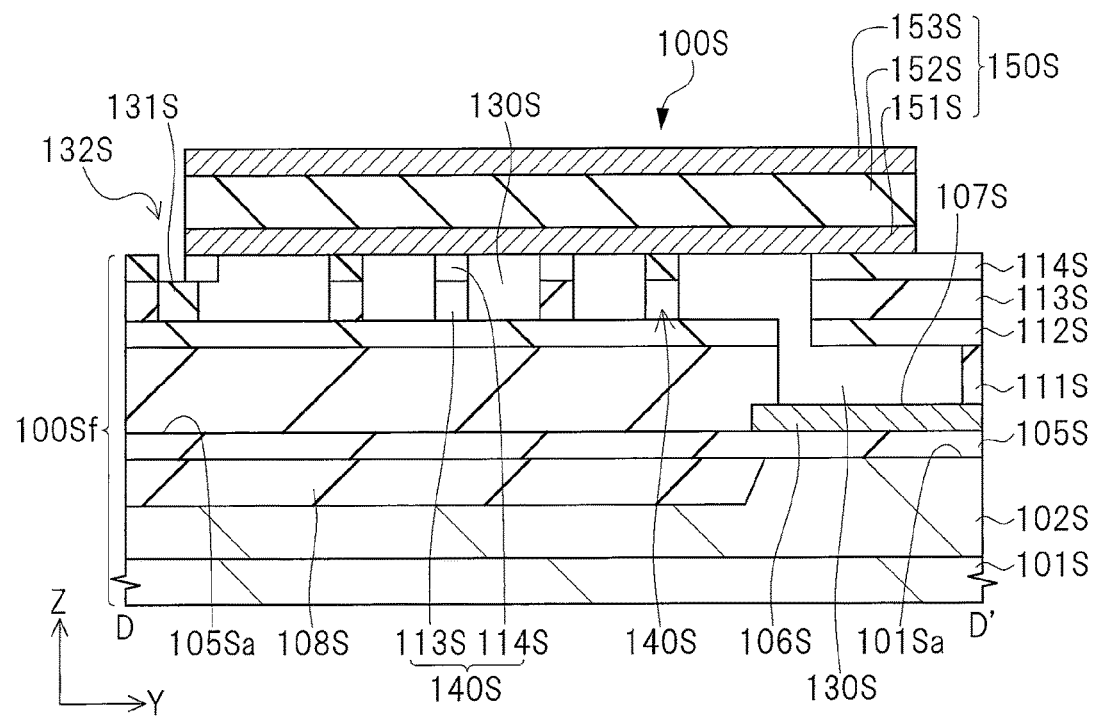
FIG. 16B is a cross-sectional view taken along a line D-D' in FIG. 16A.

A configuration of a gas sensor according to the fourth embodiment will be described with reference to FIG. 16. FIG. 16A is a plan view showing an example of a configuration of a sensor unit (sensor element) in the gas sensor according to the fourth embodiment. FIG. 16B is a cross-sectional view taken along a line D-D' in FIG. 16A. Note that FIG. 16A shows a plan view seen through an ion pump 150S.

In the sensor element 100S according to the first embodiment described above, dimensions in the X direction and the Y direction of the cavity 130S of the sensor FET 100Sf may become larger than substantially several 100 µm. In this case, stress may distort the film on an upper surface side of the cavity 130S and the film on a lower surface side of the cavity 130S, and the upper surface and the lower surface of the cavity 130S may come into contact with each other, whereby the cavity 130S may be crushed. Since the cavity 130S is a path of gas from the gas introduction portion 132S to the exposed portion 107S of the gate layer 106S, if the cavity 130S is crushed, the gas concentration cannot be measured.

In view of this, as shown in FIG. 16A and FIG. 16B, in the sensor element 100S according to the fourth embodiment, a plurality of pillar shaped portions 140S which are columnar structures inside the cavity 130S are formed, and the pillar shaped portion 140S reinforces the cavity 130S by connecting the upper surface and the lower surface of the cavity 130S. For example, the pillar shaped portion 140S is made of a laminated film including the insulation films 113S and 114S. This makes it possible to prevent the crush of the cavity 130S.

<Manufacturing Method of Gas Sensor>

An example of a manufacturing method of a gas sensor according to the fourth embodiment will be described with reference to FIG. 17 to FIG. 31. Each A of FIG. 17 to FIG. 28 is a plan view showing an example of a configuration of the sensor unit (sensor element) in the gas sensor according to the fourth embodiment. Each B of FIG. 17 to FIG. 28 is a cross-sectional view taken along a line D-D' in each A of FIG. 17 to FIG. 28. Each A of FIG. 29 to FIG. 32 is a cross-sectional view taken along a line E-E' in FIG. 28. Each B of FIG. 29 to FIG. 32 is a cross-sectional view taken along a line F-F' in FIG. 28.

Figure 17A:
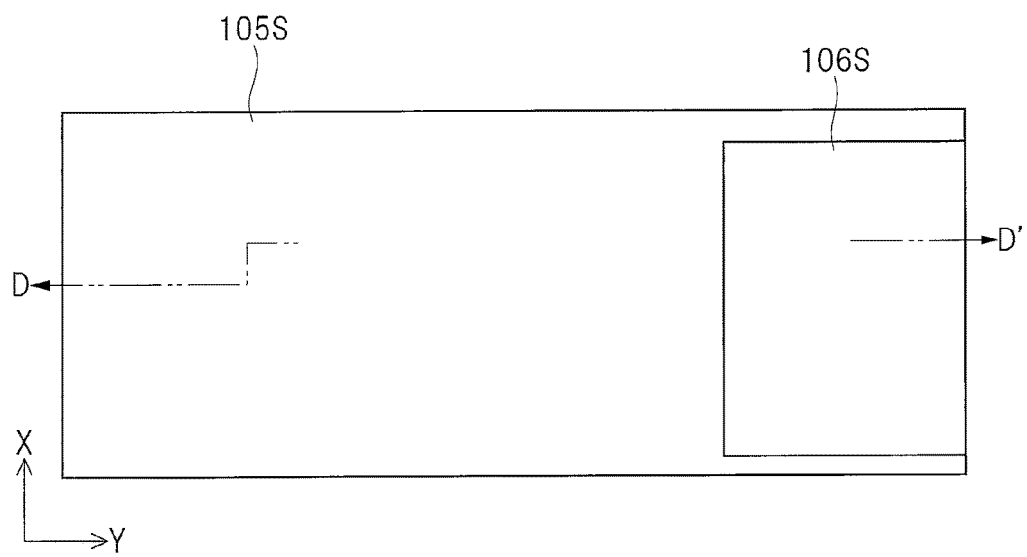
FIG. 17A is a plan view showing an example of a manufacturing process of the sensor unit (sensor element) in the gas sensor according to the fourth embodiment.
Figure 17B:
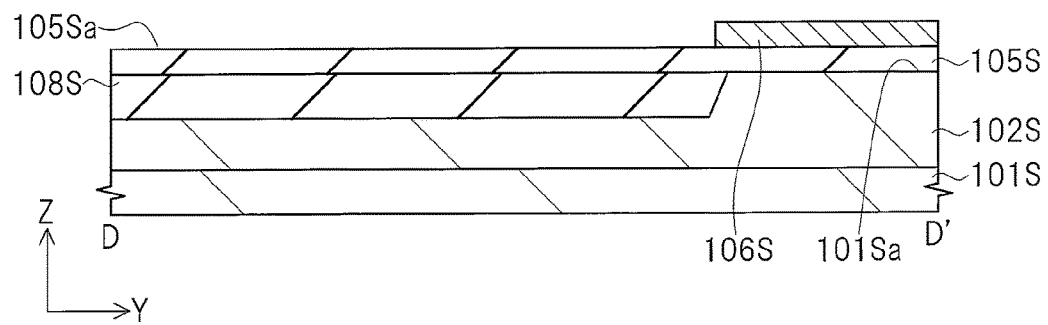
FIG. 17B is a cross-sectional view taken along a line D-D' in FIG. 17A.

First, as shown in FIG. 17A and FIG. 17B, a semiconductor substrate 101S made of, for example, single crystal silicon (Si) is prepared. Next, a trench isolation made of an insulation film 108S is formed on a side of a main surface 101Sa of the semiconductor substrate 101S, and then, impurity ions are implanted into the semiconductor substrate 101S to form a well 102S. Next, a gate insulation film 105S and a gate layer 106S are sequentially formed over the main surface 101Sa (the well 102S and the insulation film 108S) of the semiconductor substrate 101S.

Figure 18A:
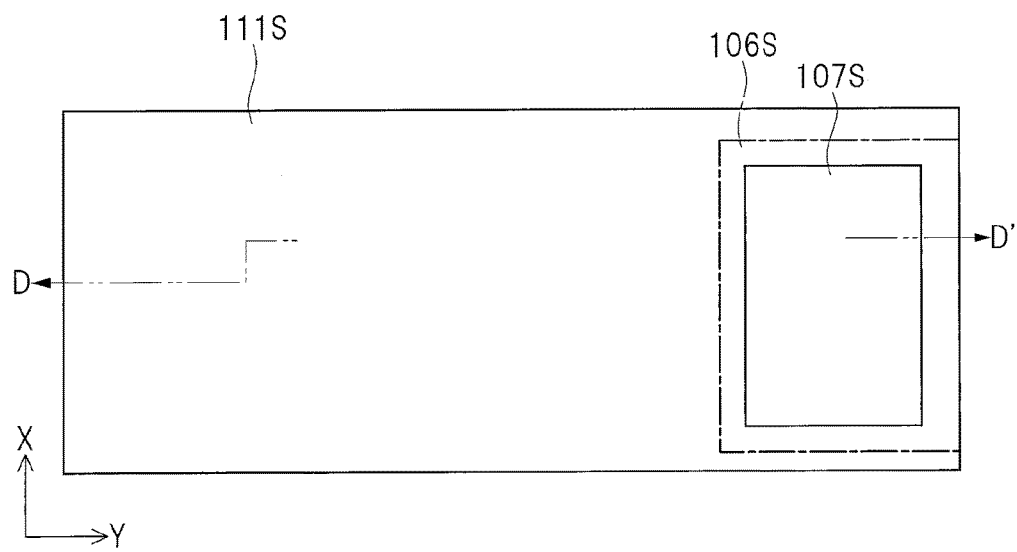
FIG. 18A is a plan view showing the manufacturing process of the gas sensor continued from FIG. 17A.
Figure 18B:
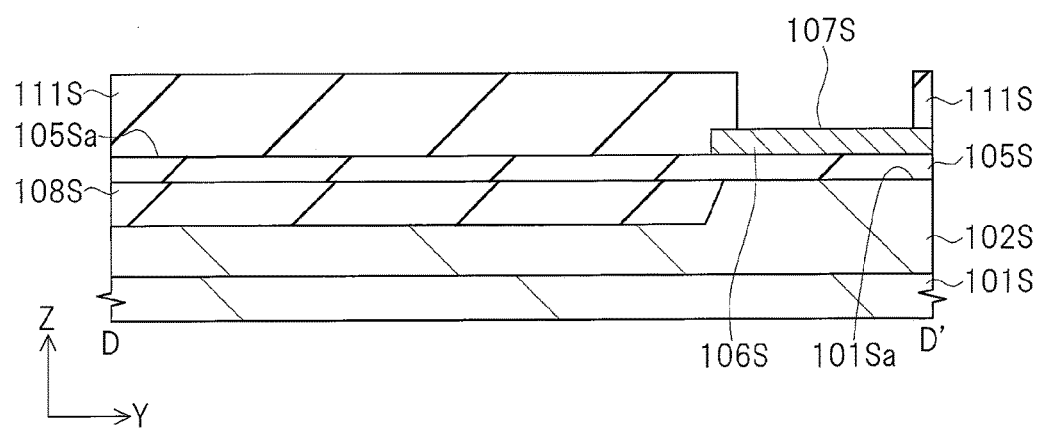
FIG. 18B is a cross-sectional view showing the manufacturing process of the gas sensor continued from FIG. 17B.

Next, as shown in FIG. 18A and FIG. 18B, after an insulation film 111S covering the gate layer 106S is formed over the gate insulation film 105S, the insulation film 111S over a part of a front surface of the gate layer 106S is removed, and the part of the front surface of the gate layer 106S is exposed. The insulation film 111S is made of, for example, silicon dioxide ($SiO_2$). Thereby, an exposed portion 107S of the gate layer 106S is formed.

Figure 19A:
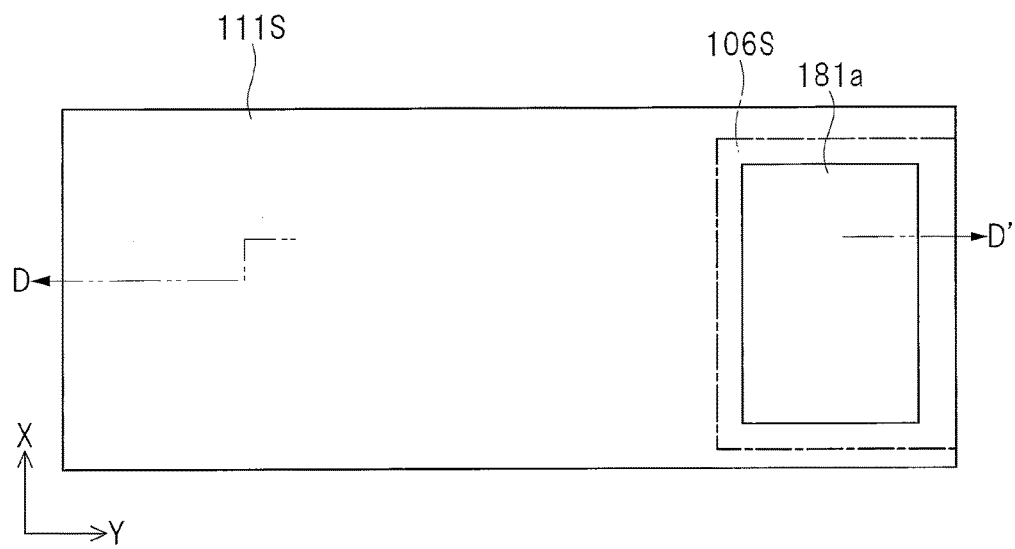
FIG. 19A is a plan view showing the manufacturing process of the gas sensor continued from FIG. 18A.
Figure 19B:
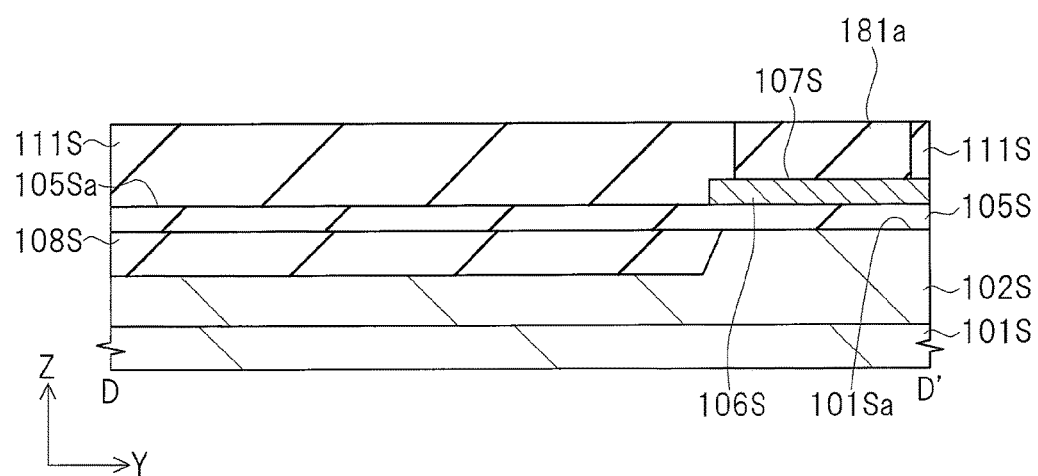
FIG. 19B is a cross-sectional view showing the manufacturing process of the gas sensor continued from FIG. 18B.

Next, as shown in FIG. 19A and FIG. 19B, a sacrificial film 181a fills a recess formed in the insulation film 111S and covers the exposed portion 107S of the gate layer 106S. The sacrificial film 181a is made of an organic material such as resist or a metal, for example.

Figure 20A:
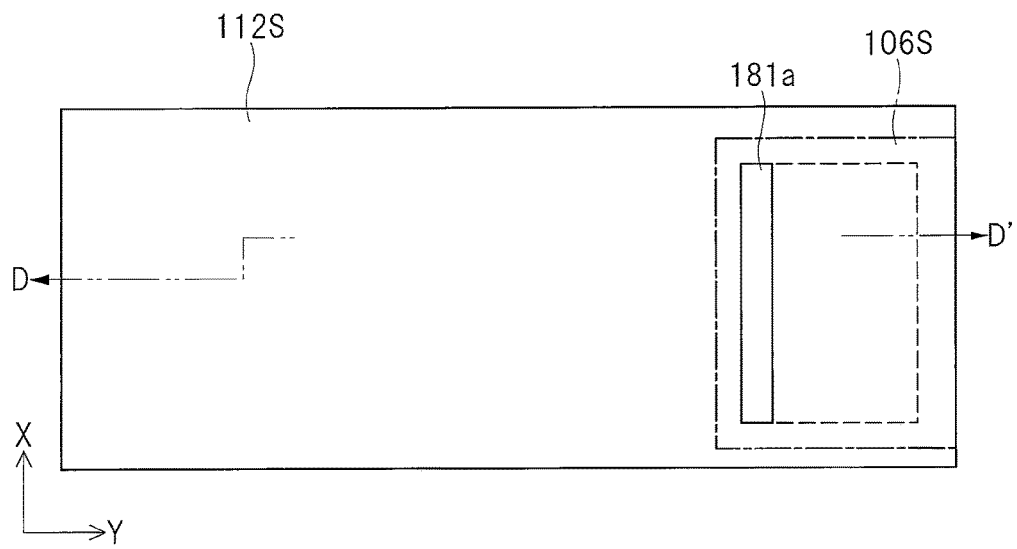
FIG. 20A is a plan view showing the manufacturing process of the gas sensor continued from FIG. 19A.
Figure 20B:
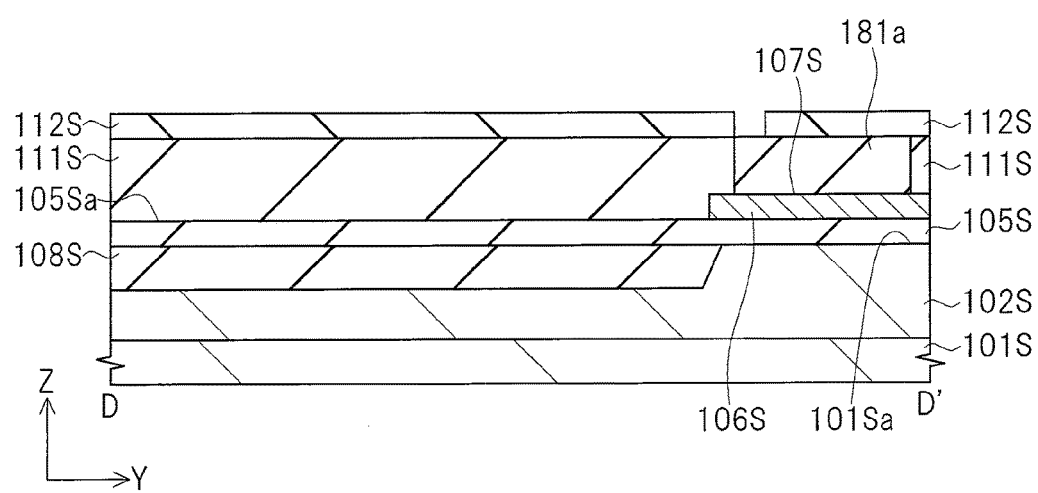
FIG. 20B is a cross-sectional view showing the manufacturing process of the gas sensor continued from FIG. 19B.

Next, as shown in FIG. 20A and FIG. 20B, after the insulation film 112S is formed over the insulation film 111S and the sacrificial film 181a, the insulation film 112S is partially removed, and the sacrificial film 181a is partially exposed. The insulation film 112S is made of, for example, silicon nitride (SiN).

Figure 21A:
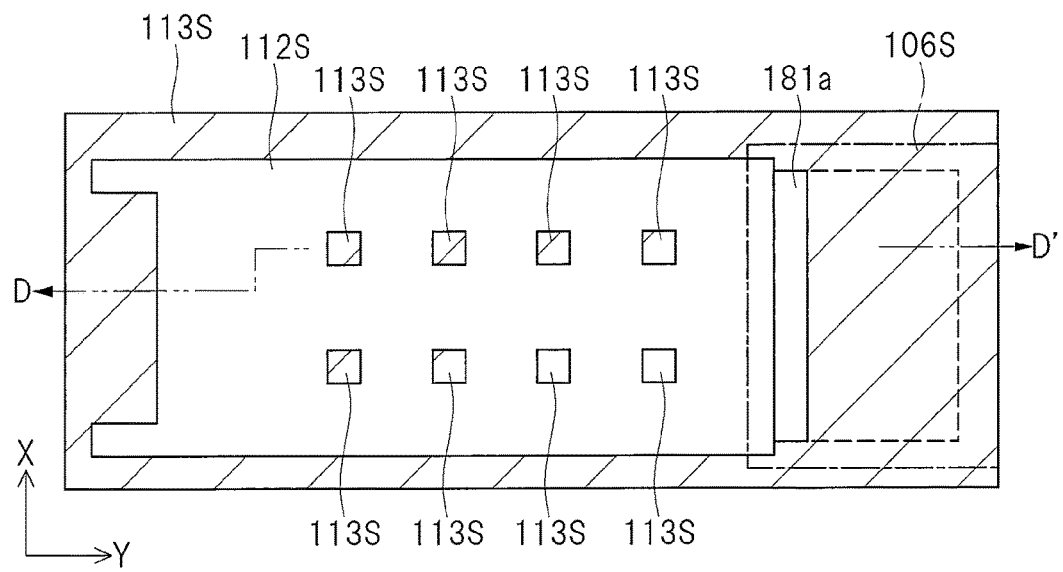
FIG. 21A is a plan view showing the manufacturing process of the gas sensor continued from FIG. 20A.
Figure 21B:
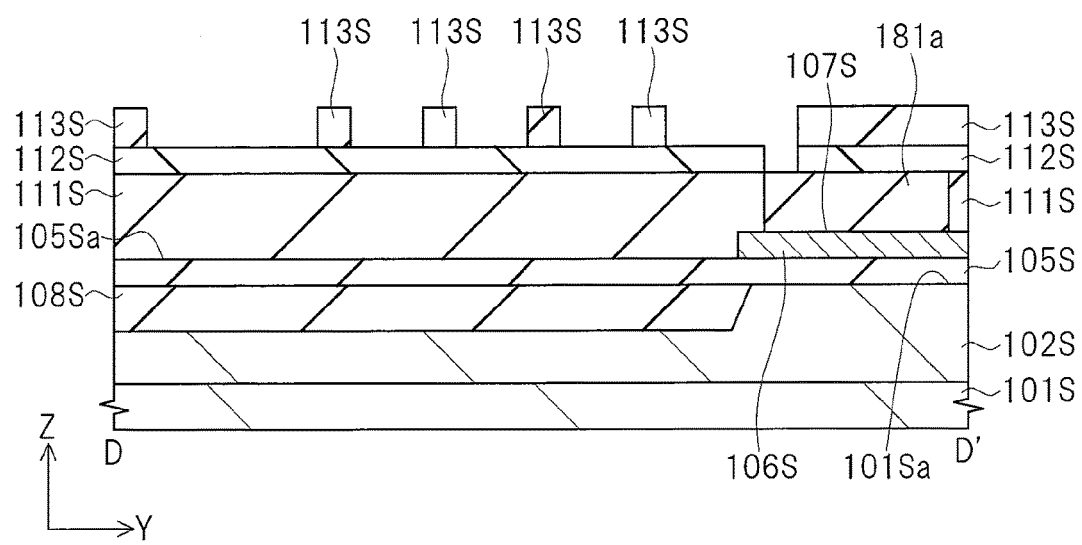
FIG. 21B is a cross-sectional view showing the manufacturing process of the gas sensor continued from FIG. 20B.

Next, as shown in FIG. 21A and FIG. 21B, after an insulation film 113S is formed over the insulation film 112S and the exposed sacrificial film 181a, the insulation film 113S is partially removed, so that the insulation film 112S and the sacrificial film 181a are partially exposed. At this time, a columnar structure made of the insulation film 113S is also formed in a region serving as the cavity 130S later. The insulation film 113S is made of, for example, silicon dioxide ($SiO_2$).

Figure 22A:
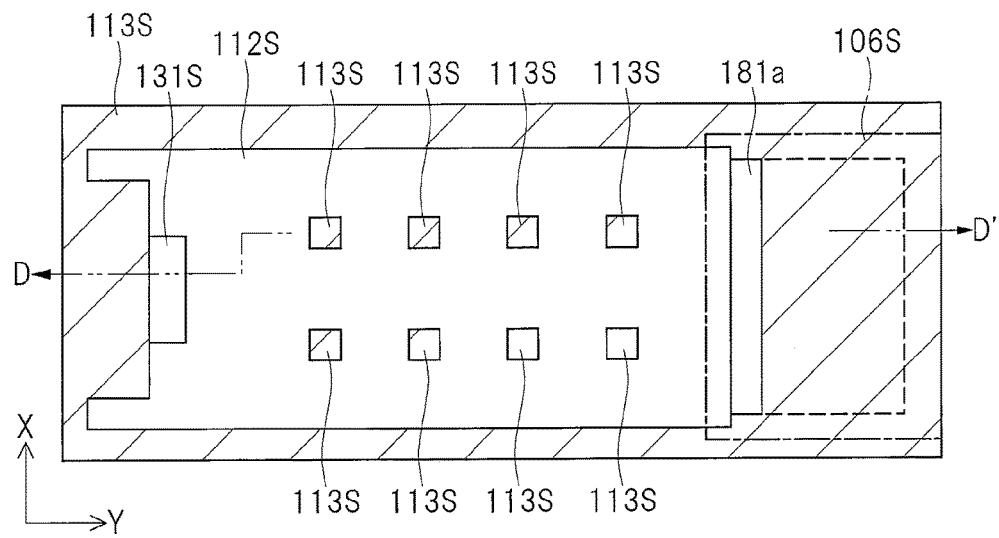
FIG. 22A is a plan view showing the manufacturing process of the gas sensor continued from FIG. 21A.
Figure 22B:
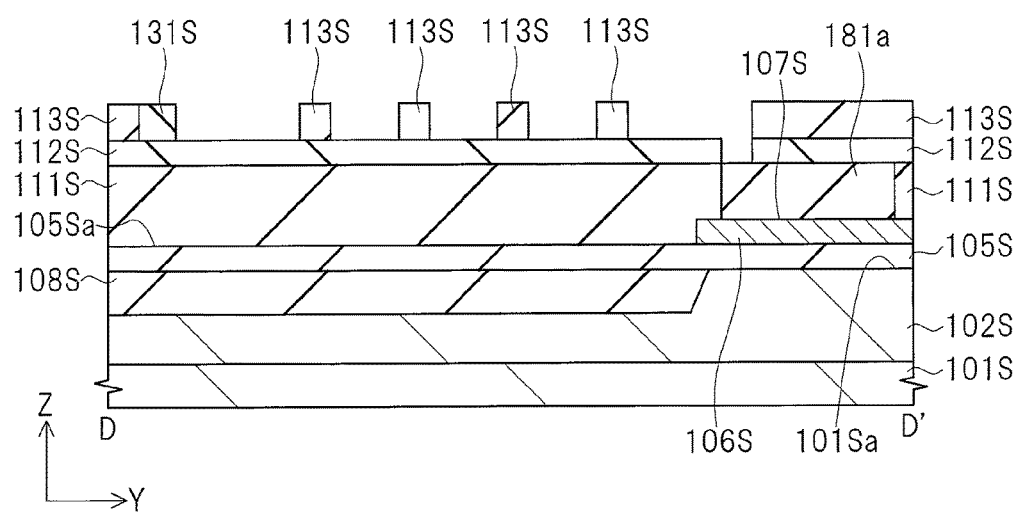
FIG. 22B is a cross-sectional view showing the manufacturing process of the gas sensor continued from FIG. 21B.

Next, as shown in FIG. 22A and FIG. 22B, after a gas diffusion resistance film 131S is formed over the insulation film 113S, the exposed insulation film 112S, and the exposed sacrificial film 181a, the gas diffusion resistance film 131S is processed, so that the gas diffusion resistance film 131S is formed over a partial region of the insulation film 112S in a region serving as the cavity 130S later, for example. The gas diffusion resistance film 131S is made of, for example, alumina ($Al_2O_3$) and the like.

Figure 23A:
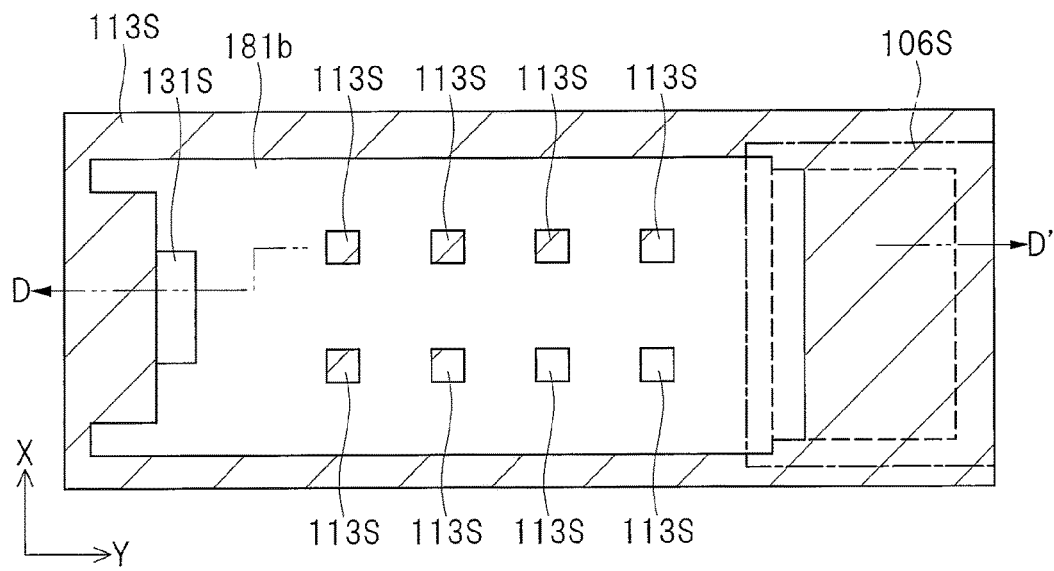
FIG. 23A is a plan view showing the manufacturing process of the gas sensor continued from FIG. 22A.
Figure 23B:
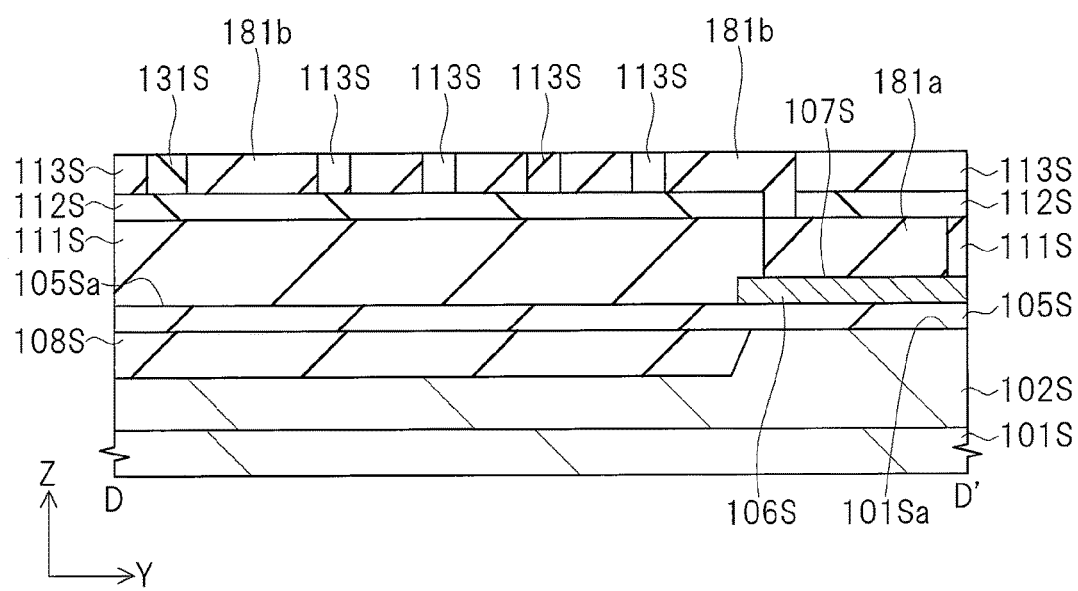
FIG. 23B is a cross-sectional view showing the manufacturing process of the gas sensor continued from FIG. 22B.

Next, as shown in FIG. 23A and FIG. 23B, after a sacrificial film 181b is formed over the insulation film 113S, the gas diffusion resistance film 131S, the exposed insulation film 112S, and the exposed sacrificial film 181a, the sacrificial film 181b is polished, for example, so that the sacrificial film 181b is embedded in space portions between the insulation films 113S and the like adjacent to each other. The sacrificial film 181b is made of an organic material such as resist or a metal, for example. At this time, the sacrificial film 181b is removed from an upper surface of the insulation film 113S.

Figure 24A:
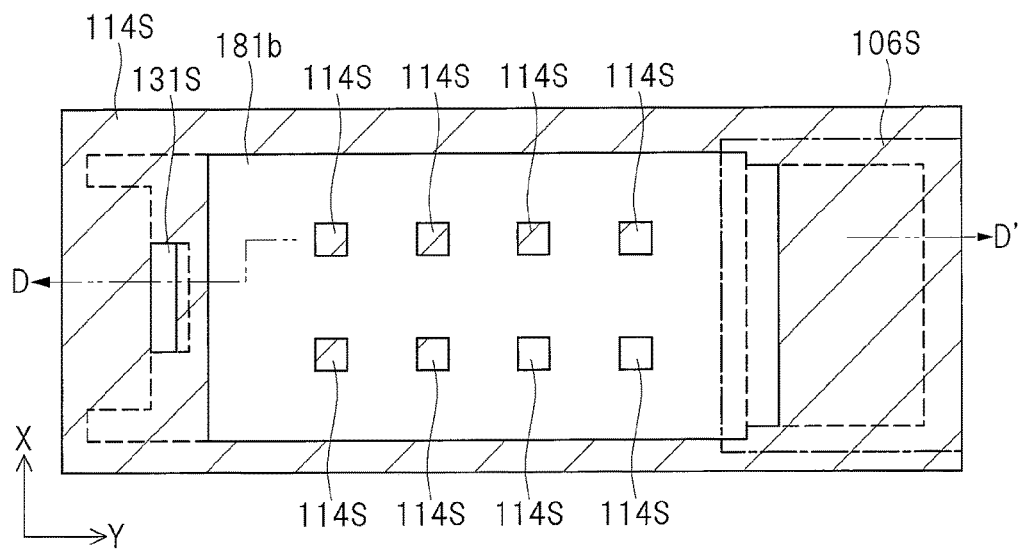
FIG. 24A is a plan view showing the manufacturing process of the gas sensor continued from FIG. 23A.
Figure 24B:
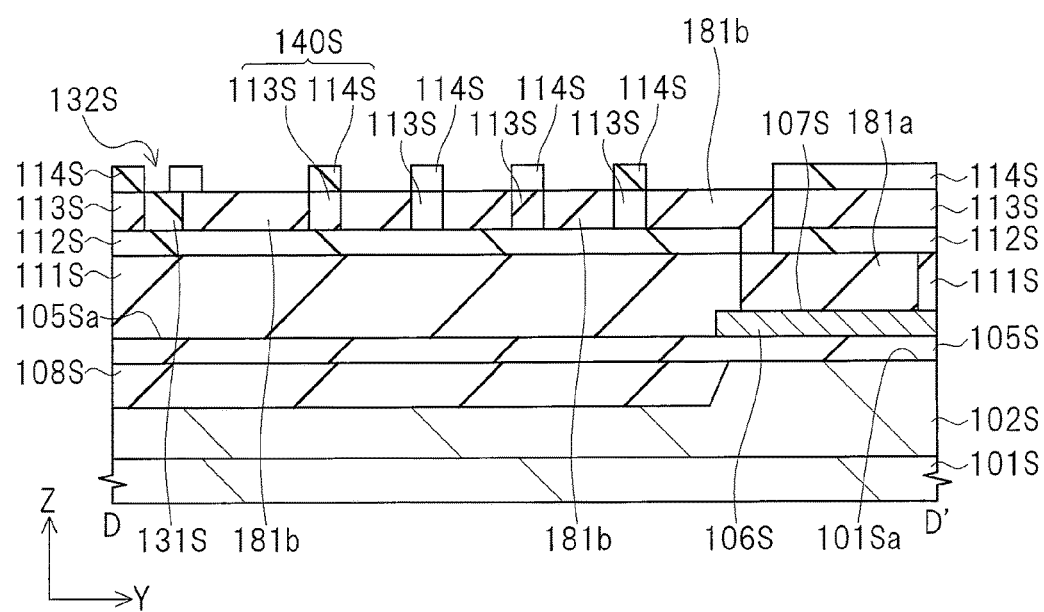
FIG. 24B is a cross-sectional view showing the manufacturing process of the gas sensor continued from FIG. 23B.

Next, as shown in FIG. 24A and FIG. 24B, after an insulation film 114S is formed on the insulation film 113S, the gas diffusion resistance film 131S, and the sacrificial film 181b, the insulation film 114S is partially removed, so that the gas diffusion resistance film 131S and the sacrificial film 181b are partially exposed. At this time, the insulation film 114S covers the upper surface of the insulation film 113S and a boundary portion between the gas diffusion resistance film 131S and the sacrificial film 181b. A pillar shaped portion 140S is formed by stacking a columnar structure made of the insulation film 114S on the upper surface of a columnar structure made of the insulation film 113S, which is formed in a region serving as the cavity 130S later. The insulation film 114S is made of silicon nitride (SiN), for example.

Further, a metal oxide such as, for example, titanium oxide ($TiO_2$) or chromium oxide ($Cr_2O_3$) is formed over an upper surface of the insulation film 114S to have a thickness of substantially several nanometers.

Note that, if the ion pump 150S is separated in a subsequent step (see the third embodiment described above), the separation portion is covered with the insulation film 114S.

Figure 25A:
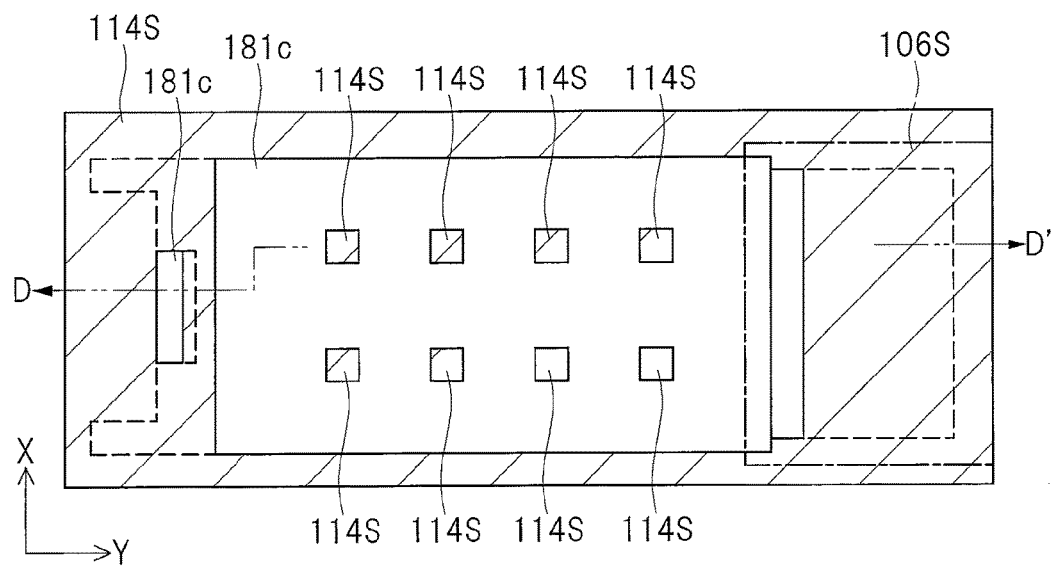
FIG. 25A is a plan view showing the manufacturing process of the gas sensor continued from FIG. 24A.
Figure 25B:
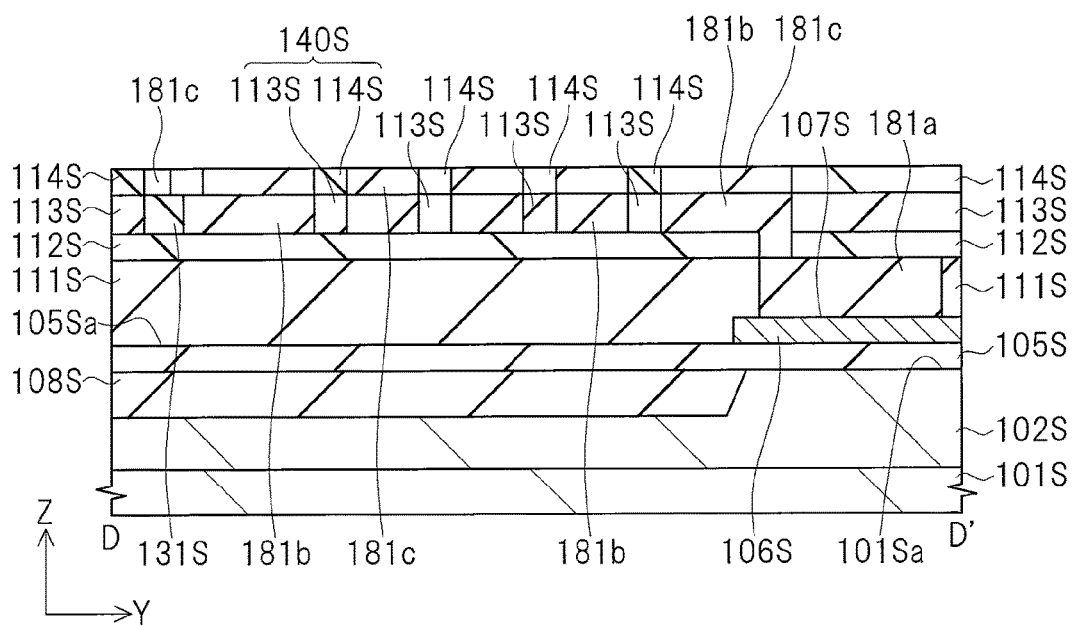
FIG. 25B is a cross-sectional view showing the manufacturing process of the gas sensor continued from FIG. 24B.

Next, as shown in FIG. 25A and FIG. 25B, after a sacrificial film 181c is formed over the insulation film 114S, the exposed gas diffusion resistance film 131S, and the exposed sacrificial film 181b, the sacrificial film 181c is polished, for example, so that the sacrificial film 181c is embedded in space portions between the insulation films 114S and the like adjacent to each other. The sacrificial film 181c is made of an organic material such as resist or a metal, for example. At this time, the sacrificial film 181c is removed from the upper surface of the insulation film 114S, but the metal oxide formed over the upper surface of the insulation film 114S remains.

Figure 26A:
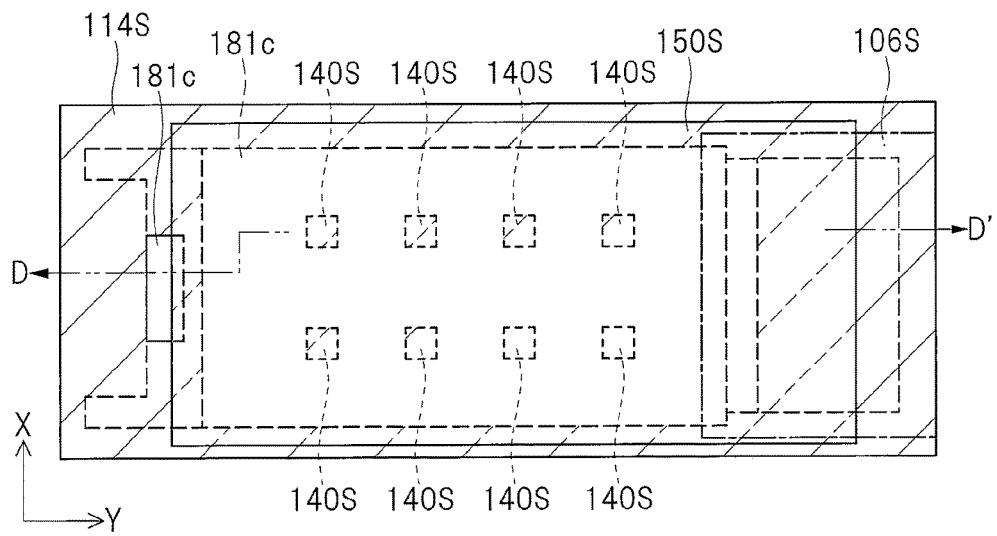
FIG. 26A is a plan view showing the manufacturing process of the gas sensor continued from FIG. 25A.
Figure 26B:
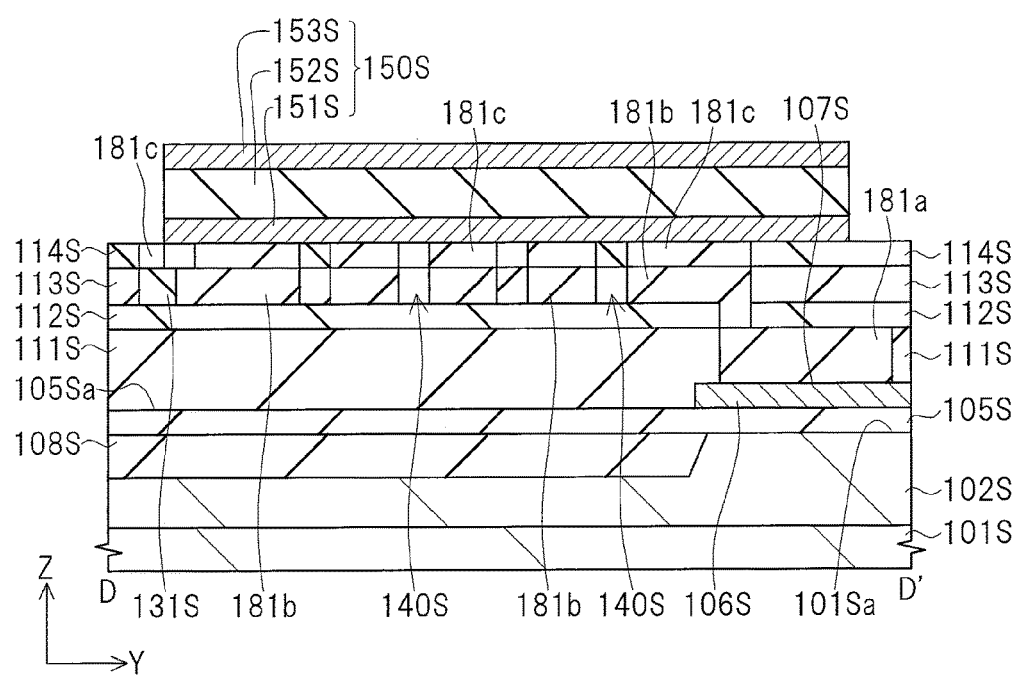
FIG. 26B is a cross-sectional view showing the manufacturing process of the gas sensor continued from FIG. 25B.

Next, as shown in FIG. 26A and FIG. 26B, an ion pump 150S including an ion pump electrode 151S, an ion conductive film 152S, and an ion pump electrode 153S is formed. The ion pump electrodes 151S and 153S are made of, for example, platinum (Pt), rhodium (Rf), or palladium (Pd). The ion conductive film 152S is made of, for example, zirconia ($ZrO_2$) or the like to which yttria ($Y_2O_3$) is added. The metal oxide described above remains over an interface between the insulation film 114S and the ion pump electrode 151S, and the metal oxide serves as an adhesion layer between the insulation film 114S and the ion pump electrode 151S.

Figure 27A:
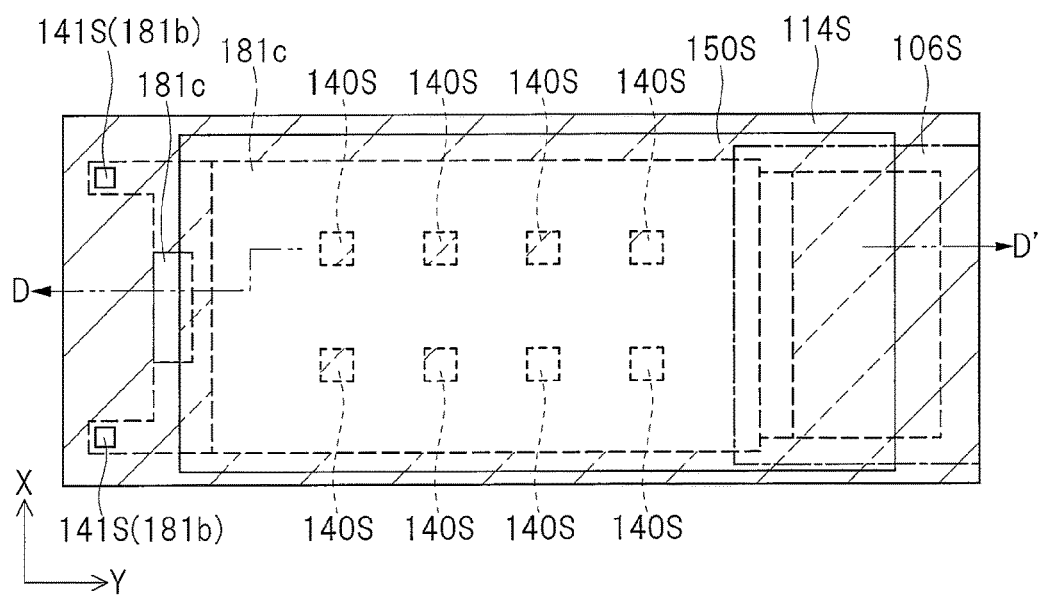
FIG. 27A is a plan view showing the manufacturing process of the gas sensor continued from FIG. 26A.
Figure 27B:
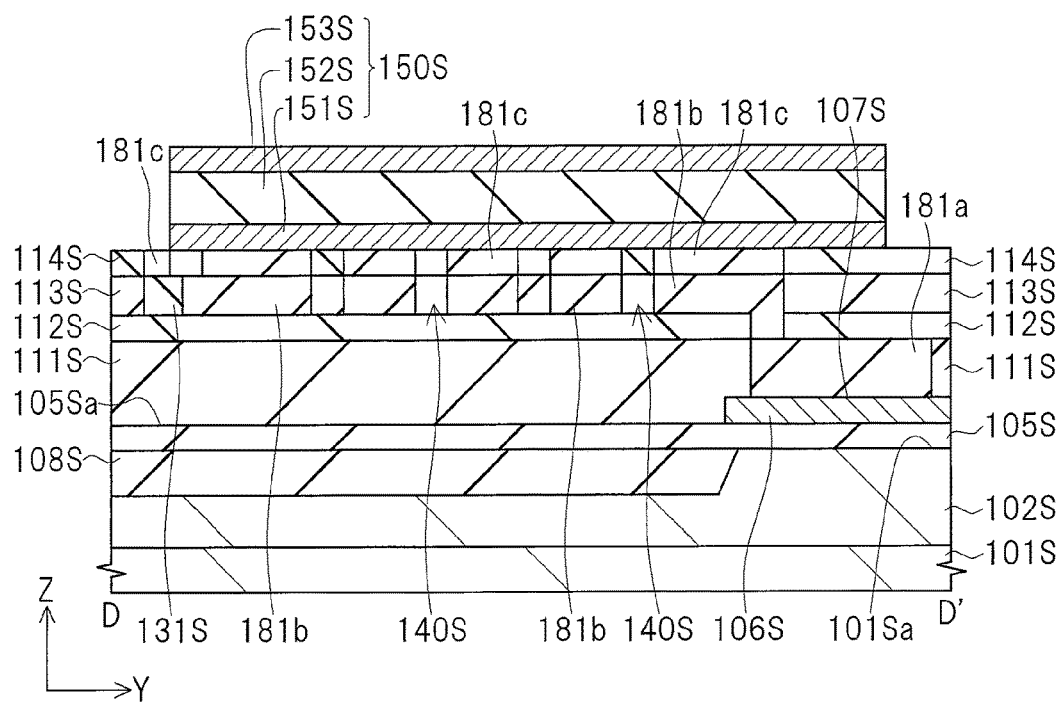
FIG. 27B is a cross-sectional view showing the manufacturing process of the gas sensor continued from FIG. 26B.

Next, as shown in FIG. 27A and FIG. 27B, the insulation film 114S is partially removed to form a contact portion 141S where a part of the sacrificial film 181c is exposed.

Figure 28A:
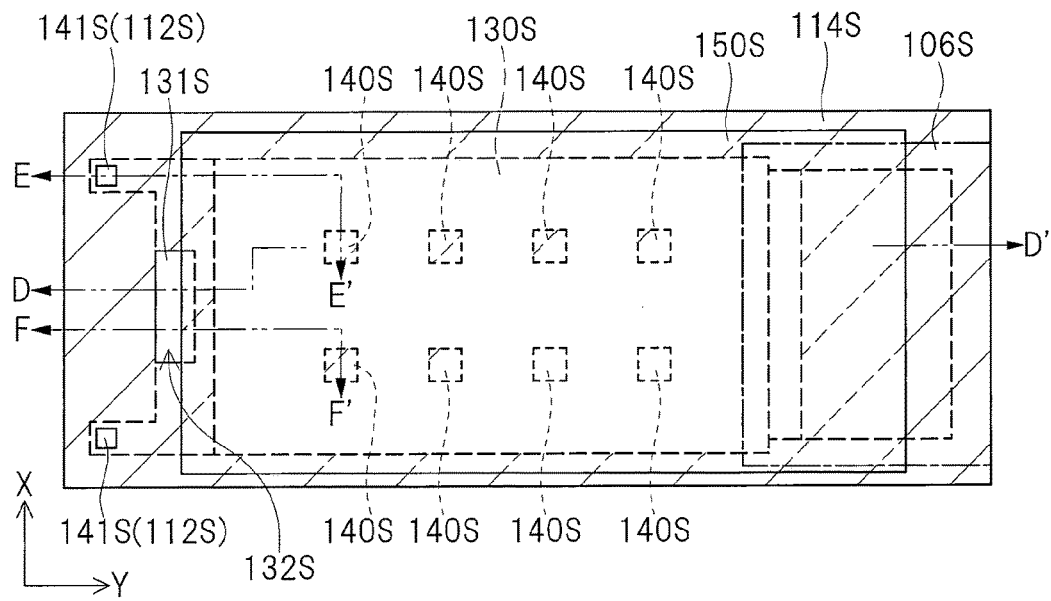
FIG. 28A is a plan view showing the manufacturing process of the gas sensor continued from FIG. 27A.
Figure 28B:
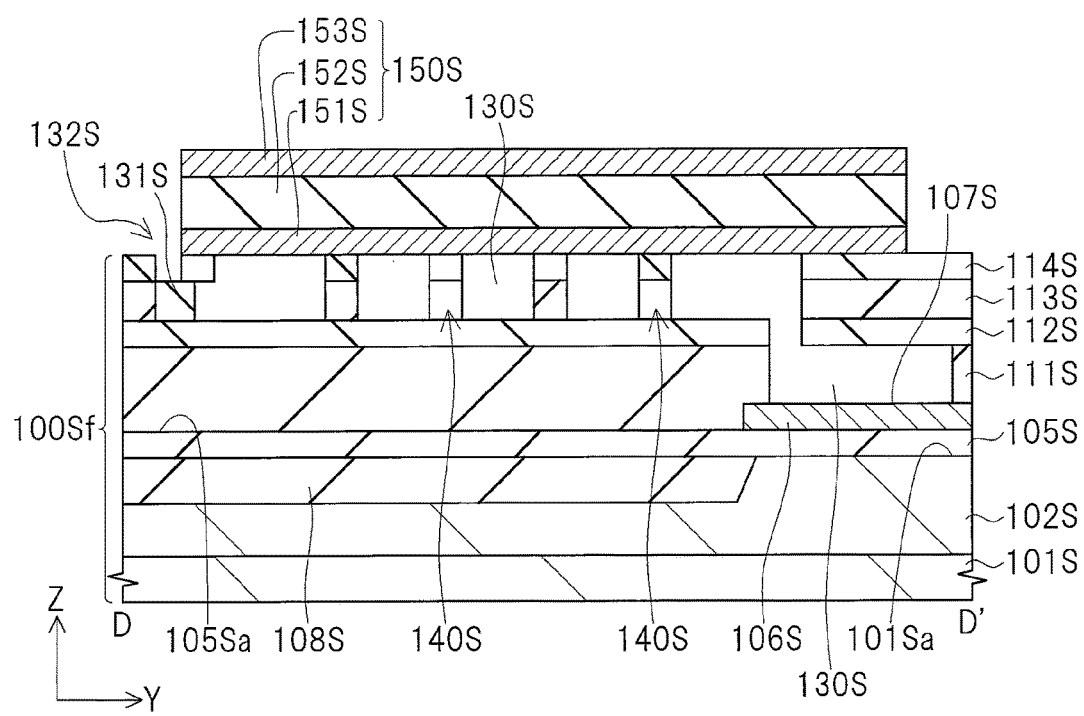
FIG. 28B is a cross-sectional view showing the manufacturing process of the gas sensor continued from FIG. 27B.

Next, as shown in FIG. 28A and FIG. 28B, the sacrificial films 181a, 181b, and 181c are removed from the contact portion 141S by, for example, wet etching or ashing, to form a cavity 130S.

In this process, the cavity 130S is formed. However, other than the gas introduction portion 132S in which the gas diffusion resistance film 131S is formed, the atmosphere and the cavity 130S are connected via the contact portion 141S. Accordingly, next, the method of closing the contact portion 141S will be described below.

Figure 29A:
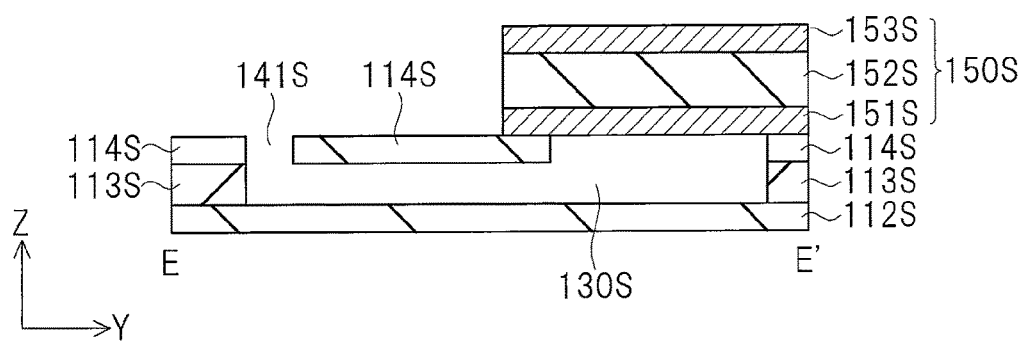
FIG. 29A is a cross-sectional view taken along a line E-E' in FIG. 28A.
Figure 29B:
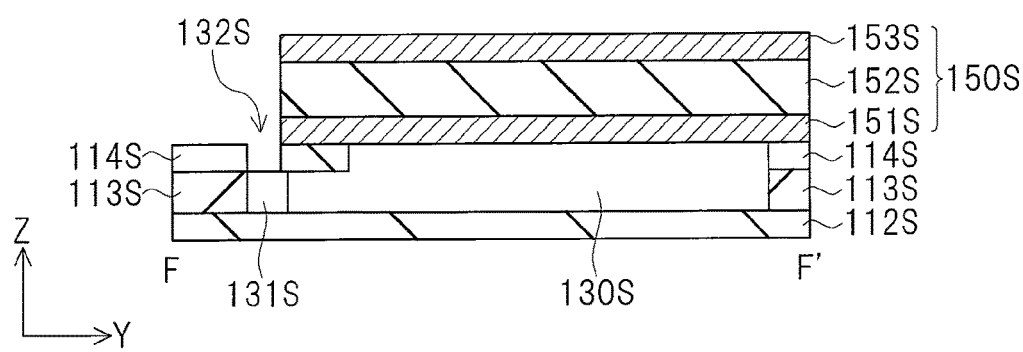
FIG. 29B is a cross-sectional view taken along a line F-F' in FIG. 28A.

FIG. 29A is a cross-sectional view taken along the line E-E' shown in FIG. 28A and shows a cross section of the contact portion 141S. FIG. 29B is a cross-sectional view taken along the line F-F' shown in FIG. 28A and shows a cross section of the gas diffusion resistance film 131S.

Figure 30A:
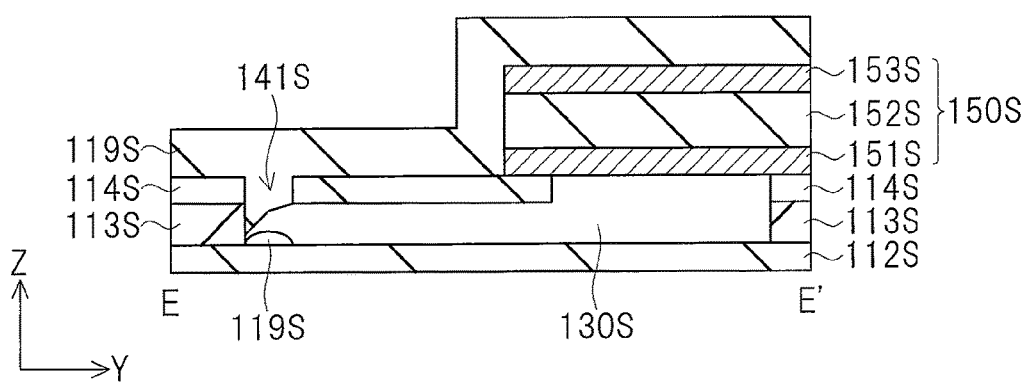
FIG. 30A is a cross-sectional view showing the manufacturing process of the gas sensor continued from FIG. 29A.
Figure 30B:
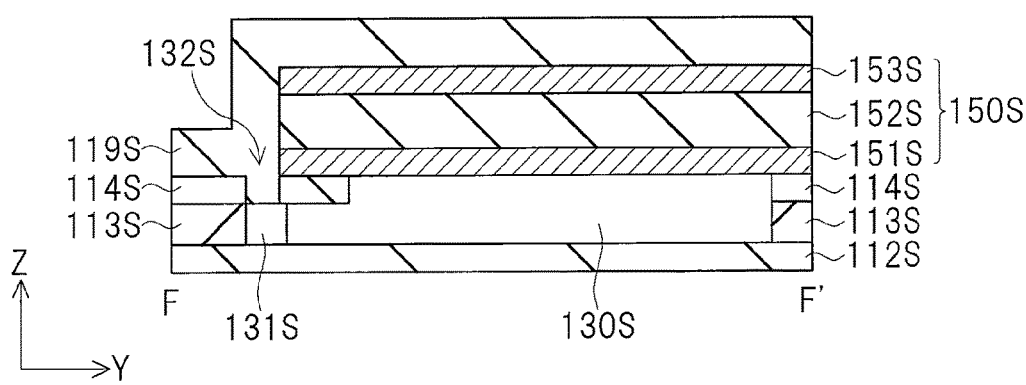
FIG. 30B is a cross-sectional view showing the manufacturing process of the gas sensor continued from FIG. 29B.

Next, as shown in FIG. 30A and FIG. 30B, a sealing film 119S is formed so as to cover the insulation film 114S, the ion pump 150S, and the exposed gas diffusion resistance film 131S. The sealing film 119S is made of, for example, silicon dioxide ($SiO_2$) or silicon nitride (SiN). Here, the contact portion 141S is closed by the sealing film 119S.

Figure 31A:
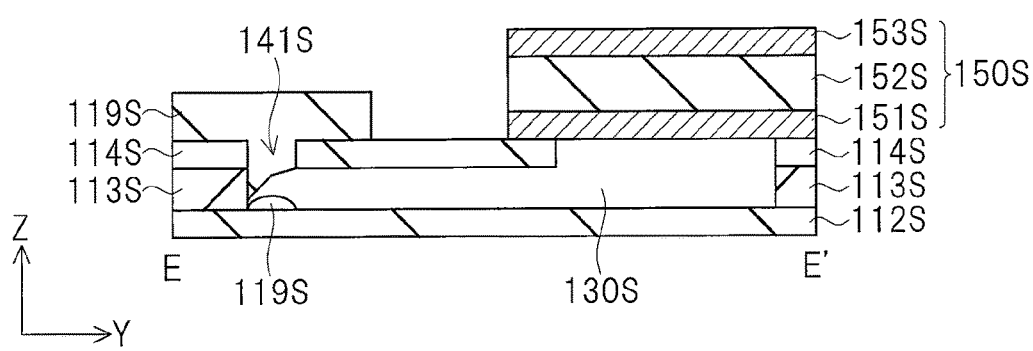
FIG. 31A is a cross-sectional view showing the manufacturing process of the gas sensor continued from FIG. 30A.
Figure 31B:
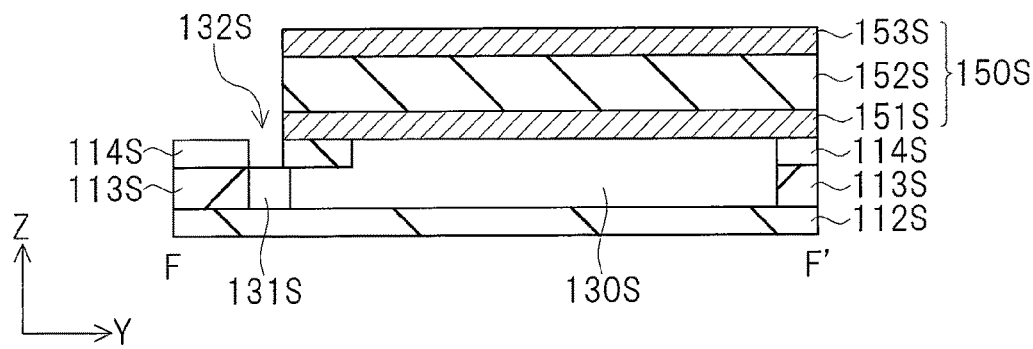
FIG. 31B is a cross-sectional view showing the manufacturing process of the gas sensor continued from FIG. 30B.

Next, as shown in FIG. 31A and FIG. 31B, the sealing film 119S in a region other than a periphery of the contact portion 141S is removed by lithography and etching (dry etching or wet etching). Since the sealing film 119S prevents gas diffusion, the gas diffusion between the atmosphere and the cavity 130S via the contact portion 141S is prevented. In the contact portion 141S, the sealing film 119S penetrates into the cavity 130S and remains. Therefore, it is desirable that the contact portion 141S is formed at a location that does not affect a flow path from the gas introduction portion 132S to the exposed portion 107S of the gate layer 106S of the sensor FET 100Sf.

With the above processes, the sensor FET 100Sf according to the fourth embodiment shown in FIG. 16 is almost completed.

Fifth Embodiment

Figure 32A:
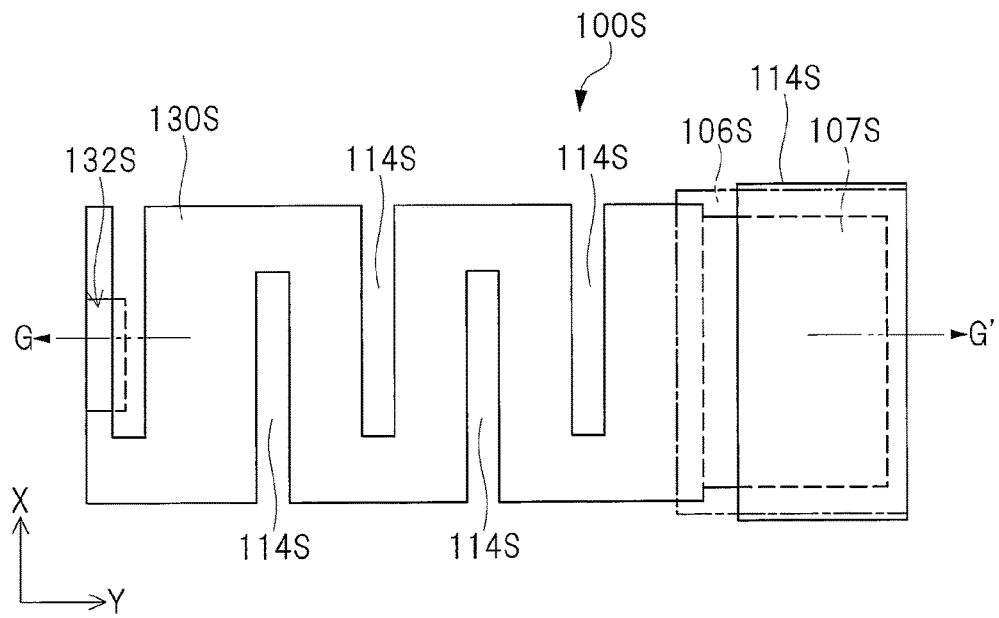
FIG. 32A is a plan view showing an example of a configuration of a sensor unit (sensor element) in a gas sensor according to a fifth embodiment.
Figure 32B:
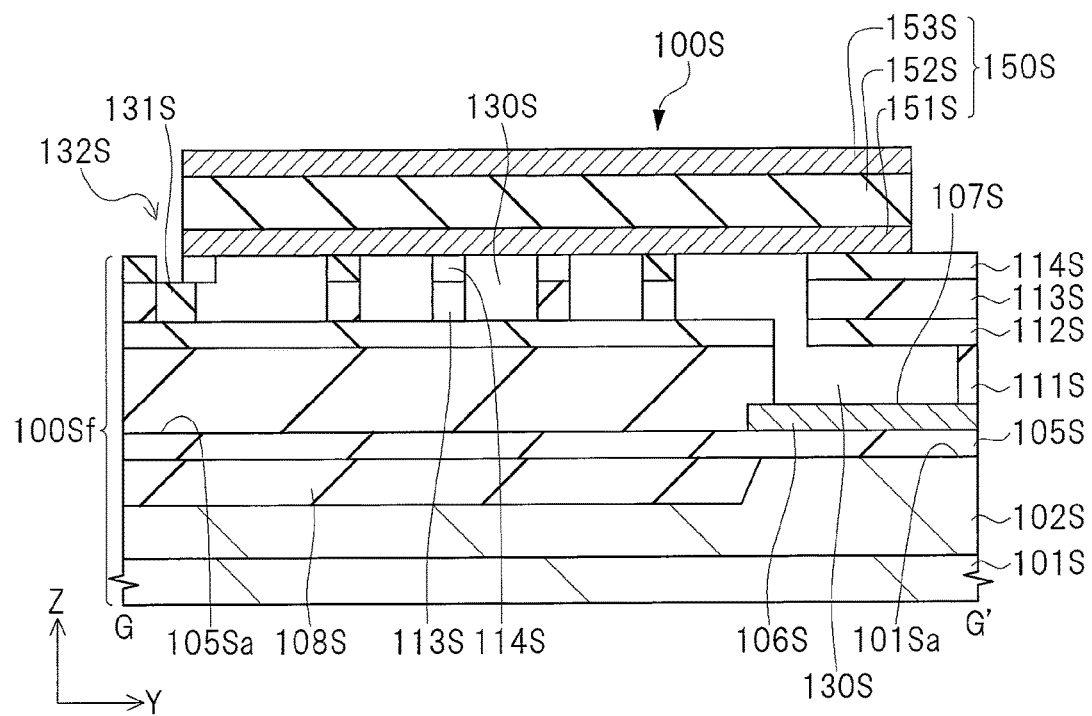
FIG. 32B is a cross-sectional view taken along a line G-G' in FIG. 32A.

A configuration of a gas sensor according to the fifth embodiment will be described with reference to FIG. 32. FIG. 32A is a plan view showing an example of a configuration of a sensor unit (sensor element) in the gas sensor according to the fifth embodiment. FIG. 32B is a cross-sectional view taken along a line G-G' in FIG. 32A. Note that FIG. 32A shows a plan view seen through an ion pump 150S.

In the sensor element 100S according to the fourth embodiment described above, the pillar shaped portion 140S made of a columnar structure is provided inside the cavity 130S, and the cavity 130S is reinforced by connecting the upper surface and the lower surface of the cavity 130S. However, the reinforcement of the cavity 130S is not limited thereto.

As shown in FIG. 32A and FIG. 32B, the cavity 130S can be also reinforced by causing the shape of the cavity 130S to meander in an XY plane. Furthermore, the gas flow path from the gas introduction portion 132S to the exposed portion 107S of the gate layer 106S of the sensor FET 100Sf is lengthened, and in most of the gas flow path, the ion pump 150S is in contact with the upper surface of the cavity 130S. Therefore, diffusion in the Z direction sufficiently occurs while the atmosphere gas diffuses in the cavity 130S.

As a result, the sensor FET 100Sf according to the fifth embodiment has an advantage of sufficiently removing the interfering gas as a result of having the entire atmosphere come into contact with the ion pump 150S, in addition to an effect of reinforcing the cavity 130S.

Sixth Embodiment

Figure 33A:
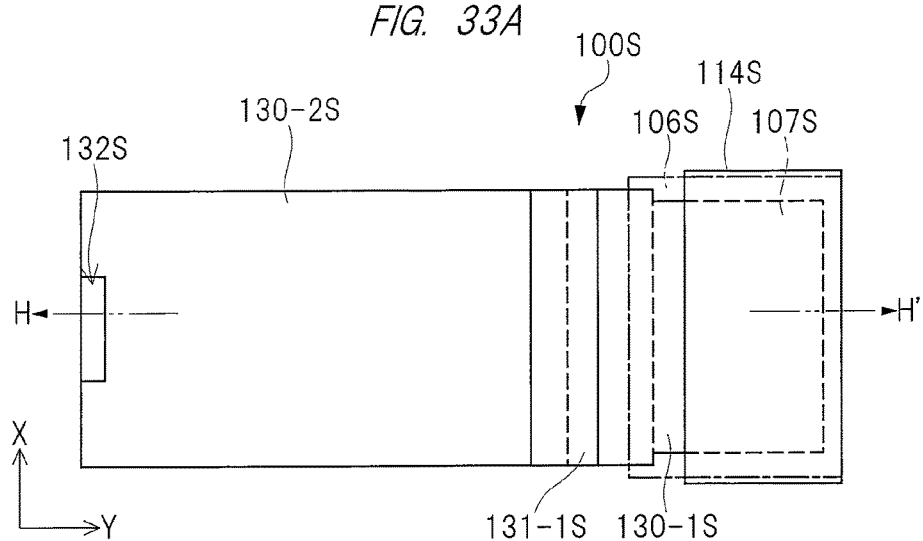
FIG. 33A is a plan view showing an example of a configuration of a sensor unit (sensor element) in a gas sensor according to a sixth embodiment.
Figure 33B:
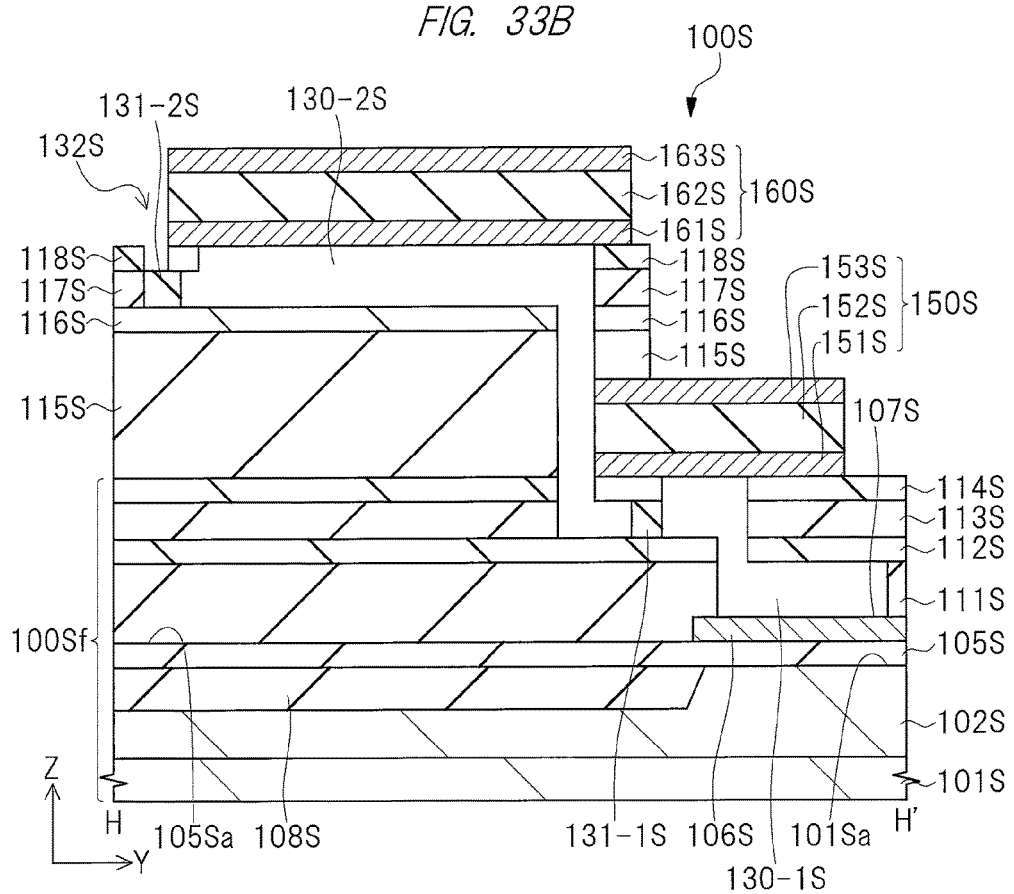
FIG. 33B is a cross-sectional view taken along a line H-H' in FIG. 33A.

A configuration of a gas sensor according to the sixth embodiment will be described with reference to FIG. 33. FIG. 33A is a plan view showing an example of a configuration of a sensor unit (sensor element) in the gas sensor according to the sixth embodiment. FIG. 33B is a cross-sectional view taken along a line H-H' in FIG. 33A. Note that FIG. 33A shows a plan view seen through the ion pumps 150S and 160S and the insulation films 115S to 118S.

In the sensor element 100SA according to the third embodiment described above, in the two ion pumps 150-1S and 150-2S, the ion pump electrode 151-1S and the ion pump electrode 151-2S are formed by the film of the same layer, the ion conductive film 152-1S and the ion conductive film 152-2S are formed by the film of the same layer, and the ion pump electrode 153-1S and the ion pump electrode 153-2S are formed by the film of the same layer. However, the embodiment is not limited thereto. The two ion pumps, i.e., the ions pump 150S and the ion pump 160S, can be formed by respective films of different layers.

As shown in FIG. 33A and FIG. 33B, an ion pump 150S including an ion pump electrode 151S, an ion conductive film 152S, and an ion pump electrode 153S is formed, and furthermore, insulation films 115S to 118S serving as gas diffusion prevention films are formed over the ion pump 150S. The insulation film 115S and the insulation film 117S are made of, for example, silicon dioxide ($SiO_2$). The insulation film 116S and the insulation film 118S are made of, for example, silicon nitride (SiN).

A cavity 130-2S is formed in a part of the insulation films 115S to 118S. This cavity 130-2S is connected to a cavity 130-1S whose periphery is covered with the gate layer 106S, the insulation films 111S to 114S, and the ion pump 150S. Also, a gas diffusion resistance film 131-1S is provided between the cavity 130-1S and the cavity 130-2S.

The periphery of cavity 130-2S is covered with the insulation films 112S to 118S and the ion pump 160S. The cavity 130-2S is connected to the atmosphere via the gas introduction portion 132S having the gas diffusion resistance film 131-2S.

The ion pump 160S includes an ion pump electrode 161S, an ion conductive film 162S, and an ion pump electrode 163S. That is, the ion conductive film 162S and the ion pump electrode 163S are laminated over the ion pump electrode 161S, and the ion pump 160S is formed by the ion pump electrode 161S, the ion conductive film 162S, and the ion pump electrode 163S. The ion pump electrodes 161S and 163S are made of, for example, platinum (Pt), rhodium (Rh), or palladium (Pd). For example, the ion conductive film 162S is made of, for example, zirconia ($ZrO_2$) to which yttria ($Y_2O_3$) or the like is added.

In the sensor element 100S according to the sixth embodiment, the two ion pumps 150S and 160S are formed, and therefore, for example, according to a method of removing oxygen gas with the ion pump 160S and removing hydrogen gas with the ion pump 150S, both oxidation and reduction processes of the gas in the cavities 130-1S and 130-2S are performed, so that the interfering gas can be removed.

Alternatively, the gas concentration of the oxygen gas after the oxygen gas removal can be confirmed by, for example, removing the oxygen gas with the ion pump 160S and measuring an ion current of the ion pump 150S.

These operations are also possible in the sensor element 100SA according to the third embodiment described above. However, in the sensor element 100S according to the sixth embodiment, different electrode materials and ion conductive film materials can be used for the ion pump 150S and the ion pump 160S. Thus, it is possible to independently select the electrode material and the ion conductive film material suitable for a role of each of the ion pump 150S and the ion pump 160S. Therefore, it is possible to achieve removal of the interfering gas in the sensor element 100S according to the sixth embodiment more appropriately than the sensor element 100SA according to the third embodiment. In the sixth embodiment, the two ion pumps 150S and 160S are formed, but three or more ion pumps may be formed.

Seventh Embodiment

Figure 35:
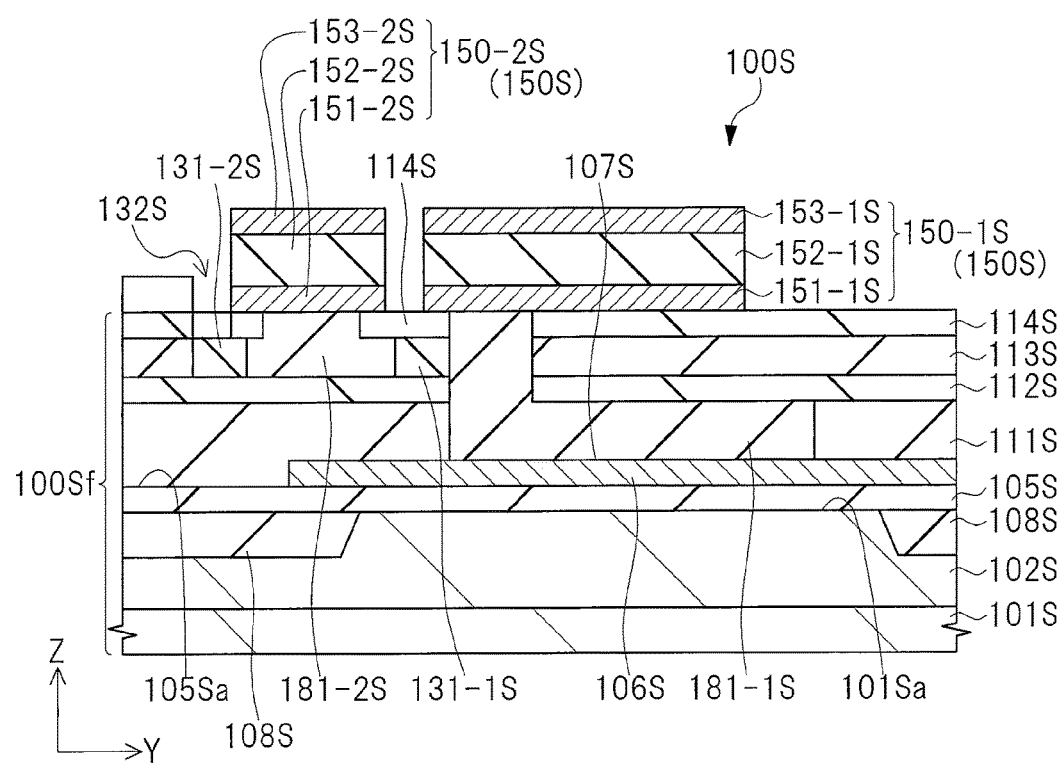
FIG. 35 is a cross-sectional view showing an example of a configuration of a sensor unit (sensor element) in a gas sensor filled with the sacrificial film according to the seventh embodiment.

A method of removing a sacrificial film in a manufacturing process of a gas sensor according to the seventh embodiment will be described with reference to FIG. 34 and FIG. 35. FIG. 34A is a plan view showing an example of a cavity filled with a sacrificial film according to the seventh embodiment. FIG. 34B is a plan view showing an example of the cavity from which the sacrificial film has been removed according to the seventh embodiment. FIG. 35 is a cross-sectional view showing an example of a configuration of a sensor unit (sensor element) in a gas sensor filled with the sacrificial film according to the seventh embodiment.

For example, the sensor FET 100Sf (for example, see FIG. 32) described in the fifth embodiment described above has a structure in which the path along the cavity 130S is long, and when the sacrificial film is removed via one contact hole formed at one end portion of the cavity 130S, the process time increases, and the manufacturing cost increases.

However, as shown in FIG. 34A, in the case of the sensor FET 100Sf shown in the seventh embodiment, a plurality of contact portions 141S are formed along the meandering path, and the sacrificial film is removed via the plurality of contact portions 141S. Thus, it is possible to shorten the process time for removing the sacrificial film via the contact portions 141S.

Further, as shown in FIG. 34B, in a manner similar to the method described above with reference to FIG. 29 to FIG. 31 according to the fourth embodiment, for example, the plurality of contact portions 141S are all closed with the sealing film 119S, so that only the gas introduction portion 132S is the part through which the cavity 130S is exposed to the atmosphere. Since the sealing film 119S prevents gas diffusion, the gas diffusion between the atmosphere and the cavity 130S via the contact portion 141S is prevented. In the contact portion 141S, the sealing film 119S penetrates into the cavity 130S and remains. Therefore, it is desirable that the contact portion 141S is formed at a location that does not affect the flow path from the gas introduction portion 132S to the exposed portion 107S of the gate layer 106S of the sensor FET 100Sf.

Also, in the sensor FET 100Sf (for example, see FIG. 13) described in the third embodiment described above and the sensor FET 100Sf (for example, see FIG. 33) described in the sixth embodiment described above, for example, the cavity 130S is separated by the gas diffusion resistance film 131-1S into two. When such structure is manufactured, the sacrificial film is separated by the gas diffusion resistance film 131-1S.

For example, as shown in FIG. 35, in the sensor FET 100Sf shown in the seventh embodiment, the sacrificial film is separated into the sacrificial film 181-1S and the sacrificial film 181-2S by the gas diffusion resistance film 131-1S.

In such a case, one or more contact portions are formed for each portion of the sacrificial film 181-1S and the sacrificial film 181-2S which are separated, so that the sacrificial film 181-1S and the sacrificial film 181-2S are removed.

After the sacrificial film 181-1S and the sacrificial film 181-2S are removed, for example, in a similar manner to the method described above with reference to FIG. 29 to FIG. 31 according to the fourth embodiment, the plurality of contact portions are all closed with the sealing film, so that only the gas introduction portion 132S is the part through which the cavity 130S is exposed to the atmosphere. Since the sealing film 119S prevents gas diffusion, the gas diffusion between the atmosphere and the cavity 130S via the contact portion 141S is prevented. In the contact portion, the sealing film penetrates into the cavity 130S and remains. Therefore, it is desirable that the contact portion is formed at a location that does not affect the flow path from the gas introduction portion 132S to the exposed portion 107S of the gate layer 106S of the sensor FET 100Sf.

Eighth Embodiment

Figure 36A:
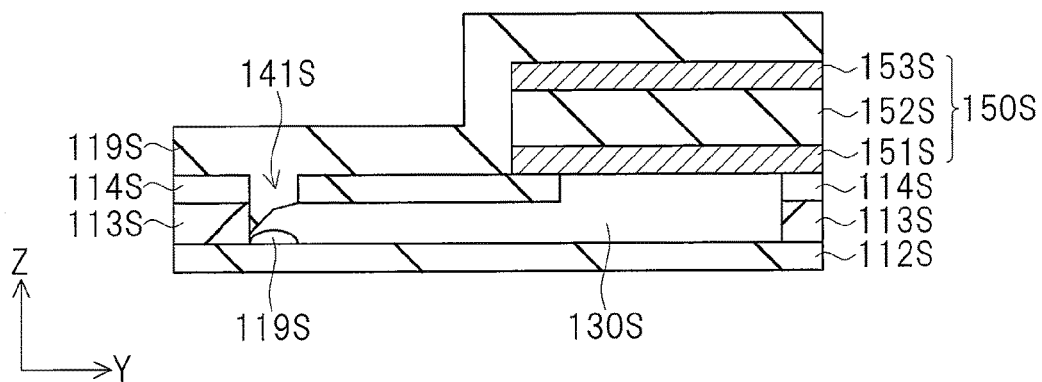
FIG. 36A is a cross-sectional view showing a contact portion as an example of a manufacturing process of a sensor unit (sensor element) in a gas sensor according to an eighth embodiment.
Figure 36B:
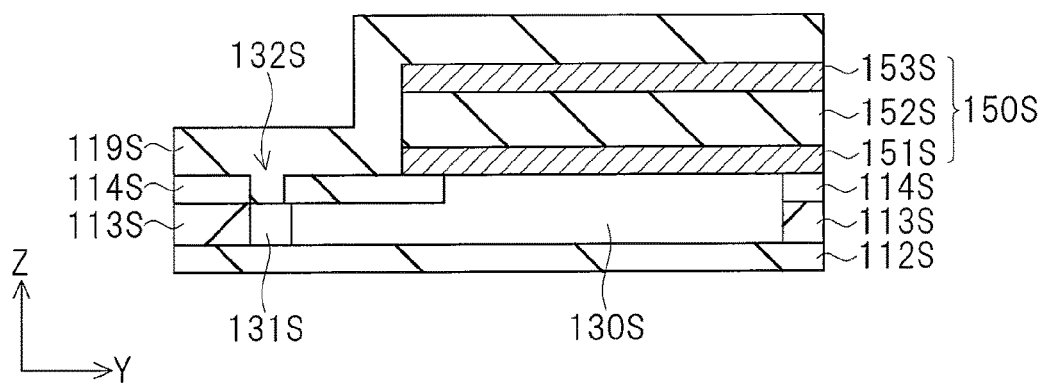
FIG. 36B is a cross-sectional view showing a gas diffusion prevention film as an example of the manufacturing process of the sensor unit (sensor element) in the gas sensor according to the eighth embodiment.
Figure 37A:
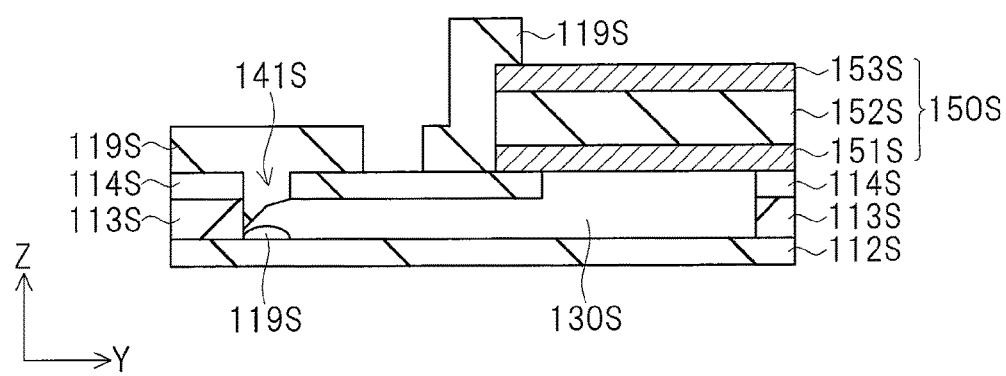
FIG. 37A is a cross-sectional view showing the manufacturing process of the gas sensor continued from FIG. 36A.
Figure 37B:
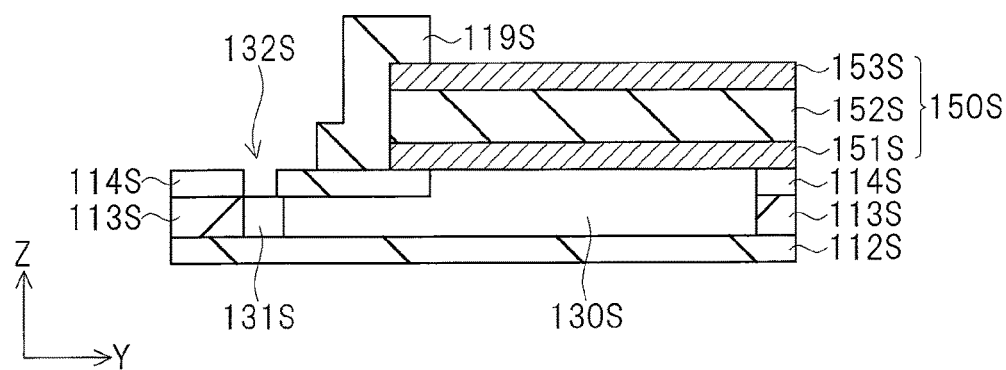
FIG. 37B is a cross-sectional view showing the manufacturing process of the gas sensor continued from FIG. 36B.

A configuration of a sensor unit (sensor element) in a gas sensor according to the eighth embodiment will be described with reference to FIG. 36 and FIG. 37. FIG. 36A is a cross-sectional view showing a contact portion of the sensor unit (sensor element) according to the eighth embodiment, and FIG. 37A is a cross-sectional view showing the contact portion of the sensor unit (sensor element) continued from FIG. 36A (each of FIG. 36A and FIG. 37A corresponds to the cross-section taken along the line E-E' in FIG. 28 according to the fourth embodiment, for example). FIG. 36B is a cross-sectional view showing a gas diffusion prevention film of the sensor unit (sensor element) according to the eighth embodiment, and FIG. 37B is a cross-sectional view showing the gas diffusion prevention film of the sensor unit (sensor element) continued from FIG. 36B (each of FIG. 36B and FIG. 37B corresponds to the cross-section taken along the line F-F' in FIG. 28 according to the fourth embodiment, for example).

In the sensor element 100S according to the fourth embodiment described above, after the sealing film 119S is formed so as to cover the ion pump 150S and the exposed gas diffusion resistance film 131S when the contact portion 141S is closed, the sealing film 119S in the region other than the periphery of the contact portion 141S is removed (for example, see FIG. 30A and FIG. 30B and FIG. 31A and FIG. 31B). That is, the upper surface and the side surface of the ion pump 150S are not covered with the sealing film 119S.

However, the sealing film 119S can also be left on the side surface of the end portion of the ion pump 150S.

For example, as shown in FIG. 36A and FIG. 36B, the sealing film 119S is formed so as to cover the insulation film 114S, the ion pump 150S, and the exposed gas diffusion resistance film 131S. The sealing film 119S is made of, for example, silicon dioxide ($SiO_2$) or silicon nitride (SiN). Here, the contact portion 141S is closed by the sealing film 119S.

Next, as shown in FIG. 37A and FIG. 37B, the sealing film 119S is processed by lithography and etching (dry etching or wet etching). Here, by leaving the sealing film 119S around the contact portion 141S, the contact portion 141S is closed by the sealing film 119S. Further, a part of the upper surface of the ion pump electrode 153S is exposed from the sealing film 119S, but the sealing film 119S is left so as to cover the exposed side surface of the end portion of the ion conductive film 152S.

Since the sealing film 119S can prevent the gas diffusion, it is possible to prevent the gas diffusion between the atmosphere and the cavity 130S via the contact portion 141S. Further, it is possible to prevent unnecessary gas diffusion via the side surface of the ion conductive film 152S which is not covered with the ion pump electrodes 151S and 153S.

Ninth Embodiment

Figure 38:
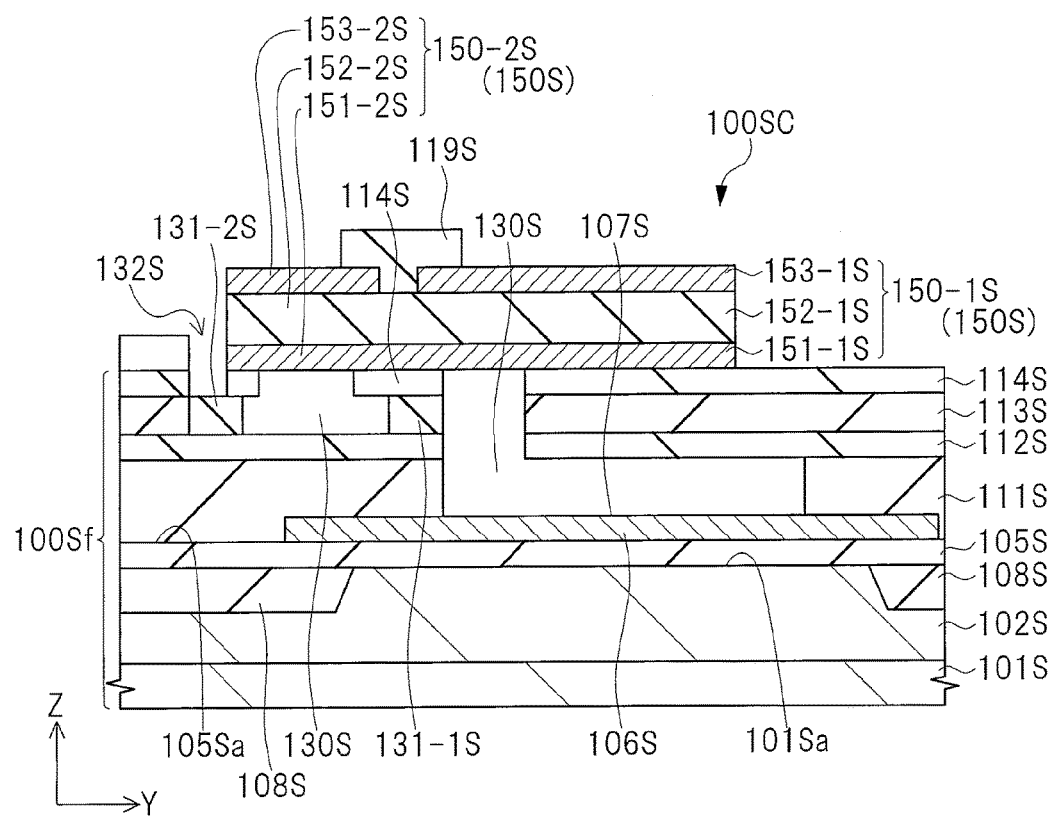
FIG. 38 is a cross-sectional view showing an example of a configuration of a sensor unit (sensor element) in a gas sensor according to a ninth embodiment.

A configuration of a gas sensor according to the ninth embodiment will be described with reference to FIG. 38. FIG. 38 is a cross-sectional view showing an example of a configuration of a sensor unit (sensor element) in the gas sensor according to the ninth embodiment.

In the sensor element according to the eighth embodiment described above, the side surface of the end portion of the ion conductive film 152S exposed to the atmosphere is covered with the sealing film 119S, and unnecessary gas diffusion is prevented. However, in the ion pump 150S having a configuration in which not only the side surface of the end portion of the ion conductive film 152S but also a part of the ion conductive film 152S is exposed to the atmosphere, the other exposed surface of the ion conductive film 152S can be covered with the sealing film 119S.

For example, in the sensor element 100SC according to the third example of the third embodiment described above, a part of the upper surfaces of the ion conductive films 152-1S and 152-2S are exposed to the atmosphere. In this case, as shown in FIG. 38, the portions of the upper surfaces of the ion conductive films 152-1S and 152-2S not covered with the ion pump electrodes 153-1S and 153-2S can be covered with the sealing film 119S. As a result, it is possible to prevent unnecessary gas diffusion via the portions where the upper surfaces of the ion conductive films 152-1S and 152-2S are exposed.

In the foregoing, the invention made by the inventors of the present invention has been concretely described based on the embodiments. However, it is needless to say that the present invention is not limited to the foregoing embodiments and various modifications and alterations can be made within the scope of the present invention.

The present invention includes at least the following embodiments.

[Supplementary Note 1]

A method of manufacturing a gas sensor, including:

(a) a step of forming a well having a first depth from a main surface of a semiconductor substrate over the semiconductor substrate;

(b) a step of forming a gate insulation film over the well;

(c) a step of forming a gate layer over the gate insulation film;

(d) a step of forming a sacrificial film over the gate layer;

(e) a step of forming a first gas diffusion prevention film on the sacrificial film;

(f) a step of forming a hole reaching the sacrificial film in the first gas diffusion prevention film; and (g) a step of forming a cavity exposing a part of a front surface of the gate layer by removing the sacrificial film via the hole.

[Supplementary Note 2]

The method of manufacturing a gas sensor according to Supplementary Note 1, in which, in the (f) step, a plurality of the holes are formed, and after the (g) step, the method further includes:

(h) a step of forming a first sealing film over the first gas diffusion prevention film such that the cavity is not completely filled; and (i) a step of sealing each of the plurality of the holes with the first sealing film by processing the first sealing film.

[Supplementary Note 3]

The method of manufacturing a gas sensor according to Supplementary Note 1, between the (e) step and the (f) step, the method further including:

(j) a step of forming an opening portion in the first gas diffusion prevention film; and (k) a step of forming an ion pump in which a first ion pump electrode, an ion conductive film, and a second ion pump electrode are laminated over the first gas diffusion prevention film so as to cover the opening portion, in which, in the (g) step, a portion of a lower surface of the first ion pump electrode is exposed to the cavity.

[Supplementary Note 4]

The method of manufacturing a gas sensor according to Supplementary Note 3, after the (k) step, the method further including:

(l) a step of forming a second sealing film covering an exposed portion of the ion conductive film.

[Supplementary Note 5]

The method of manufacturing a gas sensor according to Supplementary Note 1, between the (c) step and the (d) step, the method further including:

(m) a step of forming a second gas diffusion prevention film over the gate layer; and (n) a step of exposing a portion of a front surface of the gate layer by removing a part of the second gas diffusion prevention film.

[Supplementary Note 6]

The method of manufacturing a gas sensor according to Supplementary Note 1, between the (d) step and the (e) step, the method further including:

(o) a step of forming a gas diffusion resistance film in contact with the sacrificial film, in which the first gas diffusion prevention film is not formed over a part of an upper surface of the gas diffusion resistance film.

What is claimed is:

1. A gas sensor comprising:
a work function type sensor provided in a main surface of a semiconductor substrate;
a first ion pump removing a first interfering gas component from a detection target gas; and
a first gas diffusion prevention film formed between the work function type sensor and the first ion pump,
wherein the work function type sensor includes:
the semiconductor substrate;
a well having a first depth from the main surface of the semiconductor substrate and formed in the semiconductor substrate;
a gate insulation film formed over the well; and
a gate layer formed over the gate insulation film,
wherein the first ion pump includes:
a first ion conductive film;

a first ion pump electrode formed to be in contact with a lower surface of the first ion conductive film; and
a second ion pump electrode formed to be in contact with an upper surface of the first ion conductive film,
wherein a first cavity into which the detection target gas is introduced is formed in the first gas diffusion prevention film,
wherein a part of a front surface of the gate layer is exposed to the first cavity, and
wherein a part of a lower surface of the first ion pump electrode is exposed to the first cavity.

2. The gas sensor according to claim 1,
wherein the work function type sensor further includes:
a source diffusion layer formed in the well and having a second depth shallower than the first depth from the main surface of the semiconductor substrate; and
a drain diffusion layer formed in the well to be spaced apart from the source diffusion layer and having a third depth shallower than the first depth from the main surface of the semiconductor substrate, and
wherein the work function type sensor is a field effect transistor type sensor.

3. The gas sensor according to claim 2,
wherein the gate layer is an annular shape surrounded by a circular outer shape and a circular inner shape in plan view, and the circular shape constituting the inner shape is smaller than the circular shape constituting the outer shape.

4. The gas sensor according to claim 3,
wherein, outside the outer shape of the gate layer and inside the inner shape of the gate layer in plan view, a plurality of gas introduction portions are formed to introduce the detection target gas to the first cavity.

5. The gas sensor according to claim 1,
wherein the first gas diffusion prevention film includes a first portion on a side of the work function type sensor and a second portion on a side of the first ion pump,
wherein the part of the front surface of the gate layer and a part of the first portion of the first gas diffusion prevention film are exposed on a lower surface of the first cavity, and
wherein a part of the lower surface of the first ion pump electrode and a part of the second portion of the first gas diffusion prevention film are exposed on an upper surface of the first cavity.

6. The gas sensor according to claim 1,
wherein the first ion conductive film includes zirconia.

7. The gas sensor according to claim 1,
wherein the gate layer includes platinum, rhodium, or palladium.

8. The gas sensor according to claim 1,
wherein the gate layer includes a first layer including platinum, rhodium, or palladium, and a second layer formed between the gate insulation film and the first layer and made of a metal oxide including zirconia.

9. The gas sensor according to claim 1,
wherein the first ion pump electrode and the second ion pump electrode include platinum, rhodium, or palladium.

10. The gas sensor according to claim 1,
wherein the first gas diffusion prevention film has a multi-layer structure in which a silicon dioxide film and a silicon nitride film are alternately laminated.

11. The gas sensor according to claim 1,
wherein the first ion pump electrode, the second ion pump electrode, or the first ion pump electrode and the second ion pump electrode are each separated into two or more, and supplied with a potential different from each other.

12. The gas sensor according to claim 1,
wherein the first cavity is connected to an external atmosphere via a first gas diffusion resistance film.

13. The gas sensor according to claim 1,
wherein an upper surface of the first cavity and a lower surface of the first cavity are connected by a pillar shaped portion formed by an insulation film.

14. The gas sensor according to claim 1, further comprising:
a second ion pump removing a second interfering gas component from the detection target gas;
a second gas diffusion prevention film formed between the first ion pump and the second ion pump,
wherein the second ion pump includes:
a second ion conductive film;
a third ion pump electrode formed to be in contact with a lower surface of the second ion conductive film; and
a fourth ion pump electrode formed to be in contact with an upper surface of the second ion conductive film,
wherein a second distance from the main surface of the semiconductor substrate to the second ion conductive film is larger than a first distance from the main surface of the semiconductor substrate to the first ion conductive film,
wherein a second cavity into which the detection target gas is introduced and which is connected to the first cavity is formed in the second gas diffusion prevention film, and
wherein a part of a lower surface of the third ion pump electrode is exposed to the second cavity.

15. The gas sensor according to claim 14,
wherein the second cavity is connected to an external atmosphere via a second gas diffusion resistance film, and
wherein a third gas diffusion resistance film is provided between the first cavity and the second cavity.

* * * * *